United States Patent
Clapham et al.

(10) Patent No.: US 7,425,614 B2
(45) Date of Patent: Sep. 16, 2008

(54) NEUROPROTECTIVE THERAPEUTICS PREVENTING ERK/MAPK ACTIVATION THROUGH THE NMDA RECEPTOR

(75) Inventors: David Clapham, Wellesley, MA (US); Grigory Krapivinsky, Newton, MA (US); Igor Medina, Marseilles (FR); Ben-Ari Yehezkel, La Ciotat (FR)

(73) Assignees: Children's Medical Center Corporation, Boston, MA (US); Institut National de la Sante et de la Recherche Medical (INSERM), Paris (FR)

( * ) Notice: Subject to any disclaimer, the term of this patent is extended or adjusted under 35 U.S.C. 154(b) by 0 days.

(21) Appl. No.: 11/181,330

(22) Filed: Jul. 14, 2005

(65) Prior Publication Data

US 2006/0035283 A1 Feb. 16, 2006

Related U.S. Application Data

(63) Continuation of application No. PCT/US2004/001209, filed on Jan. 16, 2004.

(60) Provisional application No. 60/440,679, filed on Jan. 17, 2003.

(51) Int. Cl.
 *C07K 14/47* (2006.01)
 *C12N 5/10* (2006.01)
 *C12N 1/19* (2006.01)
 *C12N 1/21* (2006.01)

(52) U.S. Cl. ............... 530/350; 435/69.1; 435/69.7; 435/252.3; 435/254.2; 435/348; 435/349; 435/366

(58) Field of Classification Search ............ None
See application file for complete search history.

(56) References Cited

U.S. PATENT DOCUMENTS

| 5,656,595 | A | * | 8/1997 | Schweighoffer et al. | ...... 514/12 |
| 6,319,955 | B1 | | 11/2001 | Alessandrini et al. | |
| 6,413,942 | B1 | | 7/2002 | Felgner et al. | |
| 6,451,837 | B1 | | 9/2002 | Baskys | |

OTHER PUBLICATIONS

Krapivinsky et al. 2003. Neuron. 40: 775-784.*
Phillips, A., J Pharm Pharmacology 53: 1169-1174, 2001.*
Luo et al, 1997. Molecular Pharmacology. 51: 79-86.*
Shou et al, 1992. Nature. 358(6384): 351-4.*
Wells (Sep. 18, 1990) "Additivity of Mutational Effects in Proteins." Biochemistry 29(37): 8509-8517.*
Ngo et al. (Mar. 2, 1995) "The Protein Folding Problem and Tertiary Structure Prediction, Chapter 14: Computational Complexity Protein Prediction, and the Levinthal Paradox" pp. 492-495.*
Bork (2000) "Powers and Pitfalls in Sequence Analysis: The 70% Hurdle." Genome Research 10:398-400.*
Skolnick and Fetrow (2000) "From gene to protein structure and function: novel applications of computational approaches in the genomic era." Trends in Biotech. 18(1): 34-39.*
Doercks et al. (Jun. 1998) "Protein annotation: detective work for function prediction." Trends in Genetics 14(6): 248-250.*
Smith and Zhang (Nov. 1997) "The challenges of genome sequence annotation or 'The devil is in the details'." Nature Biotechnology 15:1222-1223.*
Brenner (Apr. 1999) "Errors in genome annotation." Trends in Genetics 15(4): 132-133.*

(Continued)

*Primary Examiner*—Elizabeth C. Kemmerer
*Assistant Examiner*—Zachary C Howard
(74) *Attorney, Agent, or Firm*—Foley Hoag LLP

(57) ABSTRACT

Methods for identifying neuroprotective compounds, as well as compositions and methods for treating subjects suffering from neurological diseases or disorders are provided.

19 Claims, 19 Drawing Sheets

OTHER PUBLICATIONS

Bork and Bairoch (Oct. 1996) "Go hunting in sequence databases but watch out for the traps." Trends in Genetics 12(10): 425-427.*

Hess et al, 1996. J Pharmacol Exp Ther. 278(2): 808-816.*

Abel, T. and Lattal, K.M., "Molecular Mechanisms of Memory Acquisition, Consolidation and Retrieval,"Current Opinion in Neurobiology, 11:180-187 (2001).

Bayer et al., "Interaction with NMDA Receptor Locks CaMKll in an Active Conformation," Nature, 411:801-805 (2001).

Becq et al., "Anatomical and Functional Reconstruction of the Nigrostiatal System In Vitro: Selective Innervation of the Striatum by Dopaminergic Neurons," Journal of Neuroscience Research, 58:553-566 (1999).

Bonni et al., "Cell Survival Promoted by the Ras-MAPK Signaling Pathway by Transcription-Dependent and -Independent Mechanisms," Science, 286:1358-1362 (1999).

Brewer, G.J., "Serum-Free B27/Neurobasal Medium Supports Differentiated Growth of Neurons From the Striatum, Substantia Nigra, Septum, Cerebral Cortex, Cerebellum, and Dentate Gyrus," Journal of Neuroscience Research, 42:674-683 (1995).

Chatterton et al., Excitatory gllycine receptors conatining the NR3 family NMDA receptor subunits, Nature, 415:793-798 (2002).

Cull-Candy et al., "NMDA Receptor Subunits: Diversity, Development and Disease," Current Opinion in Neurobiology, 11:327-335 (2001).

Das et al., "Increased NMDA current and spine density in mice lacking the NMDA receptor subunit NR3A," Nature, 393:377-381 (1998).

Dolmetsch et al., "Signaling to the Nucleus by an L-type Clacium Channel- Calmodulin Complex Through the MAP Kinase Pathway," Science, 294:333-339 (2001).

Farnsworth et al., "Calcium Activation of Ras Mediated by Neuronal Exchange Factor Ras-GRF," Nature, 376(6540):524-527 (1995).

GenBank Accession No. AAD00659 "N-methyl-D-aspartate receptor subunit 2B [*Homo sapiens*]," (Jan. 5, 1999).

GenBank Accession No. CAA47666, "P140 RAS-GRF [*Rattus rattus*]," (Apr. 18, 2005).

GenBank Accession No. NM_002891, "*Homo sapiens*Ras protein-specific guanine nucleotide-releasing factor 1 (RASGRF1), transcript variant 1, mRNA," Jun. 30, 2007).

GenBank Accession No. NP_002882, "Ras protein-specific guanine nucleotide-releasing factor 1 isoform 1 [*Homo sapiens*]" (Jun. 30, 2007).

GenBank Accession No. NM_012574, "*Rattus norvegicus* glutamate receptor, ionotropic, N-methyl D-aspartate 2B (Grin2b), mRNA" (Jul. 30, 2007).

GenBank Accession No. NP_036706, "glutamate receptor, ionotropic, N-methyl D-aspartate 2B [*Rattus norvegicus*]" (Jul. 30, 2007).

GenBank Accession No. NP_722522, "Ras protein-specific guanine nucleotide-releasing factor 1 isoform 2 [*Homo sapiens*]" (Jun. 30, 2007).

GenBank Accession No. U88963, "Human N-methyl-D-aspartate receptor subunit 2B (GRIN2B) mRNA, complete cds" (Jan. 5, 1999).

GenBank Accession No. X67241, "*R. rattus* mRNA for guanine nucelotide releasing factor for RAS P21" (Apr. 18, 2005).

Ghosh, A. and Greenberg, M., "Calcium Signaling in Neurons: Molecular Mechanisms and Cellular Consequences," Science, 268:239-247 (1995).

Gill et al., "Pharmacological Characterization of Ro 63-1908 (1-[2-(4-Hodroxy-phenoxy)-ethyl]-4-(4-methyl benzyl)-piperidin-4-ol), a Novel Subtype-Selective N-Methyl-D-Aspartate Antagonist," J. Pharmacol. Exp. Ther., 302(3):940-948 (2002).

Ginty, D. et al., "Regulation of CREB Phosphorylation in the Suprachiasmatic Nucleus by Light and a Circadian Clock," Science, 260:238-241 (1993).

Hoffman H. et al., "Synaptic Activity-Dependent Developmental Regulation of NMDA Receptor Subunit Expression in Cultured Neocortical Neurons," Journal of Neurochemistry, 75(4):1590-1599 (2000).

Ikonomidou et al., "Blockade of NMDA Receptors and Apoptotic Neurodegeneration in Developing Brain," Science, 283:70-74 (1999).

Kemp et al., "NMDA Receptor Antagonists and Their Potential as Neuroprotective Agents," Handbook of Experimental Pharmacology, (eds. Jonas, P. & Monyer, H., Springer, Berlin) 141:495-527 (1999).

Kemp, J. and McKernan, R., "NMDA receptor pathways as drug targets," Nature Neuroscience Supplement, 5:1039-1042 (2002).

Le, D. and Lipton, S., "Potential and Current Use of N-Methyl-D-Apartate (NMDA) Receptor Antagonists in Diseases of Aging," Drugs and Aging, 18(10):717-724 (2001).

Lees et al., "Glycine anatagonists (gavestinel) in neuroprotection (GAIN International) in patients with acute stroke: a randomised controlled trial," The Lancet, 355:1949-1954 (2000).

Li et al., "Developmental Changes in Localization of NMDA Receptor Subunits in Primary Cultures of Cortical Neurons," European Journal of Neuroscience, 10:1704-1715 (1998).

Martegani et al., "Cloning by functional complementation of a mouse cDNA encoding a homologue of CDC25, a *Saccharomyces cerevisiae* RAS activator," The EMBO Journal, 11(6):2151-2157 (1992).

Medina et al., "Mobilization of intracellular calcium stores participates in the rise of [$Ca^{2+}$]i and the toxic actions of the HIV coat protein GP120," European Journal of Neuroscience, 11:1167-1178 (1999).

Monyer et al., "Developmental and Regional Expression in the Rat Brain and Functional Properties of Four NMDA Receptors," Neuron, 12:529-540 (1994).

Nash, J. and Brotchie, J., "Characterisation of Striatal NMDA Receptors Involved in the Generation of Parkinsonisan Symptoms: Intrastriatal Microinjection Studies in the 6-OHDA-Lesioned Rat," Movement Disorders, 17(3):455-466 (2002).

Payne et al., "Identification of the Regulatory Phosphorylation Sites in pp42/Mitogen-Activated Protein Kinase (MAP Kinase)," The EMBO Journal, 10(4):885-892 (1991).

Platenik et al., "Molecular Mechanisms Associated with Long-Term Consolidation of the NMDA Signals," Life Sciences, 67:335-364 (2000).

Sacco et al., "Glycine Antagonist in Neuroprotection for Patients With Acute Stroke," JAMA, 285(13):1719-1728 (2001).

Sheng et al., "Changing Subunit Composition of Heteromeric NMDA Receptors During Development of Rat Cortex," Nature, 368:144-147 (1994).

Stoppini et al., "A simple method for organotypic cultures of nervous tissue," Journal of Neuroscience Methods, 37:173-182 (1991).

Sweatt, D., "The Neuronal AMP Kinase Cascade: a Biochemical Signal Integration System Subserving Synaptic Plasticity and Memory," J. of Neurochmistry, 76:1-10 (2001).

Tovar, K. and Westbrook, G., "The Incorporation of NMDA Receptors with a Distinct Subunit Composition at Nascent Hippocampal Synapses In Vitro.," The Journal of Neuroscience, 19(10):4180-4188 (1999).

Vanoni et al., "Characterization and Properties of Dominant-negative Mutants of the Ras-Specific Guanine Nucelotide Exhange Factor CDC25$^{Mm}$, "The Journal of Biological Chemistry, 274(51):36656-36662 (1999).

Williams, K., "Ifenprodil Discriminates Subtypes of the N-Methyl-D-Aspartate Receptor: Selectivity and Mechanisms at Recombinant Heteromeric Receptors," Mol. Pharm., 44:851-859.

Xia, Z. et al., "Calcium Influx via the NMDA Receptor Induces Immediate Early Gene Transcription by a MAP Kinase/ERK -Dependent Mechanism," The Journal of Neuroscience, 16(17):5425-5436 (1996).

Zhong et al., "Expression of mRNAs Encoding Subunits of the N-Methyl-D-Aspartate Receptor in Cultured Cortical Neurons," Molecular Pharmacology, 48:846-853 (1994).

* cited by examiner

FIGURE 8
Rat NR2B Subunit
SEQ ID NO: 1

```
   1 gctgaagact ccttaaatat atatatatat atatatattc gggctactaa cctcacatgc
  61 acatgggata atgactctgg attctgcatt gtgagctgct ctccacaccc tgagatcccc
 121 tcttacatta cattttttcc tttgaatttg catctcgtca agacacaaga ttaaaaccaa
 181 atttacacta cactggattt taaatttct tccgttcctt tatcctccgt ctttcttatg
 241 tggatatgca agcgagaaga ggaccctgga tattccaac atgctctctc ccttaatctg
 301 tccgcctaga ggtttggcgt ctacaaacca agagagccga ctagctgaag atgaagccca
 361 gcgcagagtg ctgttccccc aagttctggt tggtgttggc cgtcttgtca gtatcaggca
 421 gcaaagctcg ttcccaaaag agcccccca gcatcggcat cgctgtcatc ctcgtgggca
 481 cttcagacga agtggccata aagacgccc acgagaaaga tgacttccat catctctcag
 541 tagttccccg ggtggagctg gtagccatga acgaaactga cccaaagagc atcatcaccc
 601 gtatctgcga tcttatgtct gaccggaaga tccagggggt ggtgttcgcg gatgacaccg
 661 accaagaagc catcgctcag atcctcgact tcatttctgc tcagactctc acccccatcc
 721 tgggcatcca tggggcatca tctatgataa tggcggataa ggatgagtcc tccatgttct
 781 tccagtttgg cccgtctatc gaacagcaag cttccgtcat gctcaacatc atggaagaat
 841 atgactggta catcttttcc atcgtcacca cctacttccc tggctaccag gactttgtga
 901 acaagatccg cagtaccatc gagaacagct tgtgggctg ggagctcgag gaagtcctcc
 961 tgctagacat gtctctggac gatggcgact ctaagattca gaatcagctg aagaagctcc
1021 aaagccccat cattctcctt tattgcacga aggaggaagc cacctacatt tttgaagtag
1081 ctaactcagt tgggctgact ggctacggct acacgtggat tgtgccgagt ctggtggccg
1141 gggatacgga cacggtgcct tcagagttcc ccacggggct tatctctgtg tcttatgatg
1201 aatgggacta tggccttcct gccagagtga gagatggaat tgccatcatc accactgctg
1261 cctcggacat gctgtccgaa cacagtttca tccctgagcc aagagcagt tgctacaaca
1321 cccacgagaa gaggatctac cagtctaaca tgttgaatag gtatctgatc aatgtcactt
1381 ttgaagggag aaacctgtcc ttcagcgaag atggctacca gatgcatccg aagctggtga
1441 taatccttct gaacaaggag aggaagtggg agagggtggg gaaatggaag gacaagtccc
1501 tgcagatgaa gtattatgtg tggcctcgga tgtgtcctga gactgaggag caagaggatg
1561 accatctgag cattgtcacc ttggaggagg cgccatttgt cattgtggaa agcgtggacc
1621 ctctcagtgg aacctgcatg aggaatacag tcccgtgcca gaagcgcatc atctctgaga
1681 ataaaacaga tgaggaacca ggctacatca aaaatgctg caagggttc tgtattgaca
1741 tccttaagaa aatttctaag tctgtgaagt tcacctatga cctttacctg gtgaccaatg
1801 gcaagcacgg gaagaagatt aatgggacct ggaatggcat gatcggtgag gtggtcatga
1861 agagggccta catggcagtg ggatcactaa ctatcaatga agaacggtca gaggtggttg
1921 acttctctgt acccttcata gaaactggca tcagtgtcat ggtatctcgc agcaatggga
1981 ctgtgtcacc ttctgccttc ttagagccat tcagcgctga cgtgtgggtg atgatgtttg
2041 tgatgctgct cattgtttct gcggtggctg tctttgtctt tgaatacttc agccctgtgg
2101 gttacaacag gtgcctagcc gatggcagag agccaggagg cccatctttc accatcggca
2161 aagcaatttg gttactctgg ggtctggtgt taacaactc cgtacctgtg cagaacccaa
2221 agggaccac ctccaagatc atggtgtcag tgtgggcctt ctttgctgtc attttcctgg
2281 ccagctacac tgccaactta gcagccttca tgatccaaga ggagtatgtg gaccaggttt
2341 ctggcctgag tgacaagaag ttccagagac ctaatgactt ctcacccct ttccgctttg
2401 ggactgtgcc caatggcagc acagagagga atatccgtaa taactatgca gaaatgcatg
2461 cctacatggg aaagttcaac caaggggtg tagatgatgc attgctctcc ctgaaaacag
2521 ggaagcttga tgcattcatc tatgatgcag ctgtgctcaa ctacatggct ggaagggacg
2581 aaggctgcaa actggtgacc attggcagtg gcaaggtctt tgcttctacc ggctatggca
2641 ttgctatcca aaaggactcc gggtggaagc gccaggtgga cctggctatc ctgcagctgt
2701 ttggagatgg ggagatggaa gaactggaag ctctctggct cactggcatt tgccacaatg
2761 agaagaatga ggtgatgagc agccagctgg acatcgacaa tatggcaggt gtcttctata
2821 tgttggggc agccatggcc ctcagcctca tccttcat ctgtgagcat ctgttctatt
2881 ggcagttccg gcattgcttc atgggtgtct gttctggcaa gcctggcatg gtcttctcca
2941 tcagcagagg tatctacagc tgtatccatg gggtagccat agaggagcgc aatccgtga
3001 tgaactcccc cactgccacc atgaacaaca cccactccaa catcctacgc ttgctccgca
3061 cggccaagaa catggccaac ctgtctggag taaacggctc ccctcagagt gccctggact
```

FIGURE 8 con't

```
3121 tcatccgccg agagtcctcc gtctacgaca tctctgagca tcgtcgcagc ttcacgcatt
3181 cagactgcaa gtcttacaat aacccaccct gtgaggaaaa cctgttcagt gactacatta
3241 gcgaggtaga gagaacattt ggtaacctgc agctgaagga cagcaatgtg taccaagacc
3301 actatcacca tcaccaccgg ccacacagca tcggcagcac cagctccatt gatgggctct
3361 atgactgtga caacccaccc ttcaccaccc agcccaggtc aatcagcaag aaaccctgg
3421 acatcggcct gccctcctcc aaacatagcc agctcagcga cctgtatggc aagttctctt
3481 tcaagagtga ccgctacagt ggccacgacg acttgattcg atcggatgtc tccgacatct
3541 ccacgcacac tgtcacctat gggaacatcg agggcaacgc agccaagagg aggaaacagc
3601 agtataagga cagtctaaag aagcggccag cctcggccaa atcgaggagg gagtttgatg
3661 aaatcgagct ggcctaccgt cgccgaccac cccgctcccc ggaccacaag cgctacttca
3721 gggacaaaga agggctccga gacttctacc tggaccagtt ccgaacaaag gagaactcgc
3781 ctcactggga gcacgtggac ttgactgaca tttacaaaga acgcagtgac gacttcaagc
3841 gagattcggt cagtggaggt gggccctgta ccaacaggtc tcacctcaaa cacggaacgg
3901 gcgagaagca cggagtggta ggcggggtgc ctgctccttg ggagaagaac ctgaccaatg
3961 tggattggga ggaccggtct gggggcaact tctgccgcag ctgtccttcc aagctgcaca
4021 attactcctc gacggtggca gggcagaact cgggccggca ggcctgcatc agatgtgagg
4081 cctgtaagaa ggctggtaac ctgtacgaca tcagcaagga caactccctg caggaactgg
4141 accagccggc tgccccgtg gctgtgacat ccaacgcctc cagcaccaag taccctcaaa
4201 gcccgactaa ttccaaggct cagaagaaga atcggaacaa actgcgccgg cagcattcct
4261 acgacacctt cgtggacctg cagaaggagg aggccgcctt ggccccacgc agcgtgagcc
4321 tgaaagacaa gggccgattc atggatggga gccccacgc ccatatgttt gagatgccag
4381 ctggtgagag ctcctttgcc aacaagtcct cagtgcccac tgccggacac caccacaaca
4441 accccggcag cggctacatg ctcagcaagt cgctctaccc tgaccgggtc acgcaaaacc
4501 ctttcatccc cactttgg gatgaccagt gcttgcttca cggcagcaaa tcctacttct
4561 tcaggcagcc cacggtggca ggggcgtcaa aaacaaggcc ggacttccgg gcccttgtca
4621 ccaataagcc agtggtgtca gcccttcatg gggctgtgcc aggtcgtttc cagaaggaca
4681 tttgtatagg gaaccagtcc aacccctgtg tgcctaacaa caaaaacccc agggctttca
4741 atggctccag caatggacat gtttatgaga actttctag tattgagtct gatgtctgag
4801 tgagggaaga gagagaggtt aaggtgggta cggagggat agggctgtgg gccgcgtggt
4861 gcgcatgtca tggaaagagt cggggtgaa cttggctccc attcgctttt tcttcttctt
4921 ttaatttctc tatgggatcc tggagttctg gttccttact gaaggcaacc ctcgtggcca
4981 gcaccatttc tcctccctcg cgcagttctc tccttcccgc atctgtccac cattcctgtt
5041 tccatgagag aatagaacgg ggcctcagtg tgggaggatg gagaggagac caaagcgctg
5101 cctgtgtgct tctttctagc gcagaagggc tcttagcagt tcactttgag cgaggctttc
5161 ctgatgctgc tctctttgtt caggtgagga agcgaaggtg ttctgaggaa ggccattgaa
5221 cctcctgttc ataagagaga agaggctttc actgaattc
```

FIGURE 9
Rat NR2B Subunit
SEQ ID NO: 2

```
   1 mkpsaeccsp kfwlvlavla vsgskarsqk sppsigiavi lvgtsdevai kdahekddfh
  61 hlsvvprvel vamnetdpks iitricdlms drkiqgvvfa ddtdqeaiaq ildfisaqtl
 121 tpilgihggs smimadkdes smffqfgpsi eqqasvmlni meeydwyifs ivttyfpgyq
 181 dfvnkirsti ensfvgwele evllldmsld dgdskiqnql kklqspiill yctkeeatyi
 241 fevansvglt gygytwivps lvagdtdtvp sefptglisv sydewdyglp arvrdgiaii
 301 ttaasdmlse hsfipepkss cynthekriy qsnmlnryli nvtfegrnls fsedgyqmhp
 361 klviillnke rkwervgkwk dkslqmkyyv wprmcpetee qeddhlsivt leeapfvive
 421 svdplsgtcm rntvpcqkri isenktdeep gyikkcckgf cidilkkisk svkftydlyl
 481 vtngkhgkki ngtwnqmige vvmkraymav gsltineers evvdfsvpfi etgisvmvsr
 541 sngtvspsaf lepfsadvwv mmfvmllivs avavfvfeyf spvgynrcla dgrepggpsf
 601 tigkaiwllw glvfnnsvpv qnpkgttski mvsvwaffav iflasytanl aafmiqeeyv
 661 dqvsglsdkk fqrpndfspp frfgtvpngs ternirnnya emhaymgkfn qrgvddalls
 721 lktgkldafi ydaavlnyma grdegcklvt igsgkvfast gygiaiqkds gwkrqvdlai
 781 lqlfgdgeme elealwltgi chneknevms sqldidnmag vfymlgaama lslitficeh
 841 lfywqfrhcf mgvcsgkpgm vfsisrgiys cihgvaieer qsvmnsptat mnnthsnilr
 901 llrtaknman lsgvngspqs aldfirress vydisehrrs fthsdcksyn nppceenlfs
 961 dyiseverlf gnlqlkdsnv yqdhyhhhhr phsigstssi dglydcdnpp fttqprsisk
1021 kpldiglpss khsqlsdlyg kfsfksdrys ghddlirsdv sdisthtvty gniegnaakr
1081 rkqqykdslk krpasaksrr efdeielayr rpprspdhk ryfrdkeglr dfyldqfrtk
1141 ensphwehvd ltdiykersd dfkrdsvsgg gpctnrshlk hgtgekhgvv ggvpapwekn
1201 ltnvdwedrs ggnfcrscps klhnysstva gqnsgrqaci rceackkagn lydiskdnsl
1261 qeldqpaapv avtsnasstk ypqsptnska qkknrnklrr qhsydtfvdl qkeeaalapr
1321 svslkdkgrf mdgspyahmf empagessfa nkssvptagh hhnnpgsgym lskslypdrv
1381 tqnpfiptfg ddqcllhgsk syffrqptva gasktrpdfr alvtnkpvvs alhgavpgrf
1441 qkdicignqs npcvpnnknp rafngssngh vyeklssies dv
```

FIGURE 10
Rat Ras-GRF1
SEQ ID NO: 3

```
   1 ccgacgaggg gcagtcgggt gcctctcgga gatgtttagt gcgtgaggtc tctctggcct
  61 ccaagcacca tgcagaaagc catccgactg aacgatggcc acgtcgtgtc cctgggactg
 121 ctggcccaga gagacggtac gcgcaaaggc tacctgagca agaggagttc ggacaaccca
 181 aaatggcaaa ccaagtggtt tgcgctgctg cagaacctgc tcttctactt cgaaagtgac
 241 tcgagctctc ggccctcggg gctctacctg ctggagggca gtatctgcaa acgcatgccc
 301 tcccccaagc gagggacctc ctccaaggag tccgacaaac agcatcatta cttcacagtg
 361 aacttctcca tgacagcca gaagtccta gagctgagga ccgatgactc caaggactgt
 421 gacgagtggg tggcagcgat tgctcgcgcc agctacaaga tactggccac agagcatgag
 481 gcgctcatgc agaagtacct gcacctgctg caggtggtgg agacagagaa gaccgtggct
 541 aagcagctgc gacagcagct cgaggatggc gaggtcgaga tcgagcgcct gaaggcagag
 601 attgcaaacc tgatcaagga caatgaacgt atccagtcca accagctggt tgccctgag
 661 gatgaggaca gtgacatcaa gaaaattaag aaggtacaga gtttccttcg cggatggctg
 721 tgccggcgaa agtggaagaa catcatccag gactacatcc ggtctcctca tgccgacagc
 781 atgcgcaaga ggaaccaggt ggtgttcagc atgctggaag ctgaggccgc gtacgtgcag
 841 caactacaca tccttgtcaa caattttctg cgcccactgc gcatggccgc cagctcaag
 901 aaaccccta taacacatga cgacgtcagc agtatctttc tgaacagtga gaccatcatg
 961 ttcctgcacc agatcttcta ccaaggcctg aaggcccgta tcgccagctg gcccaccctg
1021 gttctggcgg acctgttcga catcctgctg ccaatgctta acatctacca ggagttcgtc
1081 cgcaaccacc agtacagtct ccagatccta gcacactgca agcaaaaccg ggactttgac
1141 aagctcctca agcagtatga ggccaagcca gactgcgagg agcgcacact ggagaccttc
1201 ctcacctatc caatgttcca gatccccagg tacatcctga cactccatga gctgctggcc
1261 cacacacctc atgagcatgt ggagcgcaac agcctggact atgccaaatc caaactagag
1321 gagctgtcca gggtcatgca cgacgaagtc agtgagaccg agaacatccg caaaaacctg
1381 gccattgagc gtatgatcac cgagggctgt gagatcctcc ttgacaccag ccagaccttt
1441 gtgcgccaag ttccctcat ccaggtgccc atgtcagaaa agggcaagat caacaagggc
1501 cgcctggggt ctctgtccct taagaaagaa ggtgagcgcc agtgtttcct gttctccaag
1561 catctcatca tctgccaccag aggctctggt agcaaactgc acctaaccaa gaatggcgtg
1621 atttccctca ttgactgcac tctactggat gatccagaaa acatggatga tgacggcaaa
1681 ggacaagagg tagatcacct ggactttaag atttgggtgg agccaaagga ttccccaccc
1741 ttcacagtca tcctggtggc ctcatccagg caggagaagg cggcatggac cagtgacatc
1801 atccagtgcg tggataatat ccgctgcaac gggctcatga tgaatgcctt tgaagaaaat
1861 tccaaggtca ccgtgccgca gatgatcaag tctgatgctt ccttatactg tgatgatgtt
1921 gacattcgct tcagcaaaac catgaattct tgcaaagtgc tgcagatccg ctatgccagc
1981 gtggagcgcc tgctggagcg cctgactgat cttcgcttcc tgagtattga ctttctcaac
2041 accttcctgc actcctatcg agtcttcacc gatgctgtgg tggtcctaga caagctgatc
2101 agcatctaca aaaagcccat cactgcgatt cctgccaggt cactggaact cctgttctcc
2161 agtagccaca acaccaaact tctgtacgga gatgccccca gtcgcctcg tgccagccgc
2221 aagttctcct cgccgccgcc cttggccatc ggcacttcgt ccccagtccg ccgccggaag
2281 ttgtctctca acattcccat catcacaggc ggcaaggcgc tggaactggc ttcgctcggg
2341 tgcccctccg acggctacac caacatacac tcgcccatat ctcccttcgg caaaaccacg
2401 ctggacacca gcaagctctg tgtggccagc agcttgacca gacgccgga ggagattgat
2461 atgaccactc tagaggagtc atcaggcttc aggaagccga cctcagacat cttgaaagaa
2521 gagtctgatg atgaccagag tgatgtagac gacacagaag tgtctccacc aacaccgaaa
2581 tcattcagaa acagaatcac tcaagagttc ccactcttta actacaacag tggaatcatg
2641 atgacatgtc gcgatctgat ggacagtaac cgcagccctc tgtcagctac ctctgccttt
2701 gccatagcga ctgcaggagc caatgaaagc cccgcaaaca aggagatata tcgaaggatg
2761 tcttggcca acacagggta ttcctctgac cagagaaata tcgacaaaga gttcgtgatc
2821 cgcagagcgg ccaccaaccg tgtactgaat gtgttgcgcc actgggtcac caagcactcc
2881 caggactttg aaactgacga cctcctcaaa tacaaggtga tctgctttct ggaagaggtc
2941 atgcatgacc cagaccttct accacaagag cgaaaggcag cagccaacat catgaggact
3001 ctgacccagg aagaaataac tgaaaaccat agcatgctgg atgagctctt actaatgacg
```

FIGURE 10 con't

```
3061 gagggtgtga agactgagcc cttcgaaaac cactcagcca tggagatagc agagcagctg
3121 accctgctgg atcaccttgt cttcaagagt attccttatg aggaattctt tggccagggc
3181 tggatgaagg cagataagaa tgaaaggaca ccttacatta tgaaaaccac cagacatttc
3241 aaccatatca gtaacttgat cgcttcagaa attctccgaa acgaggaggt cagtgcaagg
3301 gcaagcacca tcgagaagtg ggtggctgtt gccgacattt gccgctgcct gcacaactac
3361 aatgctgtgc tggagatcac ttcctccatc aaccgcagcg caatcttccg actcaagaag
3421 acatggctca aagtttctaa gcagacgaaa tctctgtttg acaagctcca aaagcttgtg
3481 tcatcagatg gccgatttaa gaacctcaga gaaactttgc gaaattgtga tccaccctgt
3541 gtcccttacc tggggatgta cctgaccgac ttggcattcc tcgaggaagg aacacccaat
3601 tacacagagg acggcctggt caacttctcc aagatgagga tgatctccca tattatccgc
3661 gagattcgcc agtttcagca gactacttac aaaatcgagc cccagccaaa ggtaactcag
3721 tacttagtgg atgaaacctt tgtgttggac gacgaaagtc tgtatgaggc ctccctccga
3781 attgaaccaa aactccccac atga
```

Figure 11
Rat Ras-GRF1
SEQ ID NO: 4

```
   1 mqkairlndg hvvslgllaq rdgtrkgyls krssdnpkwq tkwfallqnl lfyfesdsss
  61 rpsglylleg sickrmpspk rgtsskesdk qhhyftvnfs ndsqkslelr tddskdcdew
 121 vaaiarasyk ilatehealm qkylhllqvv etektvakql rqqledgeve ierlkaeian
 181 likdneriqs nqlvapeded sdikkikkvq sflrgwlcrr kwkniiqdyi rsphadsmrk
 241 rnqvvfsmle aeaeyvqqlh ilvnnflrpl rmaasskkpp ithddvssif lnsetimflh
 301 qifyqglkar iaswptlvla dlfdillpml niyqefvrnh qyslqilahc kqnrdfdkll
 361 kqyeakpdce ertletflty pmfqipryil tlhellahtp hehvernsld yakskleels
 421 rvmhdevset enirknlaie rmitegceil ldtsqtfvrq gsliqvpmse kgkinkgrlg
 481 slslkkeger qcflfskhli ictrgsgskl hltkngvisl idctllddpe nmdddgkgqe
 541 vdhldfkiwv epkdsppftv ilvassrqek aawtsdiiqc vdnircnglm mnafeenskv
 601 tvpqmiksda slycddvdir fsktmnsckv lqiryasver llerltdlrf lsidflntfl
 661 hsyrvftdav vvldklisiy kkpitaipar slellfsssh ntkllygdap ksprasrkfs
 721 sppplaigts spvrrrklsl nipiitggka lelaslgcps dgytnihspi spfgkttldt
 781 sklcvasslt rtpeeidmtt leessgfrkp tsdilkeesd ddqsdvddte vspptpksfr
 841 nritqefplf nynsgimmtc rdlmdsnrsp lsatsafaia taganespan keiyrrmsla
 901 ntgyssdqrn idkefvirra atnrvlnvlr hwvtkhsqdf etddllkykv icfleevmhd
 961 pdllpqerka aanimrtltq eeitenhsml delllmtegv ktepfenhsa meiaeqltll
1021 dhlvfksipy eeffgqgwmk adknertpyi mkttrhfnhi snliaseilr neevsarast
1081 iekwvavadi crclhnynav leitssinrs aifrlkktwl kvskqtkslf dklqklvssd
1141 grfknlretl rncdppcvpy lgmyltdlaf leegtpnyte dglvnfskmr mishiireir
1201 qfqqttykie pqpkvtqylv detfvlddes lyeaslriep klpt
```

Figure 12
Human NR2B
SEQ ID NO: 5

```
   1 taaaacaaaa tttacgctaa attggatttt aaattatctt ccgttcattt atccttcgtc
  61 tttcttatgt ggatatgcaa gcgagaagaa gggactggac attcccaaca tgctcactcc
 121 cttaatctgt ccgtctagag gtttggcttc tacaaaccaa gggagtcgac gagttgaaga
 181 tgaagcccag agcggagtgc tgttctccca agttctggtt ggtgttggcc gtcctggcgg
 241 tgtcaggcag cagagctcgt tctcagaaga gccccccag cattggcatt gctgtcatcc
 301 tcgtgggcac ttccgacgag gtggccatca aggatgccca cgagaaagat gatttccacc
 361 atctctccgt ggtaccccgg gtggaactgg tagccatgaa tgagaccgac ccaaagagca
 421 tcatcacccg catctgtgat ctcatgtctg accggaagat ccaggggggtg gtgtttgctg
 481 atgacacaga ccaggaagcc atcgcccaga tcctcgattt catttcagca cagactctca
 541 cccccatcct gggcatccac gggggctcct ctatgataat ggcagataag gatgaatcct
 601 ccatgttctt ccagtttggc ccatcaattg aacagcaagc ttccgtaatg ctcaacatca
 661 tggaagaata tgactggtac atcttttcta tcgtcaccac ctatttccct ggctaccagg
 721 actttgtaaa caagatccgc agcaccattg agaatagctt tgtgggctgg agctagagg
 781 aggtcctcct actggacatg tccctggacg atggagattc taagatccag aatcagctca
 841 agaaacttca agcccccatc attcttcttt actgtaccaa ggaagaagcc acctacatct
 901 ttgaagtggc caactcagta gggctgactg gctatggcta cacgtggatc gtgcccagtc
 961 tggtggcagg ggatacagac acagtgcctg cggagttccc cactgggctc atctctgtat
1021 catatgatga atgggactat ggcctccccg ccagagtgag agatgaatt gccataatca
1081 ccactgctgc ttctgacatg ctgtctgagc acagcttcat ccctgagccc aaaagcagtt
1141 gttacaacac ccacgagaag agaatctacc agtccaatat gctaaatagg tatctgatca
1201 atgtcacttt tgaggggagg aatttgtcct tcagtgaaga tggctaccag atgcacccga
1261 aactggtgat aattcttctg aacaaggaga ggaagtggga aagggtgggg aagtggaaag
1321 acaagtccct gcagatgaag tactatgtgt ggccccgaat gtgtccagag actgaagagc
1381 aggaggatga ccatctgagc attgtgaccc tggaggaggc accatttgtc attgtggaaa
1441 gtgtggaccc tctgagtgga acctgcatga ggaacacagc cccctgccaa aaacgcatag
1501 tcactgagaa taagacagac gaggagccgg ttacatcaa aaaatgctgc aaggggttct
1561 gtattgacat ccttaagaaa atttctaaat ctgtgaagtt cacctatgac ctttacctgg
1621 ttaccaatgg caagcatggg aagaaaatca tggaacctg gaatggtatg attggagagg
1681 tggtcatgaa gagggcctac atggcagtgg gctcactcac catcaatgag gaacgatcgg
1741 aggtggtcga cttctctgtg cccttcatag agacaggcat cagtgtcatg gtgtcacgca
1801 gcaatgggac tgtctcacct tctgccttct tagagccatt cagcgctgac gtatgggtga
1861 tgatgtttgt gatgctgctc atcgtctcag ccgtggctgt ctttgtcttt gagtacttca
1921 gccctgtggg ttataacagg tgcctcgctg atggcagaga gcctggtgga ccctctttca
1981 ccatcggcaa agctatttgg ttgctctggg gtctggtgtt taacaactcc gtacctgtgc
2041 agaacccaaa ggggaccacc tccaagatca tggtgtcagt gtgggccttc tttgctgtca
2101 tcttcctggc cagctacact gccaacttag ctgccttcat gatccaagag gaatatgtgg
2161 accaggtttc tggcctgagc gacaaaaagt tccagagacc taatgacttc tcaccccctt
2221 tccgctttgg gaccgtgccc aacggcagca gagagaaaa tattcgcaat aactatgcag
2281 aaatgcatgc ctacatggga aagttcaacc agaggggtgt agatgatgca ttgctctccc
2341 tgaaaacagg gaaactggat gccttcatct atgatgcagc agtgctgaac tatatggcag
2401 gcagagatga aggctgcaag ctggtgacca ttggcagtgg aaggtctttt gcttccactg
2461 gctatggcat tgccatccaa aaagattctg ggtggaagcg ccaggtggac cttgctatcc
2521 tgcagctctt tggagatggg gagatggaag aactggaagc tctctggctc actggcattt
2581 gtcacaatga aagaatgag gtcatgagca gccagctgga cattgacaac atggcagggg
2641 tcttctacat gttgggggcg gccatggctc tcagcctcat cctttcatc tgcgaacacc
2701 ttttctattg gcagttccga cattgcttta tgggtgtctg ttctggcaag cctggcatgg
2761 tcttctccat cagcagaggt atctacagct gcatccatgg ggtggcgatc gaggagcgcc
2821 agtctgtaat gaactccccc accgcaacca tgaacaacac acactccaac atcctgcgcc
2881 tgctgcgcac ggccaagaac atggctaacc tgtctggtgt gaatggctca ccgcagagcg
2941 ccctggactt catccgacgg gagtcatccg tctatgacat ctcagagcac cgccgcagct
3001 tcacgcattc tgactgcaaa tcctacaaca acccgccctg tgaggagaac ctcttcagtg
```

FIGURE 12 con't

```
3061 actacatcag tgaggtagag agaacgttcg ggaacctgca gctgaaggac agcaacgtgt
3121 accaagatca ctaccaccat caccaccggc cccatagtat tggcagtgcc agctccatcg
3181 atgggctcta cgactgtgac aacccaccct tcaccaccca gtccaggtcc atcagcaaga
3241 agccctgga catcggcctc ccctcctcca agcacagcca gctcagtgac ctgtacggca
3301 aattctcctt caagagcgac cgctacagtg ccacgacga cttgatccgc tccgatgtct
3361 ctgacatctc aacccacacc gtcacctatg gaacatcga gggcaatgcc gccaagaggc
3421 gtaagcagca atataaggac agcctgaaga agcggcctgc ctcggccaag tcccgcaggg
3481 agtttgacga gatcgagctg gcctaccgtc gccgaccgcc ccgctcccct gaccacaagc
3541 gctacttcag ggacaaggaa gggctacggg acttctacct ggaccagttc cgaacaaagg
3601 agaactcacc ccactgggag cacgtagacc tgaccgacat ctacaaggag cggagtgatg
3661 actttaagcg cgactccgtc agcggaggag ggcctgtac caacaggtcc catatcaagc
3721 acgggacggg cgacaaacac ggcgtggtca gcggggtacc tgcaccttgg gagaagaacc
3781 tgaccaacgt ggagtgggag gaccggtccg gggcaactt ctgccgcagc tgtccctcca
3841 agctgcacaa ctactccacg acggtgacgg gtcagaactc gggcaggcag gcgtgcatcc
3901 ggtgtgaggc ttgcaagaaa gcaggcaacc tgtatgacat cagtgaggac aactccctgc
3961 aggaactgga ccagccggct gccccagtgg cggtgacgtc aaacgcctcc accactaagt
4021 accctcagag cccgactaat tccaaggccc agaagaagaa ccggaacaaa ctgcgccggc
4081 agcactccta cgacaccttc gtggacctgc agaaggaaga agccgccctg ccccgcgca
4141 gcgtaagcct gaaagacaag ggccgattca tggatgggag ccctacgcc cacatgtttg
4201 agatgtcagc tggcgagagc acctttgcca acaacaagtc ctcagtgccc actgccggac
4261 atcaccacca caacaacccc ggcggcgggt acatgctcag caagtcgctc taccctgacc
4321 gggtcacgca aaaccctttc atccccactt ttggggacga ccagtgcttg ctccatggca
4381 gcaaatccta cttcttcagg cagccggtgg tgcgggggc gtcgaaagcc aggccggact
4441 tccgggccct tgtccaccaa aagccggtgg tctcggccct tcatggggcc gtgccagccc
4501 gttccagaa ggacatctgt atagggaacc agtccaaccc ctgtgtgcct aacaacaaaa
4561 accccagggc tttcaatggc tccagcaatg ggcatgttta tgagaaactt tctagtattg
4621 agtctgatgt ctgagtgagg gaacagagag gttaaggtgg gtacgggagg gtaaggctgt
4681 gggtcgcgtg atgcgcatgt cacggagggt gacgggggtg aacttggttc ccatttgctc
4741 ctttcttgtt ttaatttatt tatggggatc ctggagttct ggttcctact gggggcaacc
4801 ctggtgacca gcaccatctc tcctcctttt cacagttctc tccttcttcc ccccgctctc
4861 agccattcct gttcccatga gatgatgcca tgggtctcag caggggaggg tagagcggag
4921 aaaggaaggg cagcatgcgg gcttcctcct ggtgtggaag agctccttga tatcctcttt
4981 gagtgaagct gggagaacca aaaagaggct atgtgagcac aaaggtagct tttcccaaac
5041 tgatcttttc atttaggtga ggaagcaaaa gcatctatgt gagaccattt agcacactgc
5101 ttgtgaaagg aaagaggctc tggctaaatt catgctgctt agatgacatc tgtctaggaa
5161 tcatggtcca agcagaggtt gggaggccat ttgtgtttat atataagcca aaaaatgctt
5221 gcttcaaccc catgagactc gatagtggtg gtgaacagaa caaaaggtca ttggtggcag
5281 agtggattct tgaacaaact ggaaagtacg ttatgatagt gtcccacggt gccttgggga
5341 caagagcagg tggattgtgc gtgcatgtgt gttcatgcac acttgcaccc atgtgtagtc
5401 aggtgcctca agagaaggca accttgactc tttctattgt ttctttcaat atccccaagc
5461 agtgtgattg tttggcttat atacagacag agatggccat gtattacctg aattttggct
5521 gtgtctccct tcatccttct ggaataagga gaatgaaaat tcttgataaa gaagattctg
5581 tggtctaaac aaaaaaggc ggtgagcaat cctgcaagag caaggtacat aaacaagtcc
5641 tcagtggttg gcaactgttt caacttgttt gaaccaagaa ccttccagga aggctaaagg
5701 gaaaccgaat ttcacagcca tgattctttt gcccacactt gggacgaaaa gattctacaa
5761 agctcttttg agcatttaga ctctcgactg gccaaggttt ggggaagaac gaacggacct
5821 ttgaagaagt aaggagtcgt gtatggtagg gtaagtgaga gaggggatg tttcctatgc
5881 tttgatccct tctcacttaa cctgaagcta gacgagcagg cttcttcccc ccaaaactga
5941 ttacaactgc tacagagcag acagttaaga gaaatgagct tgacatttaa gagaaatgag
6001 ctgcactcca tgagtgcagc tctggaggta cgaaaagagg gaagagact tggaaatggg
6061 agacgggggc agagagggac cctccaccac ctctttgggc ctggctgggt gggaatgtga
6121 cttgagccca gagtgaacac tcttggtaga agcccttcta ccttcctgca acacctgttc
6181 cctctcagat tgtaccattg agccggaa
```

FIGURE 13
Human NR2B
SEQ ID NO: 6

```
   1 mkpraeccsp kfwlvlavla vsgsrarsqk sppsigiavi lvgtsdevai kdahekddfh
  61 hlsvvprvel vamnetdpks iitricdlms drkiqgvvfa ddtdqeaiaq ildfisaqtl
 121 tpilgihggs smimadkdes smffqfgpsi eqqasvmlni meeydwyifs ivttyfpgyq
 181 dfvnkirsti ensfvgwele evllldmsld dgdskiqnql kklqspiill yctkeeatyi
 241 fevansvglt gygytwivps lvagdtdtvp aefptglisv sydewdyglp arvrdgiaii
 301 ttaasdmlse hsfipepkss cynthekriy qsnmlnryli nvtfegrnls fsedgyqmhp
 361 klviillnke rkwervgkwk dkslqmkyyv wprmcpetee qeddhlsivt leeapfvive
 421 svdplsgtcm rntapcqkri vtenktdeep gyikkcckgf cidilkkisk svkftydlyl
 481 vtngkhgkki ngtwngmige vvmkraymav gsltineers evvdfsvpfi etgisvmvsr
 541 sngtvspsaf lepfsadvwv mmfvmllivs avavfvfeyf spvgynrcla dgrepgqpsf
 601 tigkaiwllw glvfnnsvpv qnpkgttski mvsvwaffav iflasytanl aafmiqeeyv
 661 dqvsglsdkk fqrpndfspp frfgtvpngs ternirnnya emhaymgkfn qrgvddalls
 721 lktgkldafi ydaavlnyma grdegcklvt igsgkvfast gygiaiqkds gwkrqvdlai
 781 lqlfgdgeme elealwltgi chneknevms sqldidnmag vfymlgaama lslitficeh
 841 lfywqfrhcf mgvcsgkpgm vfsisrgiys cihgvaieer qsvmnsptat mnnthsnilr
 901 llrtaknman lsgvngspqs aldfirress vydisehrrs fthsdcksyn nppceenlfs
 961 dyisevertf gnlqlkdsnv yqdhyhhhhr phsigsassi dglydcdnpp fttqsrsisk
1021 kpldiglpss khsqlsdlyg kfsfksdrys ghddlirsdv sdisthtvty gniegnaakr
1081 rkqqykdslk krpasaksrr efdeielayr rrpprspdhk ryfrdkeglr dfyldqfrtk
1141 ensphwehvd ltdiykersd dfkrdsvsgg gpctnrshik hgtgdkhgvv sgvpapwekn
1201 ltnvewedrs ggnfcrscps klhnysttvt gqnsgrqaci rceackkagn lydisednsl
1261 qeldqpaapv avtsnasttk ypqsptnska qkknrnklrr qhsydtfvdl qkeeaalapr
1321 svslkdkgrf mdgspyahmf emsagestfa nnkssvptag hhhhnnpggg ymlskslypd
1381 rvtqnpfipt fgddqcllhg sksyffrqpt vagaskarpd fralvtnkpv vsalhgavpa
1441 rfqkdicign qsnpcvpnnk nprafngssn ghvyeklssi esdv
```

FIGURE 14
Human Ras-GRF1
SEQ ID NO: 7

```
   1 atgcagaagg ggatccggct gaatgatggc cacgtcgcgt ccctgggact gctggcgcgc
  61 aaggacggca cgcgcaaagg ctacctgagc aagcggagtt cggacaacac aaaatggcaa
 121 accaagtggt tcgcgctgct gcagaacctg ctcttctact tcgagagcga ctcgagctcg
 181 cggccctcgg ggctttacct gctggagggc tgcgtctgcg accgcgcgcc ctcccccaag
 241 ccggcgctgt cggccaagga gccgctggag aaacagcatt acttcacggt gaacttcagc
 301 catgagaacc agaaagcctt ggagctgagg acagaggacg caaaagattg tgacgaatgg
 361 gtggcagcca ttgcacatgc cagctacagg accctcgcca cagagcatga ggcattaatg
 421 cagaaatacc tgcacctgct gcagatcgtg gagacagaga agaccgtggc caagcagctt
 481 cggcagcaga tcgaggatgg ggagatcgag atcgagcggc tgaaggcaga gatcacatcc
 541 ctgctcaagg acaatgagcg catccagtcc acccagactg tcgccccaa cgatgaagac
 601 agcgacatca agaaaattaa gaaggtgcag agcttcctgc ggggctggct gtgccggcgg
 661 aagtggaaga ccatcatcca ggactacatc cggtcacccc atgctgacag catgcgcaag
 721 aggaaccagg tggtgttcag catgctggag gctgaggctg agtacgtgca gcagctgcac
 781 atccttgtca acaatttcct gcgcccgctg cggatggccg ccagctccaa gaagcctccc
 841 atcacacacg acgacgtcag cagcatcttc ctgaacagcg aaaccatcat gttttacat
 901 cagatctttt accaaggcct gaaggcccgc atctccagct ggcccacgct ggtcctggct
 961 gacctatttg acatcctgct gcccatgctc aacatctacc aagagttcgt ccgcaaccac
1021 cagtacagcc tgcagatcct ggcccactgc aagcagaacc gtgacttcga caagctgctg
1081 aagcactacg aggccaagcc tgactgcgag gagaggacgc tggagacctt cctcacctac
1141 cccatgttcc agatccccag gtacatcctg accctccatg agctcctggc ccacacgcct
1201 catgagcacg ttgagcgcaa cagcctggac tacgccaagt ccaaactgga ggagctgtcc
1261 agaataatgc acgatgaagt aagtgagacg gagaacatcc ggaaaaacct ggccatcgag
1321 cgcatgatca tcgaaggctg tgagatcctc ctggacacca gccagacctt tgtgagacaa
1381 ggttccctca ttcaggtgcc catgtctgaa aagggcaaga tcaccagggg gcgcctgggg
1441 tctctctccc taaagaaaga gggcgagcga cagtgcttcc tgttttctaa gcatctgatt
1501 atctgtacca gaggctctgg agggaagctt cacttgacca agaatggagt catatccctc
1561 attgactgca ctttattgga ggagccagaa agcacggagg aggaagccaa aggatccggc
1621 caagacatag atcacttgga ttttaaaatc ggggtggagc caaaggattc cccgcccttt
1681 acagtcatcc tagtggcctc gtccagacag gagaaggcag cgtggaccag tgacatcagc
1741 cagtgtgtgg ataacatccg atgcaatggg ctcatgatga acgcatttga agaaaattcc
1801 aaggtcactg tgccgcagat gatcaagagg accagggagg ggaccaggga agcagaaatg
1861 agcaggtccg acgcctcctt atattgtgat gatgttgaca ttcgcttcag caaaaccatg
1921 aactcctgca aagtgctgca gatccgctac gccagtgtgg agcggctgct ggagaggctg
1981 acggacctgc gcttcctgag catcgacttc ctcaacacct tcctgcactc ctaccgcgtc
2041 ttcaccaccg ccatcgtggt cctggacaag ctcattacca tctacaagaa gcctatcagt
2101 gccattcctg ccaggtggct gaggtcgctg gagctcctgt ttgccagtgg ccagaacaat
2161 aagctcctgt acggtgaacc ccccaagtcc ccgcgcgcca cccgcaagtt ctcctcgccg
2221 ccacctctgt ccatcaccaa gacatcgtca ccgagccgcc ggcggaagct ctccctgaac
2281 atccccatca tcactggcgg caaggccctg gacctggccg ccctcagctg caactccaat
2341 ggctacacca gcatgtactc ggccatgtca ccttcagca aggccacgct ggacaccagc
2401 aagctctatg tgtccagcag cttcaccaac aagattccag atgagggcga tacgacccct
2461 gagaagcccg aagaccttc agcgctcagc aagcagagct cagaagtctc catgagagag
2521 gagtcagata ttgatcaaaa ccagagtgat gatggtgata ctgaaacatc accaactaaa
2581 tctccaacaa cacccaaatc agtcaaaaac aaaattcttc agagttccc actcttttcc
2641 tataacaatg gagtcgtcat gacctcctgt cgtgaactgg acaataaccg cagtgccttg
2701 tcggccgcct ctgcctttgc catagcaacc gccggggcca acgagggcac cccaaacaag
2761 gagaagtacc ggaggatgtc cttagccagt gcagggtttc ccccagacca gaggaatgga
2821 gacaaggagt ttgtgatccg cagagcagcc accaatcgtg tcttgaacgt gctccgccac
2881 tgggtgtcca agcactctca ggactttgag accaacgatg agctcaaatg caaggtgatc
2941 ggcttcctgg aagaagtcat gcacgacccg gagctcctga cccaggagcg aaggctgca
3001 gccaacatca tcaggactct gacccaggag gacccaggtg acaaccagat cacgctggag
```

FIGURE 14 con't

```
3061 gagatcacgc agatggctga aggcgtgaag gctgagccct ttgaaaacca ctcagccctg
3121 gagatcgcgg agcagctgac cctgctagat cacctcgtct tcaagaagat tccttatgag
3181 gagttcttcg gacaaggatg gatgaaactg gaaaagaatg aaaggacccc ttatatcatg
3241 aaaaccacta agcacttcaa tgacatcagt aacttgattg cttcagaaat catccgcaat
3301 gaggacatca acgccagggt gagcgccatc gagaagtggg tggccgtagc tgacatatgc
3361 cgctgcctcc acaactacaa tgccgtactg gagatcacct cgtccatgaa ccgcagtgca
3421 atcttccggc tcaaaaagac gtggctcaaa gtctctaagc agactaaagc tttgattgat
3481 aagctccaaa agcttgtgtc atctgagggc agatttaaga atctcagaga agctctgaaa
3541 aattgtgacc caccctgtgt cccttacctg gggatgtacc tcaccgacct ggccttcatc
3601 gaggagggga cgcccaatta cacggaagac ggcctggtca acttctccaa gatgaggatg
3661 atatcccata ttatccgaga gattcgccag tttcaacaaa ctgcctacaa aatagagcac
3721 caagcaaagg taacgcaata tttactggac caatcttttg taatggatga agaaagcctc
3781 tacgagtctt ctctccgaat agaaccaaaa ctccccacct gaagctgagc ccagcccaga
3841 cccagctgct cccggggaca tgtgctagat gatactgtac atattcgttt ggtttcactg
3901 gattttcttc ttcagtatgt gcttctccaa gaatacaaat cgtccttgtt cttagattcc
3961 tgtagaaccg gaatatgaat ttctgcaccg tttcagactt cgcccaccca tccctcccct
4021 cg
```

FIGURE 15
Human Ras-GRF1
SEQ ID NO: 8

```
   1 mqkgirlndg hvaslgllar kdgtrkgyls krssdntkwq tkwfallqnl lfyfesdsss
  61 rpsglylleg cvcdrapspk palsakeple kqhyftvnfs henqkalelr tedakdcdew
 121 vaaiahasyr tlatehealm qkylhllqiv etektvakql rqqiedgeie ierlkaeits
 181 llkdneriqs tqtvapnded sdikkikkvq sflrgwlcrr kwktiiqdyi rsphadsmrk
 241 rnqvvfsmle aeaeyvqqlh ilvnnflrpl rmaasskkpp ithddvssif lnsetimflh
 301 qifyqglkar isswptlvla dlfdillpml niyqefvrnh qyslqilahc kqnrdfdkll
 361 khyeakpdce ertletflty pmfqipryil tlhellahtp hehvernsld yaskleels
 421 rimhdevset enirknlaie rmiiegceil ldtsqtfvrq gsliqvpmse kgkitrgrlg
 481 slslkkeger qcflfskhli ictrgsggkl hltkngvisl idctlleepe steeeakgsg
 541 qdidhldfki gvepkdsppf tvilvassrq ekaawtsdis qcvdnircng lmmnafeens
 601 kvtvpqmikr tregtreaem srsdaslycd dvdirfsktm nsckvlqiry asverllerl
 661 tdlrflsidf lntflhsyrv fttaivvldk litiykkpis aiparwlrsl ellfasgqnn
 721 kllygeppks pratrkfssp pplsitktss psrrrklsln ipiitggkal dlaalscnsn
 781 gytsmysams pfskatldts klyvsssftn kipdegdttp ekpedpsals kqssevsmre
 841 esdidqnqsd dgdtetsptk spttpksvkn knssefplfs ynngvvmtsc reldnnrsal
 901 saasafaiat aganegtpnk ekyrrmslas agfppdqrng dkefvirraa tnrvlnvlrh
 961 wvskhsqdfe tndelkckvi gfleevmhdp elltqerkaa aniirtltqe dpgdnqitle
1021 eitqmaegvk aepfenhsal eiaeqltlld hlvfkkipye effgqgwmkl eknertpyim
1081 kttkhfndis nliaseiirn edinarvsai ekwvavadic rclhnynavl eitssmnrsa
1141 ifrlkktwlk vskqtkalid klqklvsseg rfknlrealk ncdppcvpyl gmyltdlafi
1201 eegtpnyted glvnfskmrm ishiireirq fqqtaykieh qakvtqylld qsfvmdeesl
1261 yesslriepk lpt
```

NEUROPROTECTIVE THERAPEUTICS PREVENTING ERK/MAPK ACTIVATION THROUGH THE NMDA RECEPTOR

RELATED APPLICATION INFORMATION

This application is a continuation of, and claims priority under 35 U.S.C. § 119 to, International Application No. PCT/US04/01209, filed Jan. 16, 2004, which claims the benefit of priority to U.S. Ser. No. 60/440,679, filed Jan. 17, 2003, all of which applications are incorporated by reference in their entireties.

BACKGROUND

The N-methyl-D-aspartate receptor (NMDAR) plays a part in the induction of apoptotic cell death following cerebral insults. The molecular components of the NMDAR have recently been elucidated. The receptor is a multi-subunit protein composed of individual subunits termed NR1, NR2, and NR3. Furthermore, the NR2 subunit family is further subdivided into NR2A, NR2B, NR2C and NR2D subtypes. Typically, the NMDAR is composed of a combination of these subunits, with NR1 always present along with at least one NR2 subunit and, less often, an NR3 subunit (Das, S., et al., (1998) Nature, 393:377-381; Chatterton, J. E., et al., (2002) Nature, 415:793-798). Each of the subunits confers a slightly different pharmacological profile onto the NMDAR. The existence of multiple subunit subtypes and the molecular heterogeneity of the fully assembled NMDAR paves the way for rational drug design strategies and the development of subunit specific medications for glutamate excitotoxicity (for a review see, Kemp, J. A. and McKeman, R. M., (2002) Nature Neuroscience Supp., 5:1039-1042). However, although such compounds may be subunit selective, some antagonists may affect NMDAR gating and therefore cause unwanted side effects in additional to any beneficial effects that they may have.

To date, clinical trials in stroke and brain injury testing the efficacy of therapeutics that function by blocking NMDA receptors have not been successful (Kemp, J. A., et al., Handbook of Experimental Pharmacology, Vol. 141 (eds. Jonas, P. & Monyer, H.), 495-527 (Springer, Berlin, 1999); Lees, K. R., et al., (2000) Lancet, 355:1949-1954; Sacco, R. L., et al., (2001) JAMA, 285: 1719-1728). Since a properly functioning NMDAR is critical in, among other things, refining synaptic connections, long term potentiation, learning and memory, blockers of the receptor may produce unwanted side-effects. Molecularly, since these drugs block calcium influx, they therefore also inhibit the initiation of a multitude of beneficial cell signaling pathways in addition to the ERK/MPK pathway involved in triggering apoptosis. Clinically multiple different side effects have been observed with NMDAR blockers, including hallucinations, increases in blood pressure, memory disruptions, catatonia and the development of schizophrenia like symptoms.

Subunit specific antagonists alleviate some, but not all, of the above described problems. Given that these antagonists are specific to a particular subunit, side effects are somewhat minimized since only NMDARs carrying that specific subunit are blocked. For example, compounds such as ifenprodil, CP-101606, Ro 25-6981 and Ro 63-1908 are all NR2B specific, but they all function by altering the gating of the NMDAR (Williams, K., (1993) Mol. Pharmacol., 44: 851-859; Kemp, J. A., et al., Handbook of Experimental Pharmacology, Vol. 141 (eds. Jonas, P. & Monyer, H.), 495-527 (Springer, Berlin, 1999); Gill, R., et al., (2002) J. Pharmacol. Exp. Ther., 302: 940-948). Although these antagonists are in some ways superior to non-specific NMDAR blockers, they still elicit unwanted side effects by virtue of blocking calcium influx through the receptor and, therefore, blocking all cell signaling that is independent of the ERK/MAPK cascade.

In addition to antagonists directed at the NMDA receptor, blockers acting at sites upstream to the ERK/MAPK cascade as well as blockers directed at components of the ERK/MAPK cascade are being developed. However, all of these antagonists suffer from the same disadvantage in the sense that all completely block their target resulting in severe side effects that seriously undermine their clinical utility (Ikonomidou C, et al. (1999) Science, January 1;283(5398):70-4).

Glutamate promotes the activation of the NMDAR, which initiates multiple cellular events, including an increase in postsynaptic calcium (Ghosh, A., et al., (1995) Science 268, 239-47) and the activation of the Extracellular Signal—Regulated Kinase (ERK1/2 or ERK/MAPK) pathway (Sweatt, J. D. (2001), J Neurochem 76, 1-10). These events activate multiple transcription factors (Platenik, J., et al., (2000), Life Sci 67, 335-64, West, A. E. et al. (2001), Proc Natl Acad Sci U S A 98, 11024-31) that play a central role in the synaptic plasticity underlying refinement of neuronal connections during development, long-term potentiation, learning, and memory (Platenik, J., et al., (2000), Life Sci 67, 335-64, Abel, T. et al., (2001), Curr Opin Neurobiol, 11, 180-7 (2001)). However, excess concentrations of glutamate and the resultant repetitive stimulation of NMDAR receptor result in toxic concentrations of postsynaptic calcium and the initiation of a lethal cellular cascade that culminates in cell death. Excessive release of glutamate activates NMDA receptors which in turn activates the ERK/MAPK pathway and multiple downstream transcription factors, including Fos, Jun, and Egr, which are known in the art to play a central role in glutamate induced cell death. Thus, the NMDAR-dependent ERK/MAPK pathway might be one of the first elements in a cascade of events leading to neuronal cell death.

Multiple pathological conditions can result in a massive release of glutamate, including cerebral infarcts, head traumas, anoxic insults or seizures of various etiologies, including epilepsy. Additionally, an increase in the release of glutamate is associated with complex neurodegenerative disorders such as Parkinson's disease and Huntington's disease. The role of NMDA receptors in Parkinson's symptoms is well documented (Nash J E. Brotchie J M. (2002) Movement Disorders, 17(3):455-466; Li D. A., Lipton S A., (2001) Drugs & Aging, 18(10):717-724). Cerebral infarcts alone are a major cause of morbidity and mortality with 750,000 cases per year in the United States and 500,000 in Europe. The only currently available treatment for cerebral infarcts is tissue plasminogen activator (TPA), which is only effective if administrated within a few hours of the cerebral insult. Furthermore, while TPA may be effective in minimizing cellular damage by acting on the blood clot causing the damage, it does not in anyway prevent the initiation of the ERK/MAPK signaling cascade which triggers apoptosis. Anoxic insults resulting from cardiac arrest incapacitate as many as 1.5 million people a year and only 10% of those individuals are able to resume active lives following the event. In addition, as many as 30 to 50% of existing epileptic patients require hospitalization due to incapacitating temporal lobe seizures.

Given the devastating consequences of glutamate toxicity, therapeutics capable of preventing glutamate induced cell death, and assays for identifying the same, are needed.

SUMMARY OF THE INVENTION

In one aspect, the invention features peptides which possess the ability to interact with the mammalian RasGRF1 or NR2B proteins or fragments of the RasGRF1 or NR2B proteins. In another aspect, the invention provides a protein complex of RasGRF1 and NR2B, or fragments thereof, or peptides that interact with such a complex. In one embodiment, the invention provides a RasGRF1 binding domain (BD) or an NTR2B BD, or a protein complex comprising RasGRF1, or a fragment thereof, and NR2B, or a fragment thereof. The proteins, fragments and complexes represent drug targets for the prevention and treatment of diseases or disorders related to glutamate excitotoxicity, caused by, for example, cerebral infarcts, head trauma, seizures, and anoxia. In an exemplary embodiment, the invention provides methods for preventing or treating diseases or disorders related to NMDA receptor mediated glutamate excitotoxicity, including for example, cerebral ischemia, Parkinson's disease, Huntington's disease, epilepsy, or neuropathic pain.

In another embodiment, the invention provides a complex comprising: (a) an NR2B polypeptide and a RasGRF1 polypeptide; (b) an NR2B polypeptide and a fragment of a RasGRF1 polypeptide; (c) a fragment of an NR2B polypeptide and a RasGRF1 polypeptide; or (d) a fragment of an NR2B polypeptide and a fragment of a RasGRF1 polypeptide. In another embodiment, the complex may further comprise an NR1 subunit, or a fragment thereof. In another embodiment, the complex may further comprise an antibody, or an antibody fragment, that binds to the complex or a component of the complex. In yet another embodiment, the complex may be isolated and/or purified. In an exemplary embodiment, the complex comprising an NR2B polypeptide and a RasGRF1 polypeptide may be isolated. In yet another embodiment, a complex as described herein may be provided in a composition (including, for example, a reaction mixture, a solution, a cell lysate, etc.) or in a host cell.

In part, the invention provides a RasGRF1 and NR2B protein complex, an isolated polypeptide fragment comprising amino acid residues 886-1310 of NR2B, and an isolated polypeptide fragment comprising amino acid residues 714-913 of RasGRF1, and fragments thereof. Such isolated polypeptide fragments may be produced by a variety of methods, including but not limited to recombinant methods and chemical synthesis. The invention further includes peptidomimetics based on the RasGRF1 or NR2B polypeptide fragments, for example an isolated polypeptide fragment comprising amino acid residues 886-1310 of NR2B or an isolated polypeptide fragment comprising amino acid residues 714-913 of RasGRF1.

In another embodiment this invention provides for antibodies directed to an NR2B polypeptide fragment comprising amino acid residues 886-1310 of NR2B or a RasGRF1 polypeptide fragment comprising amino acid residues 714-913 of RasGRF1. In another embodiment, the present invention provides for an antibody that binds to an interaction site of the RasGRF1 and NR2B protein complex. In still other embodiments, the isolated antibodies of the invention may disrupt or stabilize the RasGRF1 and NPR2B protein complex.

The present invention further provides compositions related to producing and/or expressing the above RasGRF1 and NR2B complexes, NR2B polypeptide fragments, and RasGRF1 polypeptide fragments, such as nucleic acids, vectors, host cells, and the like.

In another embodiment, a method for identifying a compound that modulates Ras-GRF1/NR2B complex mediated glutamate excitotoxicity is provided, comprising:

(i) contacting a RasGRF1/R2B complex with a test compound; and (ii) assessing the extent of said RasGRF1/NR2B complex-mediated glutamate excitotoxicity, wherein a modulation of the activity of said complex indicates that the test compound modulates said RasGRF1/NR2B complex-mediated glutamate excitotoxicity.

Compounds for use with the above-described methods may be include, for example, lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound may be a member of a library of compounds.

The present invention provides for a method of inhibiting NMDA receptor mediated glutamate excitotoxicity comprising disrupting an NR2B/RasGRF1 interaction. In one embodiment the disruption is mediated by a NR2B polypeptide or a fragment thereof. In another embodiment, the NR2B fragment comprises amino acids 886-1310 of NR2B. In yet another embodiment, the disruption is mediated by a RasGRF1 polypeptide or a fragment thereof. In yet another embodiment the RasGRF1 fragment comprises amino acids 714-913 of RasGRF1.

In one aspect the present invention provides for a method for inhibiting NMDA receptor mediated glutamate excitotoxicity in the central nervous system of a subject comprising: providing an expression vector comprising a nucleic acid sequence encoding an NR2B polypeptide; and administering said expression vector under conditions that result in expression of NR2B in the brain, thereby preventing apoptotic and/or necrotic cell death. In one embodiment, the NR2B polypeptide comprises amino acids 886-1310 of NR2B.

In another aspect, the present invention provides for a method for inhibiting NMDA receptor mediated glutamate excitotoxicity in the central nervous system of a subject comprising: providing an expression vector comprising a nucleic acid sequence encoding a RasGRF1 polypeptide; and administering said expression vector under conditions that result in expression of RasGRF1 in the brain, thereby preventing the degeneration of neuronal cells. In one embodiment, the RasGRF1 fragment comprises amino acids 714-913 of RasGRF1.

In yet another aspect, the present invention provides an isolated polypeptide fragment of NR2B which interacts with RasGRF1. In one embodiment, the isolated polypeptide fragment of NR2B comprises amino acid residues 886-1310. In another embodiment, the isolated polypeptide fragment is recombinantly produced. In yet another embodiment, the isolated polypeptide fragment is chemically synthesized.

In yet another aspect, the present invention provides an isolated polypeptide fragment of RasGRF1 which interacts with NR2B. In one embodiment, the isolated RasGRF1 polypeptide comprises amino acid residues 714-913. In another embodiment, the isolated polypeptide fragment is recombinantly produced. In yet another embodiment, the isolated polypeptide fragment is chemically synthesized.

In yet another aspect, the present invention provides peptidomimetics based on the polypeptides provided herein. In one embodiment, a peptidomimetic based on a polypeptide comprising NR2B amino acids 886-1310 is provided. In another embodiment, a peptidomimetic based on a polypeptide comprising RasGRF1 amino acids 714-913 is provided.

In yet another aspect, the present invention provides an isolated complex comprising NR2B/RasGRF1 polypeptides. In one embodiment, the NR2B polypeptide comprises amino acid residues 886-1310 of NR2B and the RasGRF1 polypeptide comprises amino acid residues 714-913 of RasGRF1.

In yet another aspect, the present invention provides a method for identifying a neuroprotective compound that modulates the biological activity of a complex comprising NR2B and RasGRF1, said method comprising: contacting said complex with a test compound; and assaying the activity of said complex, wherein a modulation of said complex in the presence of said test compound indicates that the test compound modulates said complex. In various embodiments, the compound may modulate the formation, stability, and/or activity of said complex and/or the activity of at least one polypeptide contained in said complex.

In yet another aspect, the present invention provides a method of disrupting the NR2B-RasGRF1 complex comprising contacting said complex with a compound capable of disrupting said complex. In one embodiment, the compound is an NR2B fragment or an analog thereof. In another embodiment, the NR2B fragment comprises amino acid residues 886-1310 of NR2B. In yet another embodiment, the compound is a RasGRF1 fragment, or an analog thereof. In yet another embodiment, the RasGRF1 fragment comprises amino acids 714-913 of RasGRF. In yet another embodiment, the compound is selected from the group of compounds consisting of lipids, carbohydrates, polypeptides, peptidomimetics, peptide-nucleic acids (PNAs), small molecules, natural products, aptamers and polynucleotides.

In yet another aspect, the present invention provides a method for treating a subject having a condition characterized by glutamate excitotoxicity comprising: administering to a subject in need of such treatment a NR2B/RasGRF1 complex inhibitor in a therapeutically effective amount. In one embodiment of the method, the NR2B/RasGRF1 complex inhibitor is an NR2B fragment comprising amino acids 886-1310 of NR2B. In another embodiment, the NR2B/RasGRF1 complex inhibitor is a RasGRF fragment comprising amino acids 714-913 of RasGRF1.

The present invention, therefore, makes available novel therapeutics and diagnostics. In one embodiment, the invention provides pharmaceutical compositions comprising compounds identified through the above-described methods that modulate the Ras-GRF1/NR2B complex, Ras-GRF1/NR2B complex-mediated glutamate excitotoxicity, or NMDA receptor mediated glutamate excitotoxicity. In another embodiment, the invention provides methods of treating RasGRF1 and NR2B complex-mediated glutamate excitotoxicity using pharmaceutical compositions.

Other features and advantages of the invention will be apparent from the following detailed description, and from the claims.

DESCRIPTION OF THE DRAWINGS

FIG. 8 shows SEQ ID NO: 1, the nucleic acid sequence of rat NR2B subunit (SEQ ID NO:1). GenBank Accession No: NM_012574.

FIG. 9 shows SEQ ID NO: 2, the amino acid sequence of rat NR2B subunit (SEQ ID NO: 2) GenBank Accession No: NP_036706.

FIG. 10 shows SEQ ID NO: 3, the nucleic acid sequence of rat Ras-GRF1 (SEQ ID NO:3). GenBank Accession No: X67241.

FIG. 11 shows SEQ ID NO: 4, the amino acid sequence of rat Ras-GRF1 (SEQ ID NO: 4) GenBank Accession No: CAA47666.

FIG. 12 shows SEQ ID NO: 5, the nucleic acid sequence of human NR2B subunit (SEQ ID NO:5). GenBank Accession No: U88963.

FIG. 13 shows SEQ ID NO: 6, the amino acid sequence of human NR2B subunit (SEQ ID NO: 6) GenBank Accession No: AAD00659.

FIG. 14 shows SEQ ID NO: 7, the nucleic acid sequence of human Ras-GRF1 (SEQ ID NO:7). GenBank Accession No: NM_002891.

FIG. 15 shows SEQ ID NO: 8, the amino acid sequence of human Ras-GRF1 (SEQ ID NO: 8) GenBank Accession No: NP_002882.

DETAILED DESCRIPTION

Definitions

Figure 1:
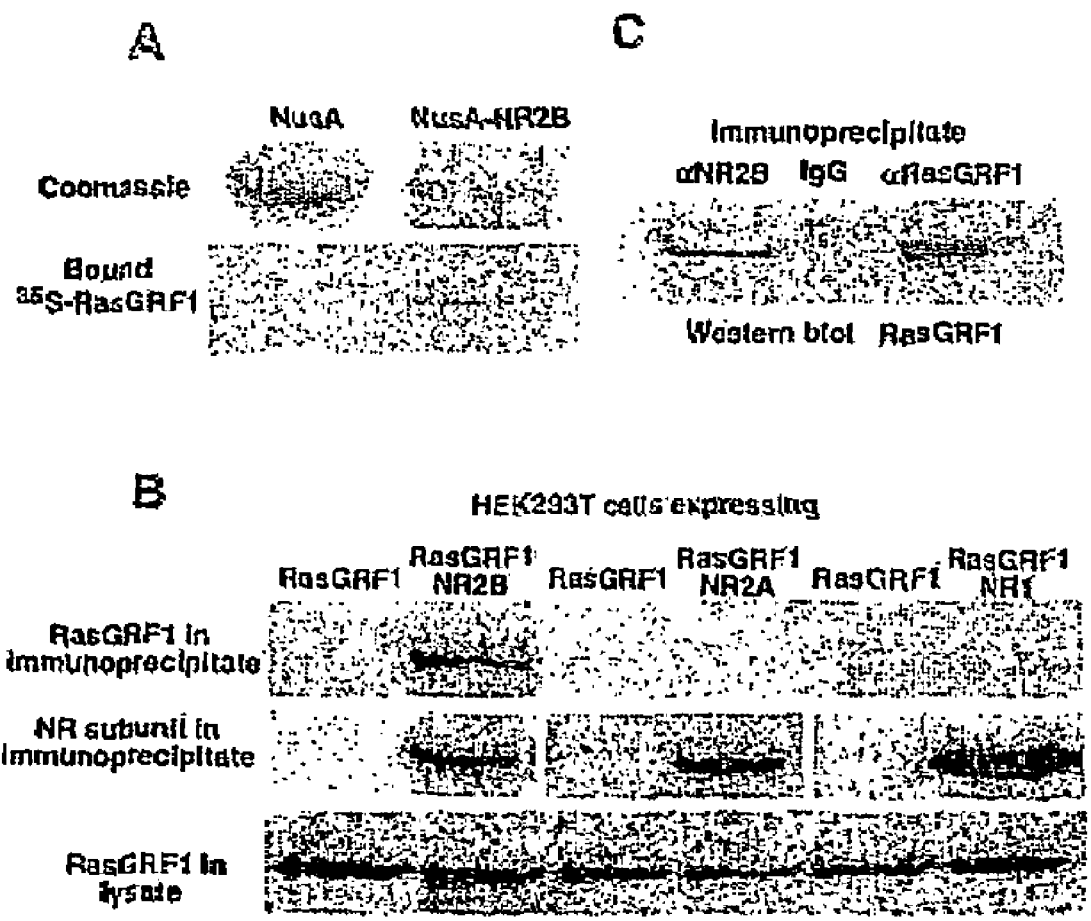
FIG. 1 shows gels of co-immunoprecipitions/pull-down assays with radiolabeled proteins indicating that NR2B and RasGRF1 Interact in vitro and in vivo. (A) A purified 6His-NusA-NR2B (886-1310) fusion protein specifically precipitated in vitro translated RasGRF1. (B) Interaction of RasGRF1 and NMDA subunits co-expressed in HEK293T cells. (C) RasGRF1 and NR2B co-immunoprecipitated from rat brain microsomes.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

"Activity" or "biological activity" or "bioactivity" or "biological function", which are used interchangeably, refer to an effector or antigenic function that is directly or indirectly performed by a polypeptide (whether in its native or denatured conformation), or by any subsequence thereof. Biological activities include, but are not limited to, binding to polypeptides, binding to other proteins or molecules, activity as a DNA binding protein, as a transcription regulator, ability to bind damaged DNA, enzymatic activity, methyl transferase activity, phosphorylase or kinase activity, conformational changes, changes in intracellular localization, changes in the transcription level of the gene encoding the peptide, changes in second messenger levels, etc. An activity may be modulated by directly affecting the subject polypeptide. Alternatively, a bioactivity may be altered by modulating the level of the polypeptide, such as by modulating expression of the corresponding gene.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

Tile term "complex" refers to an association between at least two moieties (e.g. chemical or biochemical) that have an affinity for one another. "Protein complex" or "polypeptide complex" refers to a complex comprising at least one polypeptide. In one embodiment, a complex comprises NR2B and Ras-GRF1. In another embodiment, a complex comprises a fragment of NR2B and/or RasGRF1. In an exemplary embodiment, a complex comprises a fragment of NR2B having amino acid residues 886-1310 of NR2B and/or a fragment of Ras-GRF1 having amino acid residues 714-913 of RasGRF1.

A "coding sequence" refers to a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence may be included downstream of (e.g., 3' to) the coding sequence.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

An "effective amount" is an amount sufficient to effect beneficial or desired results. An effective amount can be administered in one or more administrations, applications or dosages.

A "gene" refers to a polynucleotide containing at least one open reading frame encoding a polypeptide. A gene may include intron sequences in addition to exon sequences.

"Host cell" refers to a cell transduced with a specified transfer vector. The cell is optionally selected from in vitro cells such as those derived from cell culture, ex vivo cells, such as those derived from an organism, and in vivo cells, such as those in an organism. "Host cells" or "recombinant host cells" or "heterologous cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein."

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated complex", with reference to a complex of polypeptides, refers to a complex which (1) comprises at least polypeptide prepared from recombinant DNA or RNA, or of synthetic origin, or some combination thereof, (2) is not associated with other proteins that it is normally found with in nature, (3) is isolated from the cell in which it normally occurs, (4) is isolated free of other proteins from the same cellular source, (5) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity, protein-protein interaction, or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators may be screened at one time. The activity of a modulator may be known, unknown or partially known.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "NR2B binding domain" or "NR2B-BD" refers to a region on an NR2B polypeptide that is capable of interacting with a Ras-GRF1 polypeptide, or fragment thereof. In an exemplary embodiment, the term NR2B-BD refers to a region comprising amino acids 886-1310 of NR2B (e.g., SEQ ID NO: 2 or 6).

The term "NR2B/RasGRF1 complex polypeptide" refers to a polypeptide that may be found in a complex comprising NR2B and RasGRF1. In one embodiment, the term NR2B/RasGRF1 complex includes NR2B polypeptides, and fragments thereof, and RasGRF1 polypeptides, and fragments thereof, as described further herein. In another embodiment, the term NR2B/RasGRF1 complex polypeptide may encompass other polypeptides that can bind to an NR2B/RasGRF1 complex, such as, for example, an NR1 subunit or an antibody.

The term "NR2B nucleic acid" refers to a nucleic acid encoding a NR2B polypeptide, e.g., a nucleic acid comprising a sequence consisting of, or consisting essentially of, the polynucleotide sequence set forth in SEQ ID NO: 1 or SEQ ID NO: 5. A nucleic acid of the invention may comprise all, or a portion of: the nucleotide sequence of SEQ ID NO: 1 or SEQ ID NO: 5; a nucleotide sequence at least 60%, 70%, 80%, 90%, 95%, 96%, 97%, 98% or 99% identical to SEQ ID NO: 1 or SEQ ID NO: 5; a nucleotide sequence that hybridizes under stringent conditions to SEQ ID NO: 1 or SEQ ID NO: 5; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous with an amino acid sequence of SEQ ID NO: 2 or SEQ ID NO: 6; nucleotide sequences encoding polypeptides having an activity of a polypeptide of the invention and having at least about 60%, 70%, 80%, 85%, 90%, 95%, 98%, 99% homology or more with SEQ ID NO: 2 or SEQ ID NO: 6; nucleotide sequences that differ by 1 to about 2, 3, 5, 7, 10, 15, 20, 30, 50, 75 or more nucleotide substitutions, additions or deletions, such as allelic variants, of SEQ ID NO: 1 or SEQ ID NO: 5; nucleic acids derived from and evolutionarily related to SEQ ID NO: 1 or SEQ ID NO: 5; and complements of, and nucleotide sequences resulting from the degeneracy of the genetic code, for all of the foregoing and other nucleic acids of the invention. Nucleic acids of the invention also include homologs, e.g., orthologs and paralogs, of SEQ ID NO: 1 or SEQ ID NO: 5 and also variants of SEQ ID NO: 1 or SEQ ID NO: 5 which have been codon optimized for expression in a particular organism (e.g., host cell).

The term "NR2B polypeptide" refers to polypeptides having the amino acid sequence set forth in SEQ ID NO: 2 or SEQ ID NO: 6 and functional equivalents thereof. In certain embodiments, a NR2B polypeptide refers to homologues, orthologues, paralogues, allelic variants, and alternative splice forms of SEQ ID NO: 2 or SEQ ID NO: 6 that retain at least one biologically activity of SEQ ID NO: 2 or SEQ ID NO: 6. In other embodiments, NR2B polypeptides include polypeptides comprising all or a portion of the amino acid sequence set forth in SEQ ID NO: 2; the amino acid sequence set forth in SEQ ID NO: 2 or SEQ ID NO: 6 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to SEQ ID NO: 2 or SEQ ID NO: 6; and functional fragments thereof.

The term "Ras-GRF1 binding domain" or "Ras-GRF1-BD" refers to a region on a Ras-GRF1 polypeptide that is capable of interacting with a NR23 polypeptide, or fragment thereof. In an exemplary embodiment, the term Ras-GRF1-BD refers to a region comprising amino acids 714-913 of SEQ ID NO: 4 or amino acids 732-942 of SEQ ID NO: 8.

The term "Ras-GRF1 nucleic acid" refers to a nucleic acid encoding a Ras-GRF1 polypeptide, e.g., a nucleic acid comprising a sequence consisting of, or consisting essentially of, the polynucleotide sequence set forth in SEQ ID NO: 3 or SEQ ID NO: 7. A nucleic acid of the invention may comprise all, or a portion of: the nucleotide sequence of SEQ ID NO: 3 or SEQ ID NO: 7; a nucleotide sequence at least 60%, 70%, 80%, 90%, 95%, 96%, 97%, 98% or 99% identical to SEQ ID NO: 3 or SEQ ID NO: 7; a nucleotide sequence that hybridizes under stringent conditions to SEQ ID NO: 3 or SEQ ID NO: 7; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous with an amino acid sequence of SEQ ID NO: 4 or SEQ ID NO: 8; nucleotide sequences encoding polypeptides having an activity of a polypeptide of the invention and having at least about 60%, 70%, 80%, 85%, 90%, 95%, 98%, 99% homology or more with SEQ ID NO: 4 or SEQ ID NO: 8; nucleotide sequences that differ by 1 to about 2, 3, 5, 7, 10, 15, 20, 30, 50, 75 or more nucleotide substitutions, additions or deletions, such as allelic variants, of SEQ ID NO: 3 or SEQ ID NO: 7; nucleic acids derived from and evolutionarily related to SEQ ID NO: 3 or SEQ ID NO: 7; and complements of, and nucleotide sequences resulting from the degeneracy of the genetic code, for all of the foregoing and other nucleic acids of the invention. Nucleic acids of the invention also include homologs, e.g., orthologs and paralogs, of SEQ ID NO: 3 or SEQ ID NO: 7 and also variants of SEQ ID NO: 3 or SEQ ID NO: 7 which have been codon optimized for expression in a particular organism (e.g., host cell).

The term "Ras-GRF1 polypeptide" refers to polypeptides having the amino acid sequence set forth in SEQ ID NO: 4 or SEQ ID NO: 8 and functional equivalents thereof. In certain embodiments, a Ras-GRF1 polypeptide refers to homologues, orthologues, paralogues, allelic variants, and alternative splice forms of SEQ ID NO: 4 or SEQ ID NO: 8 that retain at least one biologically activity of SEQ ID NO: 4 or SEQ ID NO: 8. In other embodiments, Ras-GRF1 polypeptides include polypeptides comprising all or a portion of the amino acid sequence set forth in SEQ ID NO: 4 or SEQ ID NO: 8; the amino acid sequence set forth in SEQ ID NO: 4 or SEQ ID NO: 8 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to SEQ ID NO: 4 or SEQ ID NO: 8; and functional fragments thereof.

The terms "protein", "polypeptide" and "peptide" are used interchangeably herein when referring to a gene product.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions which promote specific hybrizidation between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: Td=(((((3×#GC)+(2×#AT))×37)−562)/#bp)−5; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10× Denhardt (0.2% Ficoll, 0.2% Polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989),6.3.1-12.3.6; Sambrook et al., 1989, Molecular Cloning, A Laboratory Manual, Cold Spring Harbor Press, N.Y; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, New York;

and Tibanyenda, N. et al., Eur. J. Biochem. 139:19 (1984) and Ebel, S. et al., Biochem. 31:12083 (1992).

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 75% percent of all species present in the composition, more than about 80%, 85%, 90%, 95%, 98%, 99% or more of all species present. The object species may be purified to essential homogeneity (contaminant species cannot be detected in the composition by conventional detection methods) wherein the composition consists essentially of a single species. A skilled artisan may purify a polypeptide or complex of the invention using standard techniques for protein purification in light of the teachings herein. Purity of a polypeptide or complex may be determined by a number of methods known to those of skill in the art, including for example, amino-terminal amino acid sequence analysis, gel electrophoresis, and/or mass-spectrometry analysis.

A "peptide nucleic acid" or "PNA" refers to an analogue of a nucleic acid in which the backbone of the molecule is not sugar-phosphate, but rather a peptide or peptidomimetic. A detailed description of PNAs may be found in Nielsen, et al. *Curr. Issues Mol. Biol.* (1999) 1:89-104.

"Peptidomimetic" refers to a compound containing peptide-like structural elements that is capable of mimicking the biological action(s) of a natural parent polypeptide.

"Pharmaceutically-acceptable salts" refers to the relatively non-toxic, inorganic and organic acid addition salts of compounds.

"Pharmaceutically acceptable carrier" refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

"Protein", "polypeptide" and "peptide" are used interchangeably herein when referring to a gene product, e.g., as may be encoded by a coding sequence. By "gene product" it is meant a molecule that is produced as a result of transcription of a gene. Gene products include RNA molecules transcribed from a gene, as well as proteins translated from such transcripts.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties. In an exemplary embodiment the fragment comprises a binding domain. In one exemplary embodiment a Ras-GRF1 fragment is able to form a complex with an NR2B polypeptide, or a fragment thereof. In another embodiment an NR2B fragment is able to form a complex with a Ras-GRF1 polypeptide, or a fragment thereof.

"Recombinant protein", "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "test compound" refers to a molecule to be tested by one or more screening method(s) as a putative modulator of a polypeptide of the invention or other biological entity or process. A test compound is usually not known to bind to a target of interest. The term "test compound" is meant to include polypeptides, polynucleotides, carbohydrates, lipids, and small molecules, or mixtures thereof.

The term "treating" as used herein is intended to encompass curing as well as ameliorating at least one symptom of the condition or disease.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. Exemplary vectors, include, for example, plasmid, phage, transposon, cosmid, chromosome, virus, and virion.

General Background

The disclosed invention is based, at least in part, on the discovery that amino acids 886-1310 of the NR2B subunit of the NN4DAR directly interacts with amino acids 714-913 of the calcium sensitive Ras activator, Ras-GRF1 and the further finding that this interaction is critical for signal transduction from the NMDAR to the ERK/MAPK cascade.

Additionally, the present invention teaches that this interaction can be specifically disrupted by the addition of exogenous NR2B-BD or exogenous Ras-GRF1-BD to the native complex. The disruption of the activation of ERK/MAPK is specific and does not interfere with NMDAR activation of alternative signaling cascades, such as the CREB gene transcription pathway. Furthermore, the disruption of ERK/MAPK activation by either the NR2B-BD or the Ras-GRF1-BD does not interfere with alternative mechanisms of ERK/MAPK activation, which do not lead to the initiation of the apoptotic cascade, specifically ERK/MAPK activation via L-type calcium channels or the BDNF-mediated pathway. In some cases, activation of the ERK/MAPK cascade promotes desirable cellular changes, however, abnormal or unwanted activation of NMDAR by glutamate may lead the activation of the ERK/MAPK cascade to culminate in apoptotic (e.g., nuclear condensation and fragmentation) and/or necrotic (e.g., cytoplasmic membrane permeability) cell death. As described herein, inhibition of the ERK/MAPK signal transduction pathway by fragments of NR2B or Ras-GRF1 may be highly specific and highly effective. The discovery of the ERK/MAPK complex permits the design of novel neuroprotective therapeutics that may not interfere with other NMDA mediated signaling pathways or the desirable activation of the ERK/MAPK cascade via alternative cellular mechanisms.

The peptides disclosed herein are highly specific blockers of the NMDAR dependent ERK/MAPK pathway activation. The peptides disclosed herein have several advantages to the above-described strategies, as they do not indiscriminately block the NMDAR or the ERK/MAPK pathway. Rather, the peptides disclosed herein specifically affect the interaction between the receptor and the cellular cascade and therefore only affect the pathway that mediates glutamate-induced excitotoxicity.

Nucleic Acids & Polypeptides of the Invention

The present invention contemplates polypeptide complexes, defined as "NR2B/Ras-GRF1" complexes comprising (a) a full length NR2B polypeptide and a full length Ras-GRF1 polypeptide, (b) a full length NR2B polypeptide and a fragment of Ras-GRF1, (c) a full length Ras-GRF1 polypeptide and a fragment of NR2B, or (d) a fragment of NR2B and a fragment of Ras-GRF1.

The present invention makes available in a variety of embodiments soluble, purified and/or isolated forms of the NR2B/Ras-GRF1 complexes or the NR2B/Ras-GRF1 complex polypeptides.

In one aspect, an NR2B/Ras-GRF1 complex polypeptide may comprise (a) a full-length NR2B complex polypeptide amino acid sequence, (b) a full-length NR2B/Ras-GRF1 complex polypeptide amino acid sequence with 1 to about 20 conservative amino acid substitutions, (c) a polypeptide amino acid sequence that is at least 80% identical to an NR2B/Ras-GRF1 complex polypeptide sequence of interest or (d) a fragment of the an NR2B/Ras-GRF1 complex polypeptide of interest. In another aspect, the present invention contemplates a composition comprising an isolated NR2B/Ras-GRF1 complex or NR2B/Ras-GRF1 complex polypeptide and less than about 25%, or alternatively 15%, or alternatively 5%, contaminating biological macromolecules or polypeptides. In an exemplary embodiment, the NR2B fragment comprises amino acids 886-1310 of NR2B. In another embodiment, the Ras-GRF1 fragment comprises amino acids 714-913 of Ras-GRF1. In still another embodiment, the Ras-GRF1 fragment comprises amino acids 886-1219 of Ras-GRF1. In yet another embodiment, the Ras-GRF1 fragment comprises amino acids 1219-1310.

The present invention further provides compositions related to producing, detecting, or characterizing a NR2B/Ras-GRF1 complex, an NR2B polypeptide or fragment thereof, or a Ras-GRF1 polypeptide or fragment thereof, such as nucleic acids, vectors, host cells, and the like. Such compositions may serve as compounds that modulate a NR2B/Ras-GRF1 complex, an NR2B polypeptide or fragment thereof, or a Ras-GRF1 polypeptide or fragment thereof, such as antisense nucleic acids.

In certain embodiments, a NR2B/Ras-GRF1 complex polypeptide of the invention may be a fusion protein containing a domain which increases its solubility and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a NR2B/Ras-GRF1 complex polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, provided are fusions between NR2B and RasGRF1 polypeptides, and nucleotide sequences encoding the fusion polypeptides. The fusion polypeptides may comprise all or a part of an NR2B polypeptide and all or a part of a RasGRF1 polypeptide. In one embodiment, the fusion proteins may optionally contain a linker sequence between the NR2B and the RasGRF1 sequences. In another embodiment, the fusion protines may contain a protease cleavage site between the NR2B and the RasGRF1 sequences (as described further above). In an exemplary embodiment, the fusion proteins will be capable of carrying out at least one biological activity of an NR2B/RasGRF1 complex and may be useful for identifying a modulator of the activity and/or formation of an NR2B/RasGRF1 complex. The fusion proteins may optionally contain other heterologous sequences such as polypeptide tags or labels. In certain embodiments, the fusion proteins may be formed by chemically or enzymatically linking two separate sequences together or may be formed by expressing or synthesizing a single polypeptide sequence comprising both NR2B and RasGRF1 sequences.

In an exemplary embodiment, a fusion protein comprises amino acid residues 886-1310 of NR2B and amino acid residues 714-913 of RasGRF1.

In still another embodiment, a NR2B/RasGRF1 complex polypeptide of the invention may be labeled with a fluorescent label to facilitate their detection, purification, or structural characterization. In an exemplary embodiment, a NR2B/RasGRF1 complex polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention relates to the use of an isolated nucleic acid in "antisense" therapy. As used herein, antisense therapy refers to administration or in situ generation of oligonucleotide probes or their derivatives which specifically hybridize (e.g. binds) under cellular conditions with the cellular mRNA and/or genomic DNA encoding one of the subject NR2B/Ras-GRF1 complexe polypeptides so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy that relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a member of a NR2B/Ras-GRF1 complex, including, for example, an NR2B polypeptide or fragment thereof and/or a Ras-GRF1 polypeptide or fragment thereof. Alternatively, the antisense construct is an oligonucleotide probe which is generated ex vivo and which, when introduced into the cell causes inhibition of expression by hybridizing with the mRNA and/or genomic sequences encoding a member of a NR2/Ras-GRF1 complex, including, for example, an NR2B polypeptide or fragment thereof and/or a Ras-GRF1 polypeptide or fragment thereof. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958-976; and Stein et al., (1988) *Cancer Res* 48:2659-2668.

In a further aspect, the invention provides double stranded small interfering RNAs (siRNAs), and methods for administering the same. siRNAs decrease or block gene expression. While not wishing to be bound by theory, it is generally thought that siRNAs inhibit gene expression by mediating sequence specific mRNA degradation. RNA interference (RNAi) is the process of sequence-specific, post-transcriptional gene silencing, particularly in animals and plants, initiated by double-stranded RNA (dsRNA) that is homologous in sequence to the silenced gene (Elbashir et al. Nature 2001; 411(6836): 494-8). Accordingly, it is understood that siRNAs and long dsRNAs may be used to inhibit the expression of a nucleic acid encoding a member of a NR2B/Ras-GRF1 complex, including, for example, an NR2B polypeptide or fragment thereof and/or a Ras-GRF1 polypeptide or fragment thereof, and particularly when the polynucleotide is expressed in a mammalian or plant cell.

In another aspect of the invention, the subject nucleic acid is provided in an expression vector comprising a nucleotide sequence encoding one or more members of a NR2B/Ras-GRF1 complex, including, for example, an NR2B polypeptide or fragment thereof and/or a Ras-GRF1 polypeptide or fragment thereof, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

This invention pertains to a host cell transfected with a recombinant gene in order to express one or more members of a NR2B/Ras-GRF1 complex, including, for example, an NR2B polypeptide or fragment thereof and/or a Ras-GRF1 polypeptide or fragment thereof. The host cell may be any prokaryotic or eukaryotic cell. For example, an NR2B polypeptide or fragment thereof and/or a Ras-GRF1 polypeptide or fragment thereof may be expressed in bacterial cells, such as *E. coli*, insect cells (baculovirus), yeast, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide will be known to those in the art.

A cell culture includes host cells, media and other byproducts. Suitable media for cell culture are well known in the art. A NR2B/Ras-GRF1 complex, an NR2B polypeptide or fragment thereof, and/or a Ras-GRF1 polypeptide or fragment thereof, may be secreted and isolated from a mixture of cells and medium containing the polypeptide. Alternatively, NR2B/Ras-GRF1 complex, an NR2B polypeptide or fragment thereof, and/or a Ras-GRF1 polypeptide or fragment thereof, may be retained cytoplasmically and the cells harvested, lysed and the protein or protein complex isolated. A NR2B/Ras-GRF1 complex, an NR2B polypeptide or fragment thereof, and/or a Ras-GRF1 polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of NR2B, Ras-GRF1 or a complex thereof. In one embodiment, the components of a NR2B/Ras-GRF1 complex may be purified separately and then mixed together to form a complex. In another embodiment, the NR2B/Ras-GRF1 may be purified from a source (e.g., a host cell, composition, cell lysate, etc.) comprising both NR2B and Ras-GRF polypeptide or fragments thereof.

Thus, a nucleotide sequence encoding all or a selected portion of an NR2B polypeptide and/or a Ras-GRF1 polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant NR2B/Ras-GRF1 complex polypeptides by microbial means or tissue-culture technology in accord with the subject invention.

Expression vehicles for production of a recombinant protein include plasmids and other vectors. For instance, suitable vectors for the expression of an NR2B/Ras-GRF1 complex polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the NR2B/Ras-GRF1 complex, or NR2B/Ras-GRF1 complex polypeptide, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

It is also possible to modify the structure of NR2B/Ras-GRF1 complex polypeptide for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

In certain embodiments, it may be advantageous to provide naturally-occurring or experimentally-derived homologs of a NR2B/RasGRF1 complex polypeptide. Such homologs may function in a limited capacity as a modulator to promote or inhibit a subset of the biological activities of the naturally-occurring form of the polypeptide (including for example, formation and/or activity of an NR2B/RasGRF1 comples). Thus, specific biological effects may be elicited by treatment with a homolog of limited function, and with fewer side effects relative to treatment with agonists or antagonists which are directed to all of the biological activities of a NR2B/RasGRF1 complex, or complex polypeptide. For instance, antagonistic homologs may be generated which interfere with the ability of the wild-type polypeptide of the invention to associate with certain proteins, but which do not substantially interfere with the formation of complexes between the native polypeptide and other cellular proteins.

Another aspect of the invention relates to NR2B/RasGRF1 complex polypeptides derived from the full-length NR2B/RasGRF1 complex polypeptides as described herein. Isolated peptidyl portions of the subject NR2B/RasGRF1 complex polypeptides may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, NR2B/RasGRF1 complex polypeptides may be arbitrarily divided into fragments of desired length with no overlap of the fragments, or may be divided into overlapping fragments of a desired length. The fragments may be produced (recombinantly or by chemical synthesis) and tested to identify those peptidyl fragments having a desired property, for example, the capability of functioning as a modulator of the polypeptides of the invention. In an illustrative embodiment, peptidyl portions of an NR2B/RasGRF1 complex polypeptide may be tested for binding activity, as well as inhibitory ability, by expression as, for example, thioredoxin fusion proteins, each of which contains a discrete fragment of a protein of the invention (see, for example, U.S. Pat. Nos. 5,270,181 and 5,292,646; and PCT publication WO94/02502).

This invention further contemplates a method of generating sets of combinatorial mutants of NR2B/RasGRF1 complex polypeptides, as well as truncation mutants, and is especially useful for identifying potential variant sequences (e.g. homologs). The purpose of screening such combinatorial libraries is to generate, for example, homologs which may modulate the activity of a NR2B/RasGRF1 complex, or complex polypeptide, or alternatively, which possess novel activities altogether. Combinatorially-derived homologs may be generated which have a selective potency relative to a naturally-occurring protein. Such homologs may be used in the development of therapeutics.

Likewise, mutagenesis may give rise to homologs which have intracellular half-lives dramatically different than the corresponding wild-type protein. For example, the altered protein may be rendered either more stable or less stable to proteolytic degradation or other cellular process which result in destruction of, or otherwise inactivation of the protein. Such homologs, and the genes which encode them, may be utilized to alter protein expression by modulating the half-life of the protein. As above, such proteins may be used for the development of therapeutics or treatment.

In similar fashion, NR2B/RasGRF1 complex polypeptide homologs may be generated by the present combinatorial approach to act as antagonists, in that they are able to interfere with the activity of the corresponding wild-type protein, or with the formation and or activity of an NR2B/RasGRF1 complex.

In a representative embodiment of this method, the amino acid sequences for a population of protein homologs are aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential protein sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. A G Walton, Amsterdam: Elsevier pp. 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *PNAS USA* 89:2429-2433; Devlin et al., (1990) *Science* 249: 404-406; Cwirla et al., (1990) *PNAS USA* 87: 6378-6382; as well as U.S. Pat. Nos. 5,223,409, 5,198,346, and 5,096,815).

Alternatively, other forms of mutagenesis may be utilized to generate a combinatorial library. For example, protein homologs (both agonist and antagonist forms) may be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137: 109-118; Grodberg et al., (1993) *Eur. J. Biochem.* 218:597-601; Nagashima et al., (1993) *J. Biol. Chem.* 268:2888-2892; Lowman et al., (1991) *Biochemistry* 30:10832-10838; and Cunningham et al., (1989) *Science* 244:1081-1085), by linker scanning mutagenesis (Gustin et al., (1993) *Virology* 193: 653-660; Brown et al., (1992) *Mol. Cell Biol.* 12:2644-2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11-19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying truncated forms of proteins that are bioactive.

A wide range of techniques are known in the art for screening gene products of combinatorial libraries made by point mutations and truncations, and for screening cDNA libraries for gene products having a certain property. Such techniques will be generally adaptable for rapid screening of the gene libraries generated by the combinatorial mutagenesis of protein homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high throughput analysis as necessary to screen large numbers of degenerate sequences created by combinatorial mutagenesis techniques.

In an illustrative embodiment of a screening assay, candidate combinatorial gene products are displayed on the surface of a cell and the ability of particular cells or viral particles to bind to the combinatorial gene product is detected in a "panning assay". For instance, the gene library may be cloned into the gene for a surface membrane protein of a bacterial cell (Ladner et al., WO 88/06630; Fuchs et al., (1991) *Bio/Technology* 9:1370-1371; and Goward et al., (1992) *TIBS* 18: 136-140), and the resulting fusion protein detected by panning, e.g. using a fluorescently labeled molecule which binds the cell surface protein, e.g. FITC-substrate, to score for potentially functional homologs. Cells may be visually inspected and separated under a fluorescence microscope, or, when the morphology of the cell permits, separated by a fluorescence-activated cell sorter. This method may be used to identify substrates or other polypeptides that can interact with a NR2B/RasGRF1 complex polypeptide of the invention.

In similar fashion, the gene library may be expressed as a fusion protein on the surface of a viral particle. For instance, in the filamentous phage system, foreign peptide sequences may be expressed on the surface of infectious phage, thereby conferring two benefits. First, because these phage may be applied to affinity matrices at very high concentrations, a large number of phage may be screened at one time. Second, because each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVIII coat proteins may be used to generate fusion proteins without disrupting the ultimate packaging of the viral particle (Ladner et al., PCT publication WO 90/02909; Garrard et al., PCT publication WO 92/09690; Marks et al., (1992) *J. Biol. Chem.* 267:16007-16010; Griffiths et al., (1993) *EMBO J.* 12:725-734; Clackson et al., (1991) *Nature* 352:624-628; and Barbas et al., (1992) *PNAS USA* 89:4457-4461). Other phage coat proteins may be used as appropriate.

The invention also provides for reduction of an NR2B/Ras-GRF1 complex polypeptide to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a protein which participates in a protein-protein interaction with another protein. To illustrate, the critical residues of a protein which are involved in molecular recognition of a substrate protein may be determined and used to generate peptidomimetics that may bind to the substrate protein. The peptidomimetic may then be used as an inhibitor of the wild-type protein by binding to the substrate and covering up the critical residues needed for interaction with the wild-type protein, thereby preventing interaction of the protein and the substrate. By employing, for example, scanning mutagenesis to map the amino acid residues of a protein which are involved in binding a substrate polypeptide, peptidomimetic compounds may be generated which mimic those residues in binding to the substrate. For instance, non-hydrolyzable peptide analogs of such residues may be generated using benzodiazepine (e.g., see Freidinger et al., in *Peptides: Chemistry and Biology,* G. R. Marshall ed., ESCOM Publisher: Leiden, Netherlands, 1988), azepine (e.g., see Huffman et al., in *Peptides: Chemistry and Biology,* G. R. Marshall ed., ESCOM Publisher: Leiden, Netherlands, 1988), substituted gama lactam rings (Garvey et al., in *Peptides: Chemistry and Biology,* G. R. Marshall ed., ESCOM Publisher: Leiden, Netherlands, 1988), keto-methylene pseudopeptides (Ewenson et al., (1986) *J. Med. Chem.* 29:295; and Ewenson et al., in *Peptides: Structure and Function* (Proceedings of the 9th American Peptide Symposium) Pierce Chemical Co. Rockland, Ill., 1985), β-turn dipeptide cores (Nagai et al., (1985) *Tetrahedron Lett* 26:647; and Sato et al., (1986) *J Chem Soc Perkin Trans* 1:1231), and β-aminoalcohols (Gordon et al., (1985) *Biochem Biophys Res Commun* 126:419; and Dann et al., (1986) *Biochem Biophys Res Commun* 134:71).

Nucleic acids encoding a NR2B/Ras-GRF1 complex polypeptide may be obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

General procedures for PCR are taught in MacPherson et al., PCR: A PRACTICAL APPROACH, (IRL Press at Oxford University Press, (1991)). PCR conditions for a given reaction may be empirically determined by one of ordinary skill in the art based on the teachings herein. A number of parameters influence the success of a reaction. Among these parameters are annealing temperature and time, extension time, $Mg^{++}$ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

Another method for obtaining polynucleotides is by enzymatic digestion. For example, nucleotide sequences can be generated by digestion of appropriate vectors with suitable recognition restriction enzymes. The resulting fragments can then be ligated together as appropriate.

The polynucleotides used in the present invention may also be produced in part or in total by chemical synthesis, e.g., by the phosphoramidite method described by Beaucage and Carruthers, Tetra. Letts., 22:1859-1862 (1981) or the triester method according to the method described by Matteucci et al., J. Am. Chem. Soc., 103:3185 (1981), and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

Antibodies A variety of antibodies directed to NR2B/Ras-GRF1 complexes, NR2B polypeptides or fragments thereof, or Ras-GRF1 polypeptides or fragment thereof, are also provided. In one embodiment, the present invention provides an isolated antibody that has a higher binding affinity for an NR2B/Ras-GRF1 complex than for the any of the components of the complex alone, including an NR2B polypeptide or fragment thereof, or a Ras-GRF1 polypeptide or fragment thereof. In an exemplary embodiment, an antibody, or antibody fragment may be capable of binding to a NR2B/Ras-GRF1 complex with less than 80%, 70%, 60%, 50%, 40%, 30%, 25%, 20%, 15%, 10%, 5%, 3%, 2%, 1%, or less cross-reactivity with a component of the complex when not in the complex. In another embodiment, the invention provides an isolated antibody that binds to an interaction site on an NR2B/Ras-GRF1 complex polypeptide (for example, a site on an NR2B polypeptide or fragment thereof that is capable of interacting with a Ras-GRF1 polypeptide or fragment thereof, or a site on a Ras-GRF1 polypeptide or fragment thereof that is capable of interacting with an NR2B polypeptide or fragment thereof). In still other embodiments, the isolated antibodies of the invention may disrupt or stabilize an NR2B/Ras-GRF1 complex. In an exemplary embodiment, the present invention contemplates an isolated antibody that binds to an NR2B polypeptide comprising amino acid residues 886-1310 of NR2B. In another embodiment, the present invention contemplates an isolated antibody that binds to a Ras-GRF1 polypeptide comprising amino acid residues 714-913 of Ras-GRF1.

Antibodies may be elicited by methods known in the art. For example, a mammal such as a mouse, a hamster or rabbit may be immunized with an immunogenic form of a NR2B/Ras-GRF1 complex, an NR2B polypeptide or fragment thereof, and/or a Ras-GRF1 polypeptide or fragment thereof, as described herein (e.g., an antigenic fragment which is capable of eliciting an antibody response). Alternatively, immunization may occur by using a nucleic acid which presumably produces in vivo expression of an NR2B/Ras-GRF1 complex, or an NR2B/Ras-GRF1 complex polypeptide, giving rise to the immunogenic response observed. Techniques for conferring immunogenicity on a protein or peptide include conjugation to carriers or other techniques are well known in the art. For instance, a peptidyl portion of an NR2B/Ras-GRF1 complex, or an NR2B/Ras-GRF1 complex polypeptide, may be administered in the presence of adjuvant. The progress of immunization may be monitored by detection of antibody titers in plasma or serum. Standard ELISA or other immunoassays may be used with the immunogen as antigen to assess the levels of antibodies.

Following immunization, antisera reactive with an NR2B/Ras-GRF1 complex, or an NR2B/Ras-GRF1 complex polypeptide, may be obtained and, if desired, polyclonal antibodies isolated from the serum. To produce monoclonal antibodies, antibody-producing cells (lymphocytes) may be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495-497), as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77-96). Hybridoma cells can be screened immunochemically for production of antibodies specifically reactive with an NR2B/Ras-GRF1 complex, or an NR2B/Ras-GRF1 complex polypeptide, and the monoclonal antibodies isolated.

Antibodies directed against an NR2B/Ras-GRF1 complex, or an NR2B/Ras-GRF1 complex polypeptide, can be used to selectively block the action of an NR2B/Ras-GRF1 complex or an NR2B/Ras-GRF1 complex polypeptide. Antibodies may be employed to isolate or to identify clones expressing the polypeptides to purify the polypeptides by affinity chromatography.

Identification of Compounds that Modulate a NR2B/Ras-GRF1 Complex

The NR2B/Ras-GRF1 complexes and/or NR2B/Ras-GRF1 complex polypeptides described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In another aspect, modulators, inhibitors, or antagonists against the polypeptides of the invention, biological complexes containing them, or orthologues thereto, may be used to treat any disease or other treatable condition of a patient (including humans and animals), including, for example, apoptotic and/or necrotic cell death caused by NMDA receptor mediated glutamate exitotoxicity. Disease or disorders that may be treated or prevented using the methods and compositions described herein, include, for example, stroke, head trauma, seizures, anoxia, cerebral ischemia, Parkinson's disease, Huntington's disease, epilepsy, and/or neuropathic pain.

Modulators of NR2B/Ras-GRF1 complexes, other structurally related molecules, and NR2B/Ras-GRF1 complex polypeptides, may be identified and developed as set forth below and otherwise using techniques and methods known to those of skill in the art. The modulators of the invention may be employed, for instance, to inhibit and treat NR2B/Ras-GRF1-mediated and/or NMDA receptor mediated diseases or disorders. The modulators of the invention may elicit a change in one or more of the following activities: (a) a change in the level and/or rate of formation of an NR2B/Ras-GRF1 complex, (b) a change in the activity of an NR2B/Ras-GRF1 complex, (c) a change in the stability of an NR2B/Ras-GRF1 complex, (d) a change in the conformation of an NR2B/Ras-GRF1 complex, or (e) a change in the activity of at least one polypeptide contained in an NR2B/Ras-GRF1 complex. A number of methods for identifying a molecule which modulates a NR2B/Ras-GRF1 complex, or an NR2B/Ras-GRF1 complex polypeptide, are known in the art. For example, in one such method, a NR2B/Ras-GRF1 complex, or an NR2B/Ras-GRF1 complex polypeptide, is contacted with a test compound, and the activity of the NR2B/Ras-GRF1 complex, or an NR2B/Ras-GRF1 complex polypeptide, in the presence of the test compound is determined, wherein a change in the activity of the NR2B/Ras-GRF1 complex, or an NR2B/Ras-GRF1 complex polypeptide, in the presence of the compound as compared to the activity in the absence of the compound (or in the presence of a control compound) is indicative that the test compound modulates the activity of the NR2B/Ras-GRF1 complex, or an NR2B/Ras-GRF1 complex polypeptide.

Compounds to be tested for their ability to act as modulators of NR2B/Ras-GRF1 complexes, or NR2B/Ras-GRF1 complex polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises an NR2B/Ras-GRF1 complex polypeptide. In an exemplary embodiment, the compound comprises amino acid residues 886-1310 or NR2B or amino acid residues 714-913 or Ras-GRF1.

A variety of assay formats will suffice and, in light of the present disclosure, those not expressly described herein may nevertheless be comprehended by one of ordinary skill in the art based on the teachings herein. Assay formats for analyzing NR2B/Ras-GRF1 complex formation, NR2B/Ras-GRF1 complex activity, and/or activity of an NR2B/Ras-GRF1 complex polypeptide, may be generated in many different forms, and include assays based on cell-free systems, e.g. purified proteins or cell lysates, as well as cell-based assays which utilize intact cells. Simple binding assays can also be used to detect agents which modulate a NR2B/Ras-GRF1 complex, for example, by disrupting the formation of an NR2B/Ras-GRF1 complex, by inhibiting the binding of an NR2B/Ras-GRF1 complex to a substrate, and/or by inhibiting the binding of an NR2B/Ras-GRF1 complex polypeptide to a substrate. Another example of an assay useful for identifying a modulator of an NR2B/Ras-GRF1 complex is a competitive assay that combines one or more NR2B/Ras-GRF1 complex polypeptides with a potential modulator, such as, for example, polypeptides, nucleic acids, natural substrates or ligands, or substrate or ligand mimetics, under appropriate conditions for a competitive inhibition assay. NR2B/Ras-GRF1 complex polypeptides can be labeled, such as by radioactivity or a colorimetric compound, such that NR2B/Ras-GRF1 complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting NR2B/Ras-GRF1 complexes, or complex polypeptides, as described above.

Complex formation between a Ras-GRF1 polypeptide or a NR2B polypeptide and a binding partner may be detected by a variety of methods. Modulation of the formation of Ras-GRF1/NR2B complexes may be quantified using, for example, detectably labeled proteins such as radiolabeled, fluorescently labeled, or enzymatically labeled polypeptides or binding partners, by immunoassay, or by chromatographic detection. Methods of isolating and identifying Ras-GRF1/NR2B complexes described above may be incorporated into the detection methods.

In certain embodiments, it may be desirable to immobilize a Ras-GRF1 and/or NR2B polypeptide to facilitate separation of Ras-GRF1 and/or NR2B complexes from uncomplexed forms of one or both of the proteins, as well as to accommodate automation of the assay. Binding of an Ras-GRF1 and/or NR2B polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of Ras-GRF1 and/or NR2B polypeptides found in the bead fraction quantified from the gel using standard electrophoretic techniques such as described in the appended examples.

Other techniques for immobilizing proteins on matrices are also available for use in the subject assay. For instance, either a Ras-GRF1 and/or NR2B polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the Ras-GRF1 and/or NR2B polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of Ras-GRF1 and/or NR2B polypeptide trapped in the NR2B/Ras-GRF1 complex may be assessed with a chromogenic substrate of the enzyme, e.g. 3,3'-diamino-benzadine terahydrochloride or 4-chloro-1-napthol. Likewise, a fusion protein comprising the Ras-GRF1 and/or NR2B polypeptide and glutathione-S-transferase may be provided, and Ras-GRF1 and/or NR2B complex formation quantified by detecting the GST activity using 1-chloro-2,4-dinitrobenzene (Habig et al (1974) J Biol Chem 249:7130).

For processes that rely on immunodetection for quantitating one of the Ras-GRF1 and/or NR2B complex polypeptides trapped in the Ras-GRF1 and/or NM2B complex, antibodies against the Ras-GRF1 and/or NR2B complex polypeptide, such as anti-polypeptide antibodies, may be used. Alternatively, the Ras-GRF1 and/or NR2B polypeptide to be detected in the Ras-GRF1 and/or NR2B complex may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, an Ras-GRF1 and/or NR2B complex polypeptide may be used to generate an two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a DNA-binding domain of a transcriptional activator may be fused in frame to the coding sequence for a "bait" protein, e.g., a Ras-GRF1 and/or NR2B polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a DNA-binding domain that recognizes the responsive element on the reporter gene in the host cell, and (b) a bait protein (e.g., a Ras-GRF1 and/or NR2B polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA-binding domain of the first hybrid protein and the transcriptional activation domain of the second hybrid protein may be derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, $\lambda$cI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the NR2B/Ras-GRF1 complex, or complex polypeptide, of interest may be generated in whole cells, taking advantage of cell culture techniques to support the subject assay. For example, the NR2B/Ras-GRF1 complex, or complex polypeptide, may be constituted in a prokaryotic or eukaryotic cell culture system. Advantages to generating the NR2B/Ras-GRF1 complex, or complex polypeptide, in an intact cell includes the ability to screen for modulators of the level and/or activity of the NR2B/Ras-GRF1 complex, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The NR2B/Ras-GRF1 complexes and NR2B/Ras-GRF1 complex polypeptides can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of NR2B/Ras-GRF1 complexes may be detected in a cell-free assay generated by constitution of a functional NR2B/Ras-GRF1 complex in a cell lysate. In an alternate format, the assay can be derived as a reconstituted protein mixture which, as described below, offers a number of benefits over lysate-based assays.

The activity of an NR2B/Ras-GRF1 complex or an NR2B/Ras-GRF1 complex polypeptide may be identified and/or assayed using a variety of methods well known to the skilled artisan. For example, the activity of an NR2B/Ras-GRF1 complex or NR2B/Ras-GRF1 complex polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of an NR2B/Ras-GRF1 complex, or NR2B/RasGRF1 complex polypeptide, may be assessed by monitoring changes in the phenotype of a targeted cell. For example, the detection means can include a reporter gene construct which includes a transcriptional regulatory element that is dependent in some form on the level and/or activity of an NR2B/Ras-GRF1 complex, or NR2B/RasGRF1 complex polypeptide. The NR2B/Ras-GRF1 complex, or NR2B/RasGRF1 complex polypeptide, may be provided as a fusion protein with a domain that binds to a DNA element of a reporter gene construct. The added domain of the fusion protein can be one which, through its DNA-binding ability, increases or decreases transcription of the reporter gene. Which ever the case may be, its presence in the fusion protein renders it responsive to an NR2B/Ras-GRF1 complex, or NR2B/RasGRF1 complex polypeptide. Accordingly, the level of expression of the reporter gene will vary with the level of expression of an NR2B/Ras-GRF1 complex, or NR2B/RasGRF1 complex polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of an NR2B/Ras-GRF1 complex, or NR2B/RasGRF1 complex polypeptide, present in the cell. Such embodiments of the subject assay are particularly amenable to high through-put analysis in that proliferation of the cell can provide a simple measure of inhibition of the NR2B/Ras-GRF1 complex, or NR2B/Ras-GRF1 complex polypeptide.

Methods of Delivery

Any means for the introduction of polynucleotides or nucleic acids into mammals, human or non-human, may be adapted to the practice of this invention for the delivery of the various constructs of the invention into the intended recipient.

Gene Therapy

Gene delivery vehicles useful in the practice of the present invention can be constructed, utilizing methodologies of molecular biology, virology, microbiology, molecular biology and recombinant DNA techniques, by one of skill in the art based on the teaching herein.

In other embodiments, viral vectors, including viral vectors suitable for modifying neural cells, may be used in accordance with the invention (see, e.g., Viral Vectors: Gene Therapy and Neuroscience Applications Ed. Kaplitt and Loewy, Academic Press, San Diego, Calif., (1995)). A transgene may be incorporated into any of a variety of viral vectors useful in gene therapy, such as recombinant retroviruses, adenovirus, adeno-associated virus (AAV), and herpes simplex virus-1. While various viral vectors may be used in the practice of this invention, AAV- and adenovirus-based approaches are of particular interest. Typically, viral vectors carrying transgenes are assembled from polynucleotides encoding the transgene(s), suitable regulatory elements and elements necessary for production of viral proteins which mediate cell transduction. In an exemplary embodiment, adeno-associated viral (AAV) vectors are employed.

In one embodiment of the invention, the DNA constructs are delivered using an expression vector. The expression vector may be a viral vector or a liposome that harbors the polynucleotide. Nonlimiting examples of viral vectors useful according to this aspect of the invention include lentivirus vectors, herpes simplex virus vectors, adenovirus vectors, adeno-associated virus vectors, various suitable retroviral vectors, pseudorabies virus vectors, alpha-herpes virus vectors, HIV-derived vectors, other neurotropic viral vectors and the like. The following additional guidance on the choice and use of viral vectors may be helpful to the practitioner. As described in greater detail below, such embodiments of the subject expression constructs are specifically contemplated for use in various in vivo and ex vivo gene therapy protocols. In another embodiment of the invention, the DNA constructs are delivered to cells by transfection, i.e., by delivery of "naked" DNA or in a complex with a colloidal dispersion system.

In vivo gene transfer provides another method for the direct delivery of therapeutic nucleic acids. There are several different gene delivery vehicles available for in vivo gene therapy. The methods include, but are not limited to, herpes simplex viral vectors (Federoff, H. J., et al., (1992), Proc. Natl. Acad. Sci USA 89:1636-1640; Geller, A. I., et al., (1988), Science 241:1667-1669; Geller, A. I, et al., (1990), Proc. Natl. Acad. Sci USA 87:1149-1153), adenoviral vectors (Caillaud, C., et al., (1993), Eur. J. Neurosci. 5:1287-1291; Chase, T. N., et al., (1987), Adv,. Neurol. 45:477-480) lentiviral vectors (Naldini, L., (1996), Science 727:263-267), adeno-associated vectors (Muzyczka N., (1992) Immunol. 158:97-129; Samulski, R. J., et al., (1983), J. Virol. 63:3822-3828) and the transfer of naked DNA (Acsadi, G., et al., (1991), New Biol. 3:71-81; Jiao, S., et al., (1992), Hum. Gene Ther. 3:21-33; Wolff, J. A., et al., (1990), Science 247:1465-1468).

The polynucleotides of the invention may be operably linked to one or more transcriptional and translational regulation elements for injection as naked DNA into a subject. Schwartz et al., have demonstrated a successful transfer of naked DNA into the neuronal cells of the adult mouse (Schwartz, B., et al., (1996), Gene Ther 3:405-411). Additionally, Wolff et al., have succeeded in the transducing muscle cells following the injection of naked DNA into muscle.(Wu, P., et al., (1996), Gene Ther 3:246-253). In an exemplary embodiment, the polynucleotide of the invention and necessary regulatory elements are present in a plasmid or vector. Thus, the polynucleotide of the invention may be DNA, which is itself non-replicating, but is inserted into a plasmid, which may further comprise a replicator. The DNA may be a sequence engineered so as not to integrate into the host cell genome.

Multiple delivery approaches have been shown to be effective in the context of adenovirus delivery to the CNS. Methods include, but are not limited to, parenchymal delivery, intraventricular delivery and perivascular delivery (see Table I in Davidson et al., (1997) Exp. Neurol. 144: 125-130). Most often, intraparenchymal, intravitreal, subretinal, or ventricular injections have been used to effectively target the viral vector to the area of interest (Akli, S., et al., (1993), Nat. Genet. 3:224-228; Bajocchi, G., et al., (1993), Nat. Genet 3:229-234; Davidson, B. L., et al., (1993), Nat. Genet. 3:219-223; Davidson, B. L., et al., (1994), Exp. Neurol. 125: 258-267; Le Gal La Salle, G., et al., (1993), Science 259: 988-990; Li, t., et al., (1994), Invest. Ophthalmol. Visual Sci. 35: 2543-2549; Li, T., and G. L. Davidson, (1995), Proc. Natl. Acad. Sci USA 92: 7700-7704; Plumb, T. J., et al., (1996), Neurosci. Lett. 214:159-162). Individuals skilled in the art with recognize that the methods described may be readily adapted to other viral vectors including retroviral vectors and adeno-associated vectors.

Methods of delivery of viral vectors include, but are not limited to, intra-arterial, intra-muscular, intravenous, intranasal and oral routes. In an exemplary embodiment, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

When a NR2B/Ras-GRF1 complex polypeptide according to the invention is to be administered to a mammal directly, this may be accomplished via the direct injection of a vector including the polynucleotide, or an alternative delivery device, at a preselected target location in the brain of the mammal (see e.g., Kordower et al., (1998) Mov. Disorders 13:383-393; Freed et al., (1992) N.E.J. Med. 327:1549-1555; and Widner et al., (1992) N.E.J. Med 327:1556-1563. Preferably, the patient to be treated is placed in a stereotaxis frame to pinpoint the target site in the brain for injection (for a discussion of the method see Paxinos, The Rat Brain Stereotaxic Coordinates, 512.sup.nd Ed. Academic Press, San Diego, Calif., (1987)). In an exemplary embodiment of the invention the preselected target location is a site in the mammal's substantia nigra. Following identification of a suitable site of injection to reach the preselected target location, a solution containing the polynucleotide of the invention is injected at a controlled rate. Control of the rate of injection is effected using methods known in the art (e.g., see Mandel et al., (1998) J. Neurosci. 18:4271-4284).

Pharmaceutical compositions will comprise sufficient genetic material to produce a therapeutically effective amount of the NR2B/Ras-GRF1 complex, or complex polypeptide, of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which can be added may be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

Naked DNA & Liposomes

Any means for the introduction of polynucleotides into mammals, human or non-human, may be adapted to the practice of this invention for the delivery of the various constructs of the invention into the intended recipient. In one embodiment of the invention, the NR2B/Ras-GRF1 complex polypeptide constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. An exemplary colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995)). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al. Colloidal dispersion systems.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject.

In certain instances, a polynucleotide construct may permit translation for a limited period of time or in a time specific fashion so that the polypeptide delivery is transitory. This can be achieved, e.g., by the use of an inducible promoter.

Pharmaceutical Composition

Pharmaceutical compositions of the invention include any modulator identified according to the present invention, or a pharmaceutically acceptable salt thereof, and a pharmaceutically acceptable carrier, adjuvant, or vehicle. In an exemplary embodiment, pharmaceutical compositions of the invention include modulators of a NR2B/RasGRF1 complex, or a NR2B/RasGRF1 complex polypeptide. The term "pharmaceutically acceptable carrier" refers to a carrier(s) that is "acceptable" in the sense of being compatible with the other ingredients of a composition and not deleterious to the recipient thereof.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. The term parenteral as used herein includes subcutaneous, intracutaneous, intravenous, intramuscular, intra articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the modulators described herein are useful for the prevention and treatment of disease and conditions, including a disease or disorder related to NMDA receptor mediated glutamate excitotoxicity, such as, for example, stroke, head trauma, seizures, anoxia, cerebral ischemia, Parkinson's disease, Huntington's disease, epilepsy, and/or neuropathic pain. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Assays and methods of developing assays appropriate for use in the methods described above are known to those of skill in the art and, as will be appreciated by those skilled in the art, may be used as suitable with the methods of the present invention. The practice of the present invention employs and will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture*

*Of Animal Cells* (R. I. Freshney, Alan R Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

EXEMPLIFICATION

The NMDA subtype of glutamate receptors (NMDAR) at excitatory neuronal synapses plays a key role in synaptic plasticity. The extracellular signal-regulated kinase (ERK1,2 or ERK) pathway is an important component of NMDAR signal transduction controlling the neuroplasticity underlying memory processes, neuronal development, and refinement of synaptic connections. We have now shown that NR2B, but not NR2A or NR1 subunits of the NMDAR, interacts in vivo and in vitro with Ras-GRF1, a $Ca^{2+}$/calmodulin-dependent Ras-guanine-nucleotide-releasing factor. Specific disruption of this interaction in living neurons abrogates NMDAR-dependent ERK activation. Thus, Ras-GRF1 serves as an NMDAR-dependent regulator of the ERK kinase pathway. The association of Ras-GRF1 with the NR2B subunit and study of ERK activation in neurons with varied content of NR2B may indicate that NR2B-containing channels are the dominant activators of the NMDA-dependent ERK pathway.

Example 1

Interaction Between NR2B and Ras-GRF1

NR2B Directly Interacts with Ras-GRF1

Yeast two-hybrid screening of a rat brain library with a bait containing a portion of the NR2B cytoplasmic C-terminal domain (amino acids 886-1310) yielded five independent clones encoding the C-terminal portion of Ras-GRF1 (accession # P28818). These results suggest that NR2B directly interacts with Ras-GRF1.

The interaction of NR2B and Ras-GRF1 was further tested with purified proteins. The interacting C-terminal fragment of NR2B (886-1310), affinity purified from bacteria as a NusA fusion protein, bound in vitro translated Ras-GRF1 (FIG. 1A). Full-length Ras-GRF1 and NR2B co-expressed in HEK293T cells formed a complex that was co-immunoprecipitated by NR2B antibody (FIG. 1B). Since native neuronal NMDA receptors at mature synapses are heteromers of NR1 and one or more subtypes of NR2 (Cull-Candy, S., et al. (2001) Curr. Opin. Neurobiol. 11, 327-335),we tested whether Ras-GRF1 also associated with NR2A or NR1. As shown in FIG. 1B, Ras-GRF1 did not co-immunoprecipitate either NR1 or NR2A from HEK293T cells co-expressing these subunits. Finally, NR2B and Ras-GRF1 were co-immunoprecipitated from solubilized rat brain micro somes (FIG. 1C) or from 14-day-old primary cultures of dissociated rat neonatal hippocampal neurons. These data provide evidence that NR2B and Ras-GRF1 interact directly and associate in a molecular complex in native neurons.

Minimal Interacting Fragments as Binding Domains

In order to determine the signal transduction pathway dependent on NR2B-Ras-GRF interaction, we developed tools to specifically disrupt this interaction. The advantage of this approach over disrupting the gene or overexpressing the protein is that the interaction can be specifically targeted in vivo, without disturbing other components of the system. Minimal interacting fragments on both NR2B and Ras-GRF1 molecules were identified, and the peptides encoding these interacting fragments were tested for their ability to interfere with NR2B-RasGRF1 interactions.

Figure 2:
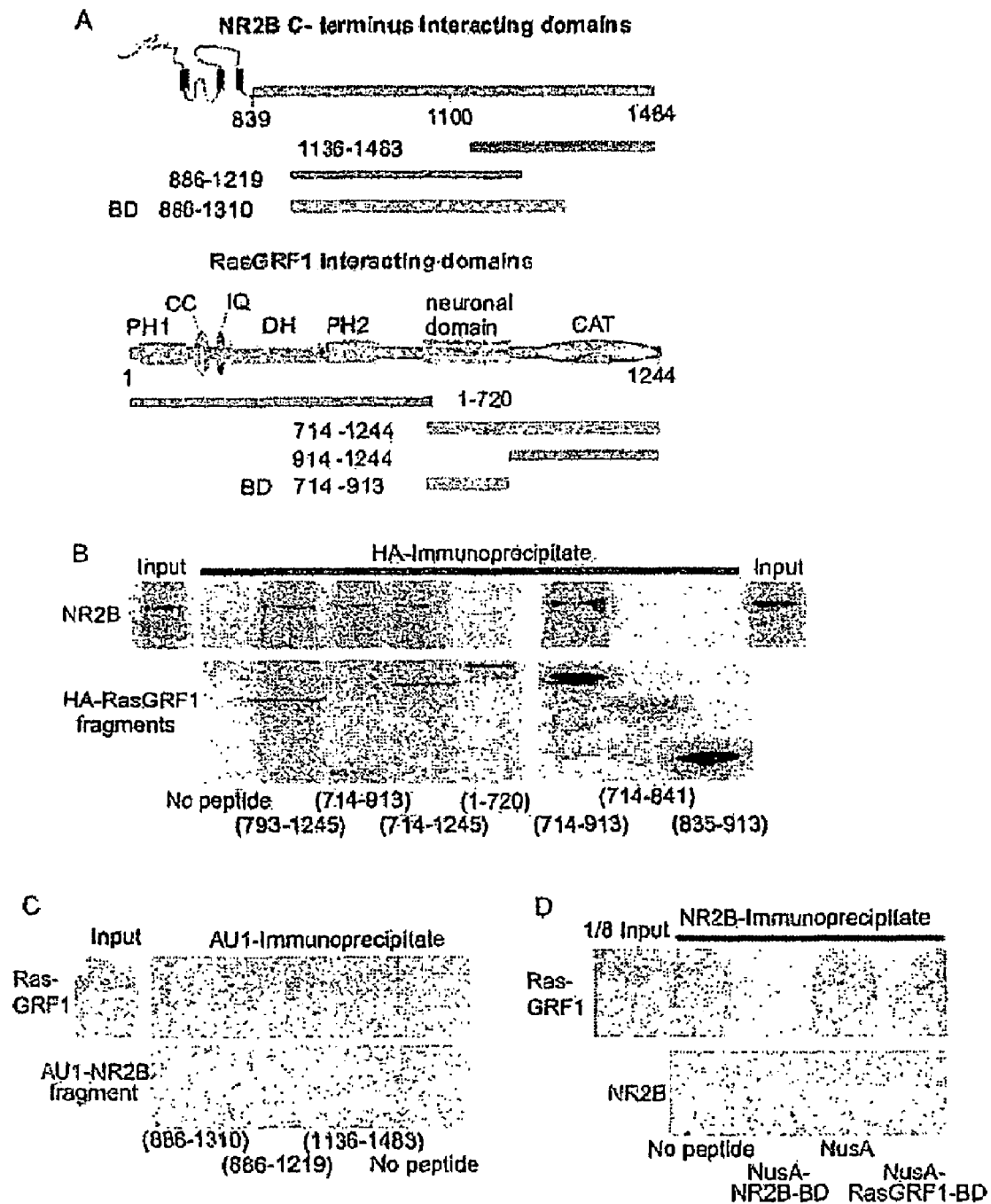
FIG. 2 shows a graphic depiction of the RasGRF1 and NR2B protein domains (panel A) indicating the RasGRF1 and NR2B Binding Domains used for an in vitro interaction assay (panel B) and a complex disruption experiment (panel D). (A) Map of the regions of NR2B and RasGRF1 DNAs used for the in vitro interaction assay. PH, plekstrin homology domain; CC, coiled coil domain; IQ, CaM binding domain; DH, DBL-homology domain. (B) RasGRF1 fragments bound full-length NR2B in vitro. In vitro translated full-length NR2B and HA-tagged RasGRF1 fragments were co-immunoprecipitated with anti-HA antibody. The right lower panel is shifted up relative to the lower left panel. (C) In vitro translated full-length RasGRF1 and AU1-tagged NR2B fragments were coimmunopecipitated with AU1 antibody. (D) Blocking peptides (RasGRF1-BD and NR2B-BD) dissociate RasGRF1 and NR2B in native complexes isolated from rat brain. NR2B was immunoprecipitated from brain microsome lysates in the presence of purified NusA-RasGRF1-BD or NusA-NR2B-BD, and the immunoprecipitate was probed with anti-RasGRF1 antibody.

The domain of NR2B interacting with RasGRF1 (NR2B-BD) and the domain of RasGRF1 interacting with NR2B (RasGRF1-BD) were determined by binding in vitro translated full-length molecules with in vitro translated epitope-tagged fragments of NR2B or RasGRF1, respectively (FIGS. 2A and 2B). The N-terminal portion of RasGRF1, which contains multiple functional domains (amino acids 1-720; FIG. 2A), did not bind NR2B. In contrast, the C-terminal prey-containing sequence bound NR2B (amino acids 714-1244; FIG. 2B). The distal portion of the C terminus containing the catalytic domain (amino acids 914-1244) was not essential for binding NR2B, while the region between the second PH domain and the catalytic domain (amino acids 714-913) was sufficient for NR2B binding. This domain is present only in neuron-specific RasGRF1; it is absent in the otherwise homologous, ubiquitously expressed, RasGRF2. The shorter peptides (amino acids 714-841 and 835-913) did not bind NR2B (FIG. 2B). Thus, truncation of the RasGRF1-specific sequence from either the C or N terminus resulted in loss of binding, suggesting that several separated protein segments may be responsible for specific interactions. Therefore, the RasGRF1 domain interacting with NR2B is localized between amino acids 714-913 of RasGRF1. The peptide encoding this region of RasGRF1 was designated as the RasGRF1-BD and used in subsequent experiments.

The NR2B bait (amino acids 886-1310) bound RasGRF1 in vivo and in vitro (FIG. 1A). This entire amino acid segment of NR2B constituted the best interacting peptide; a peptide encoding the distal portion of the bait (amino acids 1136-1310) did not bind RasGRF1 in vitro, and a peptide with a shorter C-terminal segment (amino acids 886-1219) bound RasGRF1 in vitro less efficiently than the 886-1310 bait (FIG. 2C). Therefore, the NR2B 886-1310 peptide was used as the NR2B-BD in subsequent competition studies.

To test whether NR2B-BD and RasGRF1-BD peptides were sufficient to disrupt the interaction between NR2B and RasGRF1 in the native complex, we immunoprecipitated NR2B-RasGRF1 complexes from 6- to 8-week-old rat brains in the presence of purified NR2B-BD and RasGRF1-BD NusA fusion proteins. Both NR2B- and RasGRF1-BD fusion proteins (3-5 µM) completely blocked co-immunoprecipitation of NR2B and RasGRF1 (FIG. 2D). Thus, both NR2B- and RasGRF1-BD were sufficient to disrupt the NR2B/RasGRF1 native complex.

Disruption of NR2B-RasGRF1 Interaction Abrogates NMDAR-Dependent ERK Activation

Figure 3:
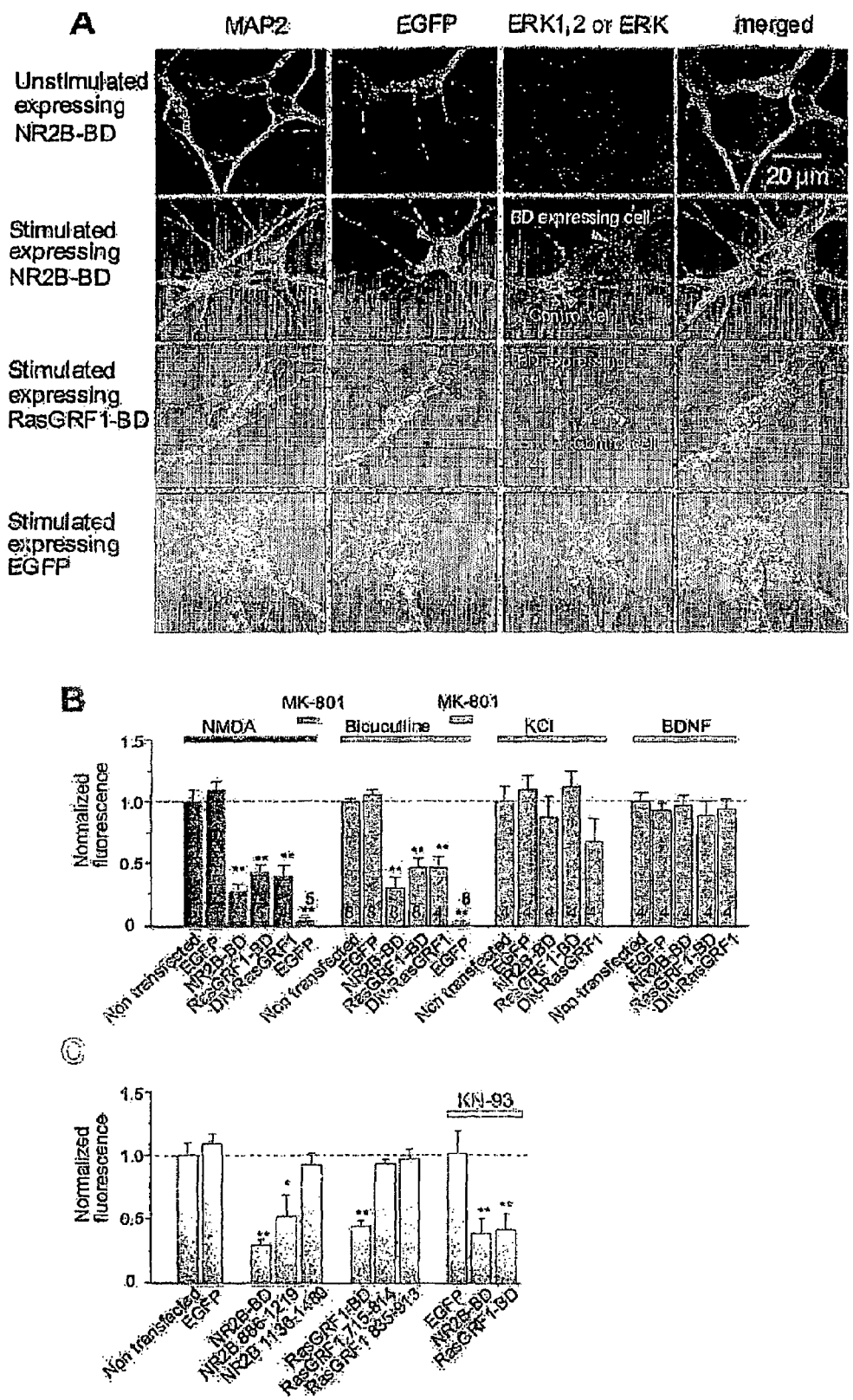
FIG. 3 shows the results of experiments using blocking peptides of RasGRF1-BD and NR2B-BD expressed in cultured hippocampal neurons indicating that the blocking peptides inhibit NMDAR-dependent activation of ERK1,2. (A) Images of activated (phosphorylated) ERK in neurons expressing EGFP, EGFP-NR2B-BD, or EGFP-RasGRF1-BD. (B) Population data summarizing the effect of NR2B-BD, RasGRF1-BD, and DN-RasGRF1 on NMDA, bicuculline, KCl, or BDNF-induced ERK phosphorylation. 10 $\mu$M MK-801 was applied to confirm the NMDAR dependence of ERK activation. (C) Nonbinding fragments of NR2B-BD, RasGRF1-BD did not affect NMDA-dependent ERK activation. 5 $\mu$M KN-93 in the incubation media also had no effect on NMDA-dependent ERK activation. Bars show average phospho-ERK fluorescence normalized to the fluorescence of EGFP-transfected cells±SEM; numbers of independent experiments indicated on the bars. Asterisks indicate significant differences from those calculated for cells expressing EGFP alone. Double asterisks correspond to $p<0.001$, single asterisk shows $0.01<p<0.05$.

Since RasGRF1 is a $Ca^{2+}$/calmodulin-dependent activator of Ras (Farnsworth, C. L., et al. (1995) Nature 376, 524-527) and $Ca^{2+}$ entering the neuron through the NMDAR channel activates the ERK pathway (Xia, Z., et al. (1996) J. Neurosci. 16, 5425-5436), it may be possible that NR2B bound RasGRF1 transduces the signal from the NMDAR to ERK. Therefore we utilized a dominant-negative (DN) form of RasGRF1 (Vanoni, M., et al. (1999) J. Biol. Chem. 274, 36656-36662) expressed in cultured hippocampal neurons to test its effect on ERK activation. The activity of ERK was evaluated by immunostaining with an antibody recognizing the active (phosphorylated) ERK (Payne, D. M., et al. (1991) EMBO J. 10, 885-892). As shown in FIG. 3B, RasGRF1-DN significantly suppressed NMDA- and bicuculline-induced ERK activation. Overexpression of RasGRF1-DN did not significantly affect BDNF- and depolarization-dependent ERK activation.

If NR2B-RasGRF1 interaction is critical for signal transduction from the NMDAR to ERK activation, then disruption of this interaction should prevent NMDA-dependent ERK activation. To disrupt the RasGRF1-NR2B interaction in living neurons, we transfected primary cultures of hippocampal neurons with enhanced green fluorescent protein (EGFP) fused to binding domains of NR2B or RasGRF1. The expression of fusion proteins encoding the entire binding domains resulted in a striking decrease in the level of NMDAR-dependent ERK activation compared to control nontransfected neurons or neurons expressing GFP alone (FIGS. 3A and 3B). Expressed binding domains are large peptides and thus may contain regions interacting with other molecules, but smaller fragments were ineffective in binding assays (FIGS. 2B and 2C). The BD fragments that were ineffective in binding nonetheless contained large binding domain segments and were used as additional controls to rule out the possibility of a nonspecific ERK activation (FIG. 3C). Thus, expression of the dominant-negative form of RasGRF1, the complete BDs (but not overlapping peptides encoding only portions of the binding domains), effectively inhibited the NMDAR-dependent activation of ERY These data support the hypothesis that a direct link between NR2B and RasGRF1 may be important for NMDAR-specific ERK activation.

Neuronal ERK activity is regulated by several signals, including $Ca^{2+}$ influx through the L-type voltage-dependent $Ca^{2+}$ channel (Dolmetsch, R. E., et al. (2001) Science 294, 333-339) and BDNF-mediated pathways (Bonni, A., et al. (1999) Science 286, 1358-1362). To determine whether expression of NR2B-BD or RasGRF1-BDs specifically interrupted NMDAR-mediated ERK activation rather than simply inhibiting ERK activity, NMDA-independent stimuli were used to activate ERK. As shown in FIG. 3B, the expressed NR2B- and RasGRF1-BD peptides had no effect on depolarization- or BDNF-induced ERK activation. Furthermore, NMDAR-dependent phosphorylation of the CREB transcription factor (Ginty, D. D., et al. (1993) Science 260, 238-241; Xia et al., 1996 supra) was not affected by NR2B- or RasGRF1-BD expression, indicating that the NMDAR pathway upstream of RasGRF1 was not affected.

The RasGRF1 locus interacting with NR2B also interacts with CaMKII (Bayer, K. U., et al. (2001) Nature 411, 801-805). To test whether the NR2B-BD peptide might also block NMDAR-dependent ERK activity by inhibiting CaMKII activation, we examined whether inhibition of CaMKII activity affected NMDAR-dependent ERK activation. Application of KhT-93 (a cell-permeable, CaMKII-selective inhibitor) altered neither NMDA- nor bicuculline-dependent ERK activation, nor did it affect NR2B-BD or RasGRF1-BD peptide block of ERK activation (FIG. 3C). In control experiments, KN93 effectively suppressed the phosphorylation of CREB and SynGAP in cultured hippocampal neurons. Thus, under these conditions, NMDAR-dependent ERK activation did not require CaMKII activity. Therefore, if NR2B-BD interfered with NR2B-CaMKII interactions, it did not significantly affect NMDAR-dependent ERK activation.

Figure 4:
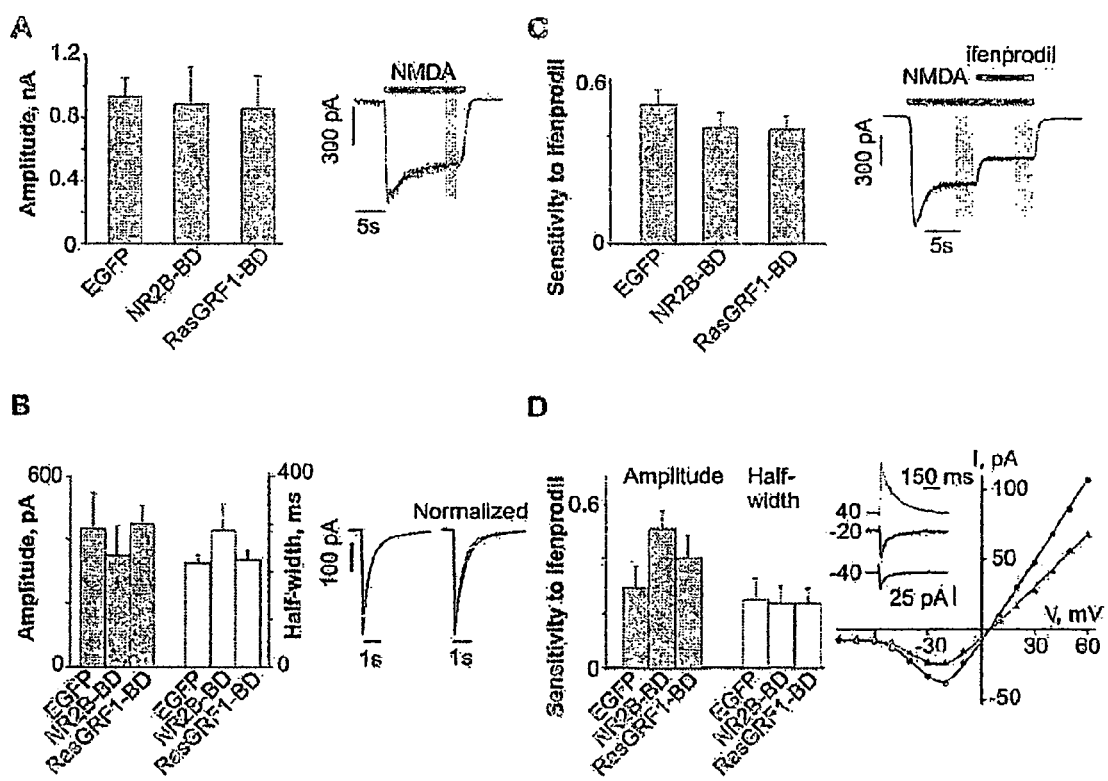
FIG. 4 shows the results of experiments involving expression of RasGRF1-BD or NR2B-BD in neurons indicating that these peptides did not affect NMDA receptor-mediated currents. (A) Average amplitudes (n=10) of steady-state whole-cell currents evoked by bath application of 100 $\mu$M NMDA to neurons expressing GFP or GFP-BD. The trace illustrates the whole-cell current induced by bath application of 100 $\mu$M NMDA to a hippocampal neuron expressing GFP-RasGRF1-BD. Vertical bar indicates a segment of the recording used for calculation of mean value. (B) Averaged spontaneous NMDA EPSCs in neurons expressing GFP or GFP-BD. Columns show the mean amplitude (filled) and half-width (open) of NMDA EPSCs obtained from five experiments. The traces are the averaged EPSCs (30 events) recorded from a neuron expressing GFP (dark) or GFP-RasGRF1-BD (light). (C) Ifenprodil sensitivity of whole-cell current induced by bath application of NMDA. The trace illustrating the recording procedure was obtained in a RasGRF1-BD-expressing neuron. (D) Ifenprodil-sensitivity of the NMDA EPSPs evoked in CA3 pyramidal neurons in organotypic cultures of hippocampal slices. Columns represent the averaged (n=7) ifenprodil sensitivity of the amplitude (filled) and half-width (open) of NMDAR EPSCs recorded at a holding potential of 40 mV. Ifenprodil sensitivity was defined as $(C_T-C_I)/C_T$ where C is the NMDAR-mediated current without ($C_T$) and with ($C_I$) 3 $\mu$M ifenprodil. The traces illustrate EPSCs recorded at different potentials from a neuron expressing RasGRF1-BD. The current-voltage relationships of the NMDA EPSCs were measured before (circles) and during (triangles) ifenprodil application.

Expression of RasGRF1-BD or NR2B-BD could conceivably affect ERK activation upstream of RasGRF1 by decreasing NMDAR currents, and thus local $[Ca^{2+}]_i$. To test this possibility, we studied the properties of the NMDAR-mediated currents in neurons expressing BD fusion constructs. The expression of either binding domain did not affect the average amplitude of the whole-cell current induced by bath application of NMDA (FIG. 4A), or the mean amplitude and kinetics of the spontaneous NMDAR-mediated excitatory postsynaptic currents (NMDA EPSCs; FIG. 4B).

Figure 5:
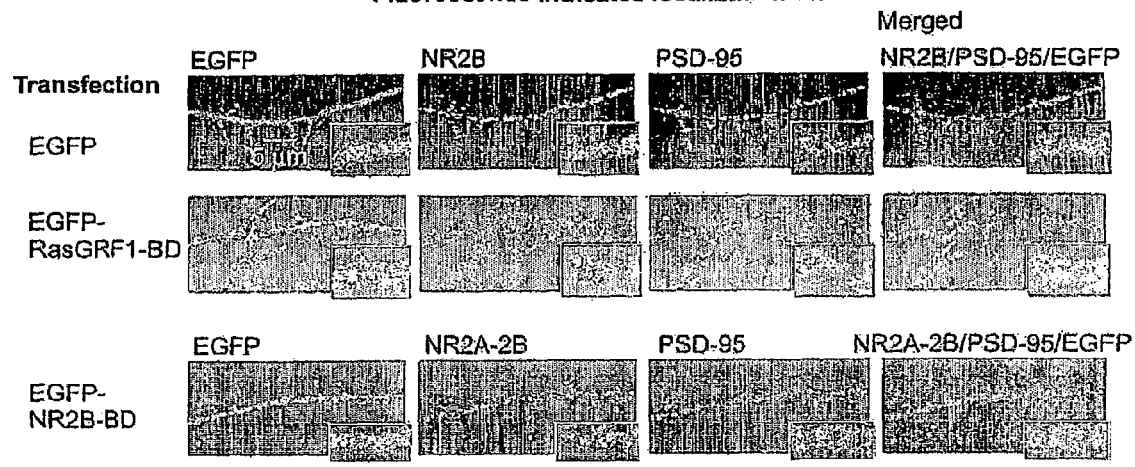
FIG. 5 shows the results of immunocytochemistry experiments on cultured neurons expressing blocking peptides of RasGRF1-BD and NR2B-BD indicating that the expression of these peptides did not change the localization or density of NR2B or PSD-95. (A) Images of NR2B and PSD95 immunoreactive clusters. (B) Averaged cluster density exhibited by NR2B antibody labeling (filled) or NR2A/B labeling (open).
Figure 5:
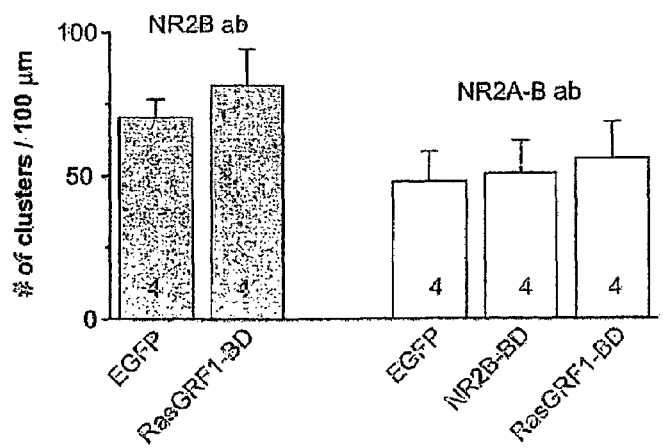

The observation that RasGRF1 interacts with the NR2B, but not the NR2A or NR1 subunits, may indicate that channels containing the NR2B subunits predominantly activate ERK Therefore, the NR2B subunit-containing channel currents may be involved in ERK activation. We tested whether expression of NR2B- and RasGRF1-blocking peptides modulated NR2B subunit-mediated current. To determine the NR2B-specific component of NMDA current, we employed ifenprodil, a noncompetitive antagonist of NR2B-containing NMDA receptors (Williams, K. (1993) Mol. Pharmacol. 44, 851-859; Tovar, K. R., and Westbrook, G. L. (1999) J. Neurosci. 19, 4180-4188). FIG. 4C demonstrates that neither RasGRF1-BD nor NR2B-BD expression changed the proportion of ifenprodil-sensitive (NR2B) current stimulated by NMDA bath application to cultured neurons. It was not possible to estimate the proportion of the NR2B-mediated component in spontaneous NMDAR EPSCs in cultures of the dissociated neurons, since ifenprodil significantly reduced the frequency of the events. To circumvent this problem, we expressed NR2B-BD- or RasGRF-BD-blocking peptides in organotypic cultures of hippocampal slices and studied the effect of ifenprodil on the properties of the evoked NMDA EPSCs. Neither of the expressed peptides decreased the portion of the ifenprodil-sensitive component of the evoked EPSCs (FIG. 4D). Confocal microscope-acquired images of cultured neurons transfected with either GFP-RasGRF1-BD or GFP-NR2B-BD and stained by NR2B antibody did not reveal any changes in the average number NR2B-positive clusters as compared to cells expressing GFP alone (FIG. 5). Taken together, the data indicate that the blocking peptides specifically inhibited the NR2B-RasGRF1 interaction without affecting NR2B receptor number or NMDAR-dependent $Ca^{2+}$ entry.

ERK are Preferentially Activated via NR2B-Containing Channels

Figure 6:
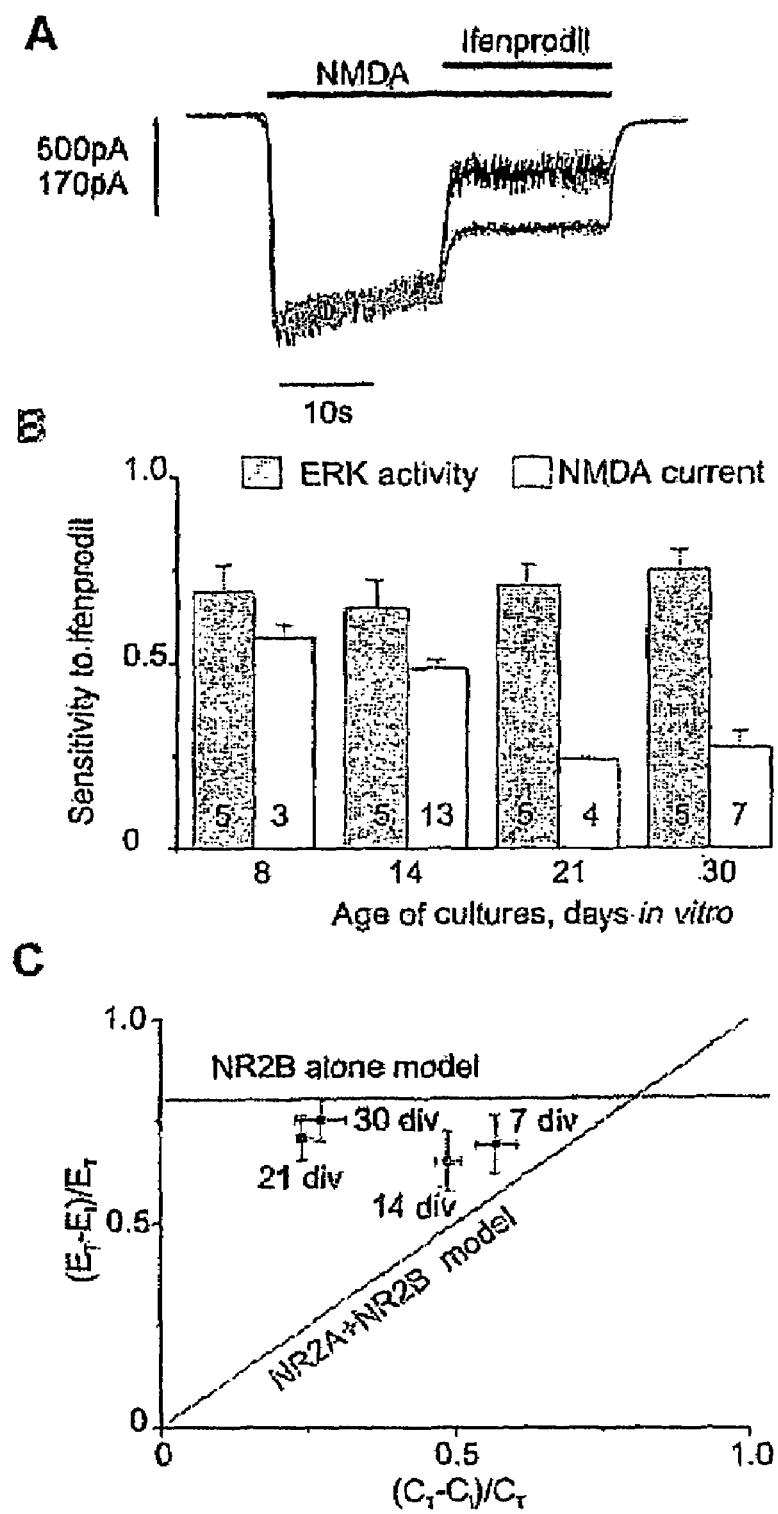
FIG. 6 shows the results of experiments investigating ifenprodil sensitivity of NMDA-Dependent ERK activation and NMDA receptor-mediated current in hippocampal neurons at varying days in culture. (A) Ifenprodil-inhibited NR2B-containing current at 7 (dark) and 21 (light) div (bath application of 100 μM NMDA). Vertical bars indicate segments of recordings used to calculate the mean values in (B). (B) Ifenprodil-sensitive NMDA-induced current (open bars) decreased while the ifenprodil sensitivity of ERKs (filled bars) did not change with maturation. Ifenprodil sensitivity was defined as $(E_T-E_I)/E_T$ and $(C_T-C_I)/C_T$ where E and C are the NMDA-induced phospho-ERK immunoreactivity and ion current, respectively. Indices indicate measurements with (I) and without (T) 3 μM ifenprodil. (C) Ifenprodil-sensitive ERK activity does not depend on the fraction of ifenprodil-sensitive NMDA current. Solid lines indicate the expected results in which ERK was activated by $Ca^{2+}$ entering via all NMDA channels (NR2A+NR2B model) or by only NR2B-containing channels (NR2B-only model). Experimental data are taken from (B).

Given the specific coupling of RasGRF1 to NR2B subunit, it may be possible that ERK is preferentially activated by $Ca^{2+}$ entering neurons via NR2B-containing NMDAR channels. The expression level of NR2B subunit in vivo remains stable during neuronal maturation, while NR2A expression progressively increases (Monyer, H., et al. (1994) Neuron 12, 529-540; Sheng, M., et al. (1994) Nature 368, 144-147). In neurons cultured in vitro, the ratio between NR2B and NR2A subunits also decreases with age (Zhong, J., et al. (1994) Mol. Pharmacol. 45, 846-853; Li, J. H., et al. (1998) Eur. J. Neurosci. 10, 1704-1715), and as a result there is an age-dependent decrease of the NMDA current sensitivity to the NR2B blocker, ifenprodil (Tovar and Westbrook, 1999 supra; Hoffmann, H., et al. (2000) 75, 1590-1599). In heterologous expression systems, ifenprodil at 3 µM inhibits up to 80% of NR2B-mediated current and has no effect on NR2A-mediated current (Williams, 1993 supra; Tovar and Westbrook, 1999 supra). In young neuronal cultures (neurons that presumably contain only NR2B/NR1 NMDA receptors [Zhong et al., 1994 supra; Li et al., 1998 supra]), ifenprodil inhibits ~70% of NMDA-mediated current and this inhibition decreased to 20%-30% in 3-week-old cultures (Tovar and Westbrook, 1999 supra; Hoffmann et al., 2000 supra). If ERK activation depended exclusively on NR2B-containing channels, then block of NR2B-specific current may significantly suppress NMDA-induced ERK activation independent of the proportion of NR2B-containing channels. In this case there should be no dependence of the proportion of ifenprodil-sensitive ERK activity on the proportion of ifenprodil-sensitive total NMDA current (see Experimental Procedures, Model). Alternatively, if ERK activation does not depend on whether its source was via an NR2A- or NR2B-containing channel, then the ifenprodil-sensitive portion of ERK activity will decrease in neurons expressing a lower fraction of NR2B subunit-containing channels. In agreement with previous studies (Tovar and Westbrook, 1999 supra; Hoffmann et al., 2000 supra), 3 µM ifenprodil suppressed 60% of NMDAR current in hippocampal neurons 8 div (FIGS. 6A and 6B). In the same cultures, we observed 70% inhibition of NMDAR activated ERK (FIGS. 6A and 6B). The remaining 30% of the activity of ERK may be related to the uninhibited fraction of NR2B. During neuron maturation, the portion of the ifenprodil-sensitive NMDA current progressively decreased by ~25% with days in culture while the degree of ifenprodil-sensitive ERK activation did not change significantly (FIGS. 6A and 6B). This observation may indicate that NR2B-containing channels are dominant activators of the NMDA-dependent ERK pathway (FIG. 6C).

Experimental Procedures

Yeast Two-Hybrid Screening cDNAs encoding fragments of the rat NR2B C terminus were subcloned into the Gal4 binding domain fusion vector pGBKT7 (Clontech). These constructs were used for screening a rat brain library. (Matchmaker pACT2, Clontech) expressed in AH109 yeast.

cDNA4 Constructs and Recombinant Proteins

NusA fusion proteins from rat NR2B (886-1310) and rat RasGRF1 (714-913) were subcloned into pET43.1 (Novagen) and expressed in BL21TrxLysS (Novagen) bacteria and 6His-NusA-fusion proteins affinity-purified on a cobalt-resin (Talon, Clontech).

For in vitro translation, fragments of rat NR2B and rat RasGRF1 were made by PCR with 5'-primers containing AU1- and HA-tag encoding sequences; amplified sequences were subcloned into pcDNA3.1. For 293T transfection, the following cDNAs were used: mouse RasGRF1 in pcDNA3, GFP-rat NR2B, GFP rat NR2A in pcDNA1.1, and rat NR1 in pEGFP-C1 (Clontech). EGFP fusion constructs were made by subcloning cDNA fragments encoding different portions of NR2B and RasGRF1 into pEGFP-C1 (Clontech). EGFP fusion constructs were transferred from pEGFP into pSinRep5 and used for preparation of the Sindbis pseudovirus gene transfer system according to the manufacturer's protocol (Invitrogen, Carlsbad, Calif.).

Cell Cultures and Transfections

HEK293T cells were grown in DMEM/F12 media supplemented with glycine, Na-hypoxanthine, penicillin/streptomycin, and 10% FBS. Cells were transfected using Lipofectamine 2000 (Invitrogen) and cultured for 48 hr.

Neurons from 18 day rat embryos were dissociated using trypsin and plated on coverslips coated with poly-L-ysine in minimal essential medium (MEM) with 10% NU serum (BD Biosciences, Le Pont de Claix, France) at densities of 30,000 cells/cm$^2$ as described (Brewer, G. J. (1995) J. Neurosci. Res. 42, 674-683). On days 7 and 11 of culture incubation, half of the medium was changed to MEM with 2% B27 supplement (Invitrogen).

Cells were transfected with cDNA for EGFP fusion proteins (LipofectAMINE 2000; Invitrogen) or by pseudoviral infection using a Sindbis expression system (Invitrogen). Neurons were incubated with cDNA and LipofectAMINE for 2 hr, rinsed, and incubated with culture media (MEM with 2% of B27 supplement) 17 hr prior to the experiment. For viral delivery, neuronal cultures were incubated 30 min with pseudoviral constructs diluted 200-500× in culture media. Cultures were rinsed and incubated in media for 15 hr. 0.1% to 1.5% of neurons were fluorescent after expressing LipofectAMINE-delivered constructs while Sindbis infection yielded 1%-10% transfection efficiency. Most of the experiments were performed on 12-14 days in vitro (div) cultures unless otherwise indicated.

Organotypic cultures of hippocampal slices were prepared as described (Becq, H., et al. (1999) J. Neurosci. Res. 58, 553-566) according to modified technique of Stoppini et al. (J. Neurosci. Methods 37, 173-182 (1991)). Hippocampal slices (400 µm) were cut from postnatal 7-day-old rat brains and incubated in culture medium in 5% $CO_2$. Infections were performed on the 6$^{th}$ day of slice incubation by local pressure injection of virus via a patch pipette (tip diameter ~1 µm) into the CA1 region of the hippocampus.

Immunoprecipitation and Pull-Down Assays

Mouse RasGRF1 in pcDNA3 (Martegani, E., et al. (1992) EMBO J. 11, 2151-2157) was translated in vitro using the TNT system (Invitrogen) and [$^{35}$S]methionine. 5 µl of the translated RasGRF1 was incubated for 1 hr at 4° C. with 2 µg of NusA-NR2B (886-1310) or NusA bound to $Co^{2+}$ beads in 250 µl RIPA buffer (20 mM Tris-Cl [pH 8.0], 150 mM NaCl, 1% Triton X-100, 0.5% Na-Cholate, 0.1% SDS), washed with RIPA buffer, and solubilized in SDS sample buffer.

Transfected cells were solubilized in lysis buffer (100 mM Tris-Cl [pH 8.5], 500 mM NaCl, 1% Triton X-100) supplemented with com plete protease inhibitor (Roche) and immunoprecipitated with NR2B (Santa Cruz, sc-9057), NR1, or NR2A (Chemicon) antibody (5 µg/ml), washed with lysis buffer, separated on SDS gel, and blotted on PVDF. Blots were probed with anti-RasGRF1 (Santa Cruz) and the appropriate NR subunit antibody. 6- to 8-week-old rat brain P2 microsomes were isolated and solubilized as described (Luo, J., et al. (1997) Mol. Pharmacol. 51, 79-86). 80 µg of solubilized protein were immunoprecipitated with NR2B, RasGRF1, or pooled rabbit IgG, and immunoprecipitated proteins were probed on Western blot with RasGRF1 and NR2B antibodies. All immunoprecipitation experiments were only taken as valid if repeated 3-5 times with similar results. Routine negative controls with antigen pre-absorption were carried out for antibodies used in immunoprecipitation experiments. Also, all immunoprecipitating antibodies were tested for the cross-reactivity with in vitro translated co-immunoprecipitated molecules. Both tests proved their specificity and the absence of cross-reactivity of the immunoprecipitating antibody.

For in vitro binding experiments, equimolar amounts of in vitro translated $^{35}$S-labeled proteins (calculated from radioactivity of the excised protein band and cysteine content in the specific fragment) were incubated with a 3-fold molar excess of translated RasGRF1 for 30 min at 30° C., diluted with RIPA buffer, and immunoprecipitated with anti-HA-agarose (Santa Cruz). In competition experiments, RasGRF1 and NR2B were immunoprecipitated for 2 hr at 4° C. from solubilized rat brain microsomes in the presence of 10 µM NusA, 10 µM NusA-RasGRF1-BD, or 5 µM NusA-NR2B-BD.

Immunocytochemistry and Confocal Microscopy of Cultured Hippocampal Neurons Phospho-ERK Immunocytochemistry Three hours before stimulation, TTX (1 µM), CNQX (40 µM), APV (100 µM), and nimodipine (5 µM) were added to neurons. For stimulation, coverslips with neurons were transferred into the following solutions.

(1) 100 µM NMDA, 10 µM glycine, 1 µM TTX, 40 µM CNQX, 5 µM nimodipine dissolved in culture media and incubated for 3 min. Under these conditions, longer (10 min) stimulation with NMDA resulted in significantly lower ERK stimulation.

(2) 10 μM bicuculline, 10 μM glycine, 5 μM nimodipine (without TTX, APV, or CNQX) in culture media incubated for 5 min.

(3) 50 mM KCl included in modified extracellular media: 120 mM NaCl, 10 mM HEPES, 10 mM D-glucose, 2.0 mM $CaCl_2$, 2.0 mM $MgCl_2$, 1 μM TTX, 40 μM CNQX, 100 μM APV and incubated for 10 min.

(4) 100 ng/ml BDNF in culture media with TTX (1 μM), CNQX (40 M), APV (100 μM), and nimodipine (5 μM), incubated for 10 min.

After stimulation, neurons were fixed with 4% formaldehyde and labeled with rabbit anti-phospho-p44/42 ERK antibody (Cell Signaling) and with mouse anti-MAP2 antibody (Sternberger Monoclonals). Cy3-conjugated goat anti-rabbit IgG and Cy5-conjugated goat antimouse IgG (Jackson Immunoresearch Laboratories, West Grove, Pa.) were secondary antibodies. NMDA and all antagonists were from Tocris Neuramin. BDNF was from Calbiochem. Images were acquired with an Olympus Fluoview-500 confocal microscope (40×; 1.0 NA) and quantified using Olympus Fluoview software. In each experiment, the pERK fluorescence of the cell soma was measured for 25 neurons taken from consecutive fields. Phospho-ERK fluorescence data were normalized to the values obtained in nontransfected cells after NMDA stimulation. The background fluorescence (mean fluorescence of nonstimulated neurons) was subtracted prior to normalization.

Immunocytochemistry of NR2B Subunits

Coverslips with cultured neurons were fixed with 4% paraformaldehyde, permeabilized with 0.3% Triton X-100, and blocked in 10% goat serum in PBS. A rabbit polyclonal antibody against the N terminus of the NR2B subunit of the NMDA receptor (AB1557P, Chemicon, Temecula, Calif.) was used for detection in neurons expressing GFP and RasGRF1-BD. These antibodies could not be used for study of the NR2B subunit distribution in neurons expressing NR2B-BD since they recognized the expressed construct. The distribution of NR2A/B subunit was determined using polyclonal antibody AB 1548 (Chemicon). A mouse monoclonal antibody (clone K 28/43, Upstate, Waltham, Mass.) was used to detect PSD-95. Secondary antibodies were the same as that used for detection of ERK and MAP2. To quantify the distribution of clusters in transfected cells, we first focused on dendrites of neurons expressing the EGFP fluorescent construct. Thereafter, fluorescent images of GFP, NR2B, and PSD-95 were acquired confocally (60×; NA 1.4 objective, zoom 5). Cluster density and brightness were analyzed with the MetaMorph Imaging System (Universal Imaging, Westchester, Pa.). Ten neurons were analyzed from each experiment (3-4 dendritic regions for each neuron).

Electrophysiological Recordings

Electrophysiological recordings from neurons were performed 19-24 hr after transfection or 14-20 hr after viral infection. No difference between transfected and infected neurons was observed. Neurons were continuously perfused with extracellular solution containing (in mM): 140 NaCl, 2.5 KCl, 20 HEPES, 20 D-glucose, 2.0 $CaCl_2$, 0.02 glycine, 0.01 bicuculline, 0.01 CNQX, and 0.001 tetrodotoxin (TTX) with no added $Mg^{2+}$ (pH 7.4). Measurements of the spontaneous NMDA-EPSCs were recorded in the absence of TTX. NMDA (100 μM) or NMDA and ifenprodil (3 μM) were dissolved in the bath solution and delivered by gravity via a double-barrel pipe displaced 70-100 μm from the neuron. Recording electrodes (2-4 MΩ) were pulled from borosilicate glass (TW 150F-15; World Precision Instruments), filled with solution containing (in mM) 115 Cs methane-sulfonate, 20 CsCl, 10 HEPES, 2.5 $MgCl_2$, 4 $Na_2$-ATP (adenosine triphosphate), 0.4 Na-GTP (guanosine triphosphate), 10 mM Na-phosphocreatine, and 0.6 mM EGTA (pH 7.2). Ifenprodil was from RBI.

Recordings were made using an Axopatch-200A amplifier and pCLAMP acquisition software (Axon Instruments). Series resistance varied from 6 to 8 MΩ and electronic compensation for series resistance was employed. Data were low-pass filtered at 2 kHz and acquired at 10 kHz. NMDA receptor-mediated EPSCs were analyses using Mini Analysis software (Synaptosoft Decatur, Ga.). The same number of events was compared in each set of experiments.

Organotypic Hippocampal Cultures

For electrophysiological recordings, slices were placed in a recording chamber and perfused with ACSF including in mM: 119 NaCl, 2.5 KCl, 2 $CaCl_2$, 2 $MgCl_2$, 26 $NaHCO_3$, 1 $NaH_2PO_4$, 11 glucose, 0.01 bicuculline, 0.01 CNQX, 0.002 2-chloroadenosine (pH 7.4), in 5% $CO_2$/95% $O_2$. Synaptic responses were evoked by bipolar electrode with monophasic voltage pulses (1-10 V, 200 μs). The stimulating electrodes were placed over Schaeffer collateral fibers. NMDA evoked EPSCs were recorded at different holding potentials before, during, and after ifenprodil application in order to measure the I-V relationship. For analysis, at least 5 NMDA-evoked EPSCs were averaged for every experimental condition.

Statistical Analysis

All population data were expressed as mean±SEM. The Student's t test was employed to examine the statistical significance of the differences between groups of data.

Model

If $C_T$ is total NMDA-activated current, $C_I$ is the current elicited in the presence ifenprodil, α is the coefficient of residual activity of NR2B channels in the presence of ifenprodil, and A and B are the number of NR2A- and NR2B-containing NMDA channels, then $C_T=n(A+B)$, $C_I=n(A+\alpha B)$ and the portion of the current via NR2B-containing receptor is $B/(A+B)=(C_T-C_I)/(1-\alpha C_T)$.

We define $E_T$ and $E_I$ as the total and ifenprodil-insensitive ERK activity, respectively. For a model in which $Ca^{2+}$ entering neurons via both NR2A- and NR2B-containing channels (A+B model), $E_T=k(A+B)$ and $E_I=k(A+\alpha B)$. The degree of ERK activity inhibited by ifenprodil will be: $(E_T-E_I)/E_T=(1-\alpha)B/(A+B)=(C_T-C_I)/C_T$. In other words, normalized ifenprodil-sensitive ERK activity will be directly proportional to the normalized ifenprodil-sensitive NMDA current. For a model in which the $Ca^{2+}$ enters neurons only via NR2B-containing channels (B-only model), $E_T=kB$ and $E_I=k\alpha B$. The normalized ERK activity inhibited by ifenprodil will be: $(E_T-E_I)/E_T=(1-\alpha)$ and will not correlate with ifenprodil-sensitive NMDA current.

Example 2

Analysis of the Neuroprotective Effects of RasGRF1-BD and NR2B-BD

We used two different assays to analyze the neuroprotective effects of NR2B-BD or RafGRF-BD. The results obtained using assays I and II are shown in FIGS. 7(A) and 7(B), respectively.

Figure 7:
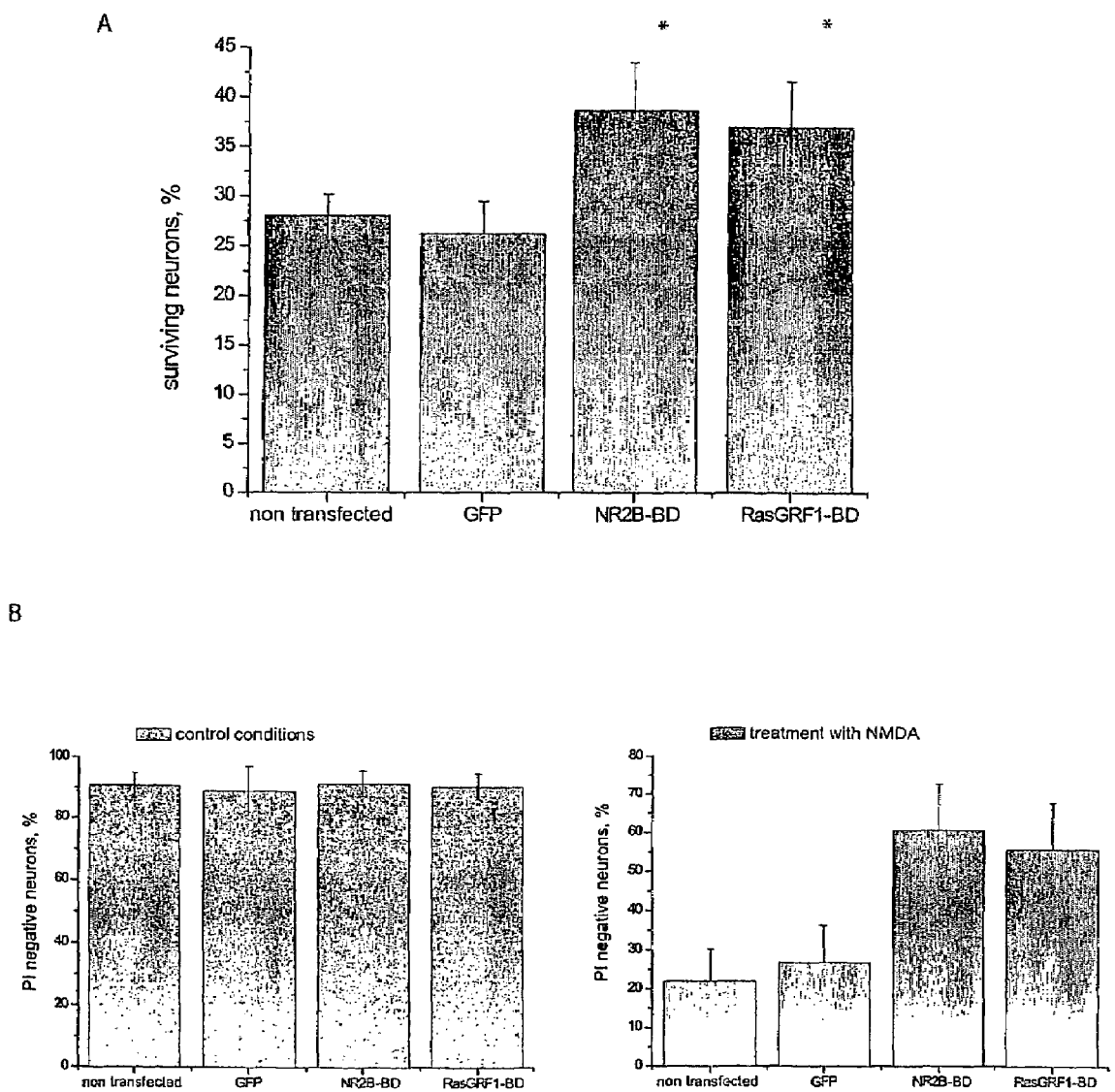
FIG. 7 shows the results of experiments investigating the Neuroprotective Potencies of RasGRF1-BD and NR2B-BD. (A) Survival of hippocampal neurons in culture exposed to Glutamate (100 μM) and Glycine (10 μM) for a 20 minute period. 14 div neuronal cultures were transfected with GFP, NR2B-BD or RasGRF1-BD 24 hours prior to analysis. The neuronal cultures were then incubated with glutamate for 20 minutes, washed with culture media and returned to the incubator for an additional 24 hours. The cells were then fixed with PFA and stained with a neuronal specific antibody, Map2. The percentage of surviving neurons was detected as a ratio of the neuron quantity per coverslip of control cultures (non treated) as compared to the neuron quantity of cultures incubated with glutamate. * indicates values significantly different (P<0.05, Student's paired t-test, n=5) from those obtained with GFP transfected neurons. (B) Percentage of propidium iodide-resistant (surviving) neurons in organotypic hippocampal slices (P5+7div) expressing GFP, NR2B-BD or RafGRF-BD in control conditions and after 20 minutes exposure to NMDA (50 μM). The fluorescence of propidium iodide (PI) was measured 24 hours later. PI enters damaged cells and is a convenient tool to determine neuronal cell death. For PI staining, the slices were incubated in culture medium containing 0.1 mg/ml PI for 2 h. GFP, NR2B-BD and Raf-GRF-BD were expressed using the SindBis expression system. Mean±SEM. N=3. These experiments showed an increase in the percentage of surviving neurons for neurons expressing NR2B-BD or RafTRF-BD as compared to control neurons (non-transfected or GFP transfected).

Assay I: primary cultures of dissociated hippocampal neurons (FIG. 7(A)). This method may be used to analyze the mechanisms of glutamate-dependent excitotoxicity (see e.g., Medina, et al., Eur J Neurosci. (1999) 11(4): 1167-78). Briefly, neuronal cell death was induced by a 20 minute exposure to Glutamate (100 μM) and Glycine (10 μM).

Glutamate dependent excitotoxicity induces at least two types of neuronal cell death: apoptosis (nuclear condensation and fragmentation) and necrosis (cytoplasmic membrane permeability). Expression of either NR2B-BD or RasGRF1-BD in the neurons decreased significantly the amount of neuronal cell death induced by exposure to the glutamate and glycine (NR2B-BD by 47±2% and RasGRF1 by 41±1% (n=5)), see FIG. 7(A).

Assay II: propidium iodide (PI) resistance. Organotypic hippocampal slice cultures were either exposed to ischemia (30 minutes perfusion with $N_2$ instead of $O_2/CO_2$) or incubated for 20 minutes with excitotoxic concentrations of N-methyl-D-aspartate (NMDA) (50 μM). NR2B-BD, RasGRF1-BD, or GFP were expressed in the CA1 pyramidal neurons and the effects of induced neurotoxicity was examined. Cell death was measured as cellular uptake of PI (3,8-diamino-5-[3-(diethylethylamino)propyl]-6-phenyl phenanthridinium diiodide at 24 and 48 h after exposure to NMDA or ischemia. As shown in FIG. 7(B), the expression of both NR2B-BD and RasGRF1-BD increased the percentage of neuronal survival (e.g., the percentage of PI negative neurons) as compared to non-transfected or GFP transfected control cells.

Experimental Procedures

Primary Cultures of Hippocampal Cells

Cell cultures were prepared from two-day-old Wistar rats as described by Medina et al. (1994). The hippocampi were removed and dissected free of meninges in cold (6° C.) oxygenated, $Ca^{2+}$ and $Mg^{2+}$-free phosphate buffered saline (PBS), supplemented with 0.6% glucose. The tissue was then transferred to PBS-glucose with $Ca^{2+}$ and $Mg^{2+}$, cut into small pieces (0.2-0.4 mm and incubated for 20 min. at room temperature (RT) with 0.3% protease (*Aspergillus Oryzae* type XXIII, Sigma, St Louis, USA) and 0.1% DNase (Type I, Sigma). Protease activity was stopped by the addition of NU-serum (Becton Dickinson). Cells were mechanically dissociated in PBS-glucose containing 0.05% DNase (Type I, Sigma). After a brief centrifugation, cell pellets were resuspended in culture medium (see below). Tissue culture dishes were coated for 12 h with 10 mg/ml poly-L-lysine (MW: range 70,000-150,000; Sigma) in $H_2O$ at 37° C. The cells were seeded at a density of 150,000 cells/ml in a culture medium made of MEM (Life Technologies, Gibco BRL), supplemented with 10% NUserum (Becton Dickinson). Cells were grown at 37° C. in 95% $O_2$ and 5% $CO_2$ with 100% humidity. On day 5 in culture, medium was replaced with fresh medium (¼ of total volume). Cells cultured for 10-12 days were used in the experiments.

EQUIVALENTS

Those skilled in the art will recognize, or be able to ascertain using no more than routine experimentation, many equivalents to the specific embodiments of the invention described herein. Such equivalents are intended to be encompassed by the following claims.

All patents, publications, and other references cited above are hereby incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

All publications and patents mentioned herein, including those items listed below, are hereby incorporated by reference in their entirety as if each individual publication or patent was specifically and individually indicated to be incorporated by reference. In case of conflict, the present application, including any definitions herein, will control. Also incorporated by reference in their entirety are any polynucleotide and polypeptide sequences which reference an accession number correlating to an entry in a public database, such as those maintained by The Institute for Genomic Research (TIGR) (See the TIGR website) and/or the National Center for Biotechnology Information (NCBI) (See the NCBI website).

Also incorporated by reference are the following: U.S. Pat. Nos. 6,413,942; 6,319,955; 6,451,837; Kemp and McKernan, Nature Neuroscience, 5(Supp): 1039-1042 (2002); Krapivinsky et al., Neuron 40: 775-784 (2003).

Also incorporated by reference are sequences referred to by their GenBank Accession Numbers throughout the application, as well as, the following sequences: NP_036706, NP_002882, NM_002891.3, NP_722522, AAD00659, U88963.

We claim:

1. An isolated complex comprising an NR2B polypeptide and a RasGRF1 polypeptide, wherein said NR2B polypeptide consists essentially of:
   (a) an amino acid sequence having at least 95% identity to the amino acid sequence comprising residues 886-1310 set forth in SEQ ID NO: 2 or 6 and which is less than 500 amino acids in length;
   (b) the amino acid sequence comprising residues 886-1310 set forth in SEQ ID NO: 2 or 6 with 1 to 10 conservative amino acid substitutions and which is less than 500 amino acids in length; or
   (c) the amino acid sequence comprising residues 886-1310 set forth in SEQ ID NO:2 or 6 and which is less than 500 amino acids in length;
   wherein the polypeptides of (a), (b), or (c) are capable of binding to a RasGRF1 polypeptide;
and wherein said RasGRF1 polypeptide consists essentially of:
   (a) an amino acid sequence having at least 95% identity to the amino acid sequence comprising residues 714-913 set forth in SEQ ID NO: 4 or comprising residues 732-942 set forth in SEQ ID NO: 8 and which is less than 500 amino acids in length;
   (b) the amino acid sequence comprising residues 714-913 set forth in SEQ ID NO: 4 or comprising residues 732-942 set forth in SEQ ID NO: 8 with 1 to 10 conservative amino acid substitutions and which is less than 500 amino acids in length; or
   (c) the amino acid sequence comprising residues 714-913 set forth in SEQ ID NO: 4 or comprising residues 732-942 set forth in SEQ ID NO: 8 and which is less than 500 amino acids in length;
   wherein the polypeptides of (a), (b), or (c) are capable of binding to an NR2B polypeptide.

2. The complex of claim 1, wherein at least one polypeptide is a fusion protein.

3. The complex of claim 1, wherein at least one polypeptide is labeled.

4. The complex of claim 1, wherein said complex is generated within a host cell.

5. The complex of claim 1, wherein said NR2B polypeptide or polypeptide fragment and said RasGRF1 polypeptide are covalently linked.

6. An isolated host cell comprising a recombinant nucleic acid sequence encoding at least one of the polypeptides of claim 1.

7. A composition comprising the complex of claim 1.

8. An isolated complex comprising an NR2B polypeptide and a RasGRF1 polypeptide, wherein said NR2B polypeptide consists of:
   (a) an amino acid sequence having at least 95% identity to the amino acid sequence comprising residues 886-1310 set forth in SEQ ID NO: 2 or 6 and which is less than 1000 amino acids in length;
   (b) the amino acid sequence comprising residues 886-1310 set forth in SEQ ID NO: 2 or 6 with 1 to 10 conservative amino acid substitutions and which is less than 1000 amino acids in length; or
   (c) the amino acid sequence comprising residues 886-1310 set forth in SEQ ID NO:2 or 6 and which is less than 1000 amino acids in length;
   wherein the polypeptides of (a), (b), or (c) are capable of binding to a RasGRF1 polypeptide;
and wherein said RasGRF1 polypeptide consists of:
   (a) an amino acid sequence having at least 95% identity to the amino acid sequence comprising residues 714-913 set forth in SEQ ID NO: 4 or comprising residues 732-942 set forth in SEQ ID NO: 8 and which is less than 1000 amino acids in length;
   (b) the amino acid sequence comprising residues 714-913 set forth in SEQ ID NO: 4 or comprising residues 732-942 set forth in SEQ ID NO: 8 with 1 to 10 conservative amino acid substitutions and which is less than 1000 amino acids in length; or
   (c) the amino acid sequence comprising residues 714-913 set forth in SEQ ID NO: 4 or comprising residues 732-942 set forth in SEQ ID NO: 8 and which is less than 1000 amino acids in length;
   wherein the polypeptides of (a), (b), or (c) are capable of binding to an NR2B polypeptide.

9. The complex of claim 8, wherein at least one polypeptide is a fusion protein.

10. The complex of claim 8, wherein at least one polypeptide is labeled.

11. The complex of claim 8, wherein said complex is generated within a host cell.

12. An isolated host cell comprising a recombinant nucleic acid sequence encoding an NR2B polypeptide of claim 8 and a recombinant nucleic acid sequence encoding a RasGRF1 polypeptide of claim 8.

13. A composition comprising the complex of claim 8.

14. An isolated complex consisting of an NR2B polypeptide comprising SEQ ID NO: 2 or 6 and a RasGRF1 polypeptide comprising SEQ ID NO: 4 or 8.

15. The complex of claim 14, wherein at least one polypeptide is a fusion protein.

16. The complex of claim 14, wherein at least one polypeptide is labeled.

17. The complex of claim 14, wherein said complex is generated within a host cell.

18. An isolated host cell comprising a recombinant nucleic acid sequence encoding an NR2B polypeptide of claim 14 and a recombinant nucleic acid sequence encoding a RasGRF1 polypeptide of claim 14.

19. A composition comprising the complex of claim 14.

* * * * *

SEQUENCE LISTING

<160> NUMBER OF SEQ ID NOS: 8

<210> SEQ ID NO 1
<211> LENGTH: 5259
<212> TYPE: DNA
<213> ORGANISM: Rattus norvegicus

<400> SEQUENCE: 1

```
gctgaagact ccttaaatat atatatatat atatatattc gggctactaa cctcacatgc      60
acatgggata atgactctgg attctgcatt gtgagctgct ctccacaccc tgagatcccc     120
tcttacatta cattttttcc tttgaatttg catctcgtca agacacaaga ttaaaaccaa     180
atttacacta cactggattt taaattttct tccgttcctt tatcctccgt ctttcttatg     240
tggatatgca agcgagaaga ggaccctgga tattcccaac atgctctctc ccttaatctg     300
tccgcctaga ggtttggcgt ctacaaacca agagagccga ctagctgaag atgaagccca     360
```

```
gcgcagagtg ctgttccccc aagttctggt tggtgttggc cgtcttggcc gtatcaggca    420
gcaaagctcg ttcccaaaag agccccccca gcatcggcat cgctgtcatc ctcgtgggca    480
cttcagacga agtggccata aaagacgccc acgagaaaga tgacttccat catctctcag    540
tagttccccg ggtggagctg gtagccatga acgaaactga cccaaagagc atcatcaccc    600
gtatctgcga tcttatgtct gaccggaaga tccaggnggt ggtgttcgcg gatgacaccg    660
accaagaagc catcgctcag atcctcgact tcatttctgc tcagactctc accccatcc    720 tgggcatcca tgggggctca tctatgataa tggcggataa ggatgagtcc tccatgttct    780
tccagtttgg cccgtctatc gaacagcaag cttccgtcat gctcaacatc atggaagaat    840
atgactggta catcttttcc atcgtcacca cctacttccc tggctaccag gactttgtga    900
acaagatccg cagtaccatc gagaacagct tcgtgggctg ggagctcgag gaagtcctcc    960
tgctagacat gtctctggac gatggcgact ctaagattca gaatcagctg aagaagctcc   1020
aaagccccat cattctcctt tattgcacga aggaggaagc cacctacatt tttgaagtag   1080
ctaactcagt tgggctgact ggctacggct acacgtggat tgtgccgagt ctggtggccg   1140
gggatacgga cacggtgcct tcagagttcc ccacggggct tatctctgtg tcttatgatg   1200
aatgggacta tggccttcct gccagagtga gagatggaat tgccatcatc accactgctg   1260
cctcggacat gctgtccgaa cacagtttca tccctgagcc caagagcagt tgctacaaca   1320
cccacgagaa gaggatctac cagtctaaca tgttgaatag gtatctgatc aatgtcactt   1380
ttgaagggag aaacctgtcc ttcagcgaag atggctacca gatgcatccg aagctggtga   1440
taatccttct gaacaaggag aggaagtggg agggtgggga aatggaag acaagtccc   1500 tgcagatgaa gtattatgtg tggcctcgga tgtgtcctga gactgaggag caagaggatg   1560
accatctgag cattgtcacc ttggaggagg cgccatttgt cattgtggaa agcgtggacc   1620
ctctcagtgg aacctgcatg aggaatacag tcccgtgcca gaagcgcatc atctctgaga   1680
ataaaacaga tgaggaacca ggctacatca aaaaatgctg caaggggttc tgtattgaca   1740
tccttaagaa aatttctaag tctgtgaagt tcacctatga cctttacctg gtgaccaatg   1800
gcaagcacgg gaagaagatt aatgggacct ggaatggcat gatcggtgag gtggtcatga   1860
agagggccta catggcagtg ggatcactaa ctatcaatga agaacggtca gaggtggttg   1920
acttctctgt acccttcata gaaactggca tcagtgtcat ggtatctcgc agcaatggga   1980
ctgtgtcacc ttctgccttc ttagagccat tcagcgctga cgtgtgggtg atgatgtttg   2040
tgatgctgct cattgtttct gcggtggctg tctttgtctt tgaatacttc agccctgtgg   2100
gttacaacag gtgcctagcc gatggcagag agccaggagg cccatctttc accatcggca   2160
aagcaatttg gttactctgg ggtctggtgt ttaacaactc cgtacctgtg cagaacccaa   2220
aggggaccac ctccaagatc atggtgtcag tgtgggcctt ctttgctgtc attttcctgg   2280
ccagctacac tgccaactta gcagccttca tgatccaaga ggagtatgtg gaccaggttt   2340
ctggcctgag tgacaagaag ttccagagac ctaatgactt ctcacccccct ttccgctttg   2400 ggactgtgcc caatggcagc acagagagga atatccgtaa taactatgca gaaatgcatg   2460
cctacatggg aaagttcaac caaggggtg tagatgatgc attgctctcc ctgaaaacag   2520
ggaagcttga tgcattcatc tatgatgcag ctgtgctcaa ctacatggct ggaagggacg   2580
aaggctgcaa actggtgacc attggcagtg gcaaggtctt tgcttctacc ggctatggca   2640
ttgctatcca aaaggactcc gggtggaagc gccaggtgga cctggctatc ctgcagctgt   2700
```

```
ttggagatgg ggagatggaa gaactggaag ctctctggct cactggcatt tgccacaatg    2760
agaagaatga ggtgatgagc agccagctgg acatcgacaa tatggcaggt gtcttctata    2820
tgttggggc agccatggcc ctcagcctca tcaccttcat ctgtgagcat ctgttctatt    2880
ggcagttccg gcattgcttc atgggtgtct gttctggcaa gcctggcatg gtcttctcca    2940
tcagcagagg tatctacagc tgtatccatg gggtagccat agaggagcgc caatccgtga    3000
tgaactcccc cactgccacc atgaacaaca cccactccaa catcctacgc ttgctccgca    3060
cggccaagaa catggccaac ctgtctggag taaacggctc ccctcagagt gccctggact    3120
tcatccgccg agagtcctcc gtctacgaca tctctgagca tcgtcgcagc ttcacgcatt    3180
cagactgcaa gtcttacaat aacccaccct gtgaggaaaa cctgttcagt gactacatta    3240
gcgaggtaga gagaacattt ggtaacctgc agctgaagga cagcaatgtg taccaagacc    3300
actatcacca tcaccaccgg ccacacagca tcggcagcac cagctccatt gatgggctct    3360
atgactgtga caacccaccc ttcaccaccc agcccaggtc aatcagcaag aaaccccctgg    3420
acatcggcct gccctcctcc aaacatagcc agctcagcga cctgtatggc aagttctctt    3480
tcaagagtga ccgctacagt ggccacgacg acttgattcg atcggatgtc tccgacatct    3540
ccacgcacac tgtcacctat gggaacatcg agggcaacgc agccaagagg aggaaacagc    3600
agtataagga cagtctaaag aagcggccag cctcggccaa atcgaggagg gagtttgatg    3660
aaatcgagct ggcctaccgt cgccgaccac cccgctcccc ggaccacaag cgctacttca    3720
gggacaaaga agggctccga gacttctacc tggaccagtt ccgaacaaag gagaactcgc    3780
ctcactggga gcacgtggac ttgactgaca tttacaaaga acgcagtgac gacttcaagc    3840
gagattcggt cagtggaggt gggccctgta ccaacaggtc tcacctcaaa cacggaacgg    3900
gcgagaagca cggagtggta ggcggggtgc ctgctccttg ggagaagaac ctgaccaatg    3960
tggattggga ggaccggtct gggggcaact tctgccgcag ctgtccttcc aagctgcaca    4020
attactcctc gacggtggca gggcagaact cgggccggca ggcctgcatc agatgtgagg    4080
cctgtaagaa ggctggtaac ctgtacgaca tcagcaagga caactccctg caggaactgg    4140
accagccggc tgcccccgtg gctgtgacat ccaacgcctc cagcaccaag taccctcaaa    4200
gcccgactaa ttccaaggct cagaagaaga atcggaacaa actgcgccgg cagcattcct    4260
acgacacctt cgtggacctg cagaaggagg aggccgcctt ggccccacgc agcgtgagcc    4320
tgaaagacaa gggccgattc atggatggga gccccctacgc ccatatgttt gagatgccag    4380
ctggtgagag ctcctttgcc aacaagtcct cagtgcccac tgccggacac caccacaaca    4440
acccggcag cggctacatg ctcagcaagt cgctctaccc tgaccgggtc acgcaaaacc    4500
ctttcatccc cacttttggg gatgaccagt gcttgcttca cggcagcaaa tcctacttct    4560
tcaggcagcc cacggtggca ggggcgtcaa aaacaaggcc ggacttccgg gcccttgtca    4620
ccaataagcc agtggtgtca gcccttcatg gggctgtgcc aggtcgtttc cagaaggaca    4680
tttgtatagg gaaccagtcc aaccctgtg tgcctaacaa caaaaacccc agggctttca    4740
atggctccag caatggacat gtttatgaga actttctag tattgagtct gatgtctgag    4800
tgagggaaga gagagaggtt aaggtgggta cgggagggat agggctgtgg gccgcgtggt    4860
gcgcatgtca tggaaagagt cggggtgaa cttggctccc attcgctttt tcttcttctt    4920
ttaatttctc tatgggatcc tggagttctg gttccttact gaaggcaacc ctcgtggcca    4980
gcaccatttc tcctccctcg cgcagttctc tccttcccgc atctgtccac cattcctgtt    5040
tccatgagag aatagaacgg ggcctcagtg tgggaggatg gagaggagac caaagcgctg    5100
```

-continued

```
cctgtgtgct tctttctagc gcagaagggc tcttagcagt tcactttgag cgaggctttc    5160
ctgatgctgc tctctttgtt caggtgagga agcgaaggtg ttctgaggaa ggccattgaa    5220
cctcctgttc ataagagaga agaggctttc actgaattc                          5259
```

<210> SEQ ID NO 2
<211> LENGTH: 1482
<212> TYPE: PRT
<213> ORGANISM: Rattus norvegicus

<400> SEQUENCE: 2

```
Met Lys Pro Ser Ala Glu Cys Cys Ser Pro Lys Phe Trp Leu Val Leu
 1               5                  10                  15

Ala Val Leu Ala Val Ser Gly Ser Lys Ala Arg Ser Gln Lys Ser Pro
            20                  25                  30

Pro Ser Ile Gly Ile Ala Val Ile Leu Val Gly Thr Ser Asp Glu Val
        35                  40                  45

Ala Ile Lys Asp Ala His Glu Lys Asp Asp Phe His His Leu Ser Val
    50                  55                  60

Val Pro Arg Val Glu Leu Val Ala Met Asn Glu Thr Asp Pro Lys Ser
65                  70                  75                  80

Ile Ile Thr Arg Ile Cys Asp Leu Met Ser Asp Arg Lys Ile Gln Gly
                85                  90                  95

Val Val Phe Ala Asp Asp Thr Asp Gln Glu Ala Ile Ala Gln Ile Leu
            100                 105                 110

Asp Phe Ile Ser Ala Gln Thr Leu Thr Pro Ile Leu Gly Ile His Gly
        115                 120                 125

Gly Ser Ser Met Ile Met Ala Asp Lys Asp Glu Ser Ser Met Phe Phe
    130                 135                 140

Gln Phe Gly Pro Ser Ile Glu Gln Gln Ala Ser Val Met Leu Asn Ile
145                 150                 155                 160

Met Glu Glu Tyr Asp Trp Tyr Ile Phe Ser Ile Val Thr Thr Tyr Phe
                165                 170                 175

Pro Gly Tyr Gln Asp Phe Val Asn Lys Ile Arg Ser Thr Ile Glu Asn
            180                 185                 190

Ser Phe Val Gly Trp Glu Leu Glu Glu Val Leu Leu Leu Asp Met Ser
        195                 200                 205

Leu Asp Asp Gly Asp Ser Lys Ile Gln Asn Gln Leu Lys Lys Leu Gln
    210                 215                 220

Ser Pro Ile Ile Leu Leu Tyr Cys Thr Lys Glu Glu Ala Thr Tyr Ile
225                 230                 235                 240

Phe Glu Val Ala Asn Ser Val Gly Leu Thr Gly Tyr Gly Tyr Thr Trp
                245                 250                 255

Ile Val Pro Ser Leu Val Ala Gly Asp Thr Asp Thr Val Pro Ser Glu
            260                 265                 270

Phe Pro Thr Gly Leu Ile Ser Val Ser Tyr Asp Glu Trp Asp Tyr Gly
        275                 280                 285

Leu Pro Ala Arg Val Arg Asp Gly Ile Ala Ile Ile Thr Thr Ala Ala
    290                 295                 300

Ser Asp Met Leu Ser Glu His Ser Phe Ile Pro Glu Pro Lys Ser Ser
305                 310                 315                 320

Cys Tyr Asn Thr His Glu Lys Arg Ile Tyr Gln Ser Asn Met Leu Asn
                325                 330                 335

Arg Tyr Leu Ile Asn Val Thr Phe Glu Gly Arg Asn Leu Ser Phe Ser
```

```
                    340                 345                 350
Glu Asp Gly Tyr Gln Met His Pro Lys Leu Val Ile Ile Leu Leu Asn
                355                 360                 365

Lys Glu Arg Lys Trp Glu Arg Val Gly Lys Trp Lys Asp Lys Ser Leu
    370                 375                 380

Gln Met Lys Tyr Tyr Val Trp Pro Arg Met Cys Pro Glu Thr Glu Glu
385                 390                 395                 400

Gln Glu Asp Asp His Leu Ser Ile Val Thr Leu Glu Glu Ala Pro Phe
            405                 410                 415

Val Ile Val Glu Ser Val Asp Pro Leu Ser Gly Thr Cys Met Arg Asn
        420                 425                 430

Thr Val Pro Cys Gln Lys Arg Ile Ile Ser Glu Asn Lys Thr Asp Glu
    435                 440                 445

Glu Pro Gly Tyr Ile Lys Lys Cys Cys Lys Gly Phe Cys Ile Asp Ile
    450                 455                 460

Leu Lys Lys Ile Ser Lys Ser Val Lys Phe Thr Tyr Asp Leu Tyr Leu
465                 470                 475                 480

Val Thr Asn Gly Lys His Gly Lys Lys Ile Asn Gly Thr Trp Asn Gly
            485                 490                 495

Met Ile Gly Glu Val Val Met Lys Arg Ala Tyr Met Ala Val Gly Ser
        500                 505                 510

Leu Thr Ile Asn Glu Glu Arg Ser Glu Val Val Asp Phe Ser Val Pro
    515                 520                 525

Phe Ile Glu Thr Gly Ile Ser Val Met Val Ser Arg Ser Asn Gly Thr
    530                 535                 540

Val Ser Pro Ser Ala Phe Leu Glu Pro Phe Ser Ala Asp Val Trp Val
545                 550                 555                 560

Met Met Phe Val Met Leu Leu Ile Val Ser Ala Val Ala Val Phe Val
            565                 570                 575

Phe Glu Tyr Phe Ser Pro Val Gly Tyr Asn Arg Cys Leu Ala Asp Gly
        580                 585                 590

Arg Glu Pro Gly Gly Pro Ser Phe Thr Ile Gly Lys Ala Ile Trp Leu
    595                 600                 605

Leu Trp Gly Leu Val Phe Asn Asn Ser Val Pro Val Gln Asn Pro Lys
    610                 615                 620

Gly Thr Thr Ser Lys Ile Met Val Ser Val Trp Ala Phe Phe Ala Val
625                 630                 635                 640

Ile Phe Leu Ala Ser Tyr Thr Ala Asn Leu Ala Ala Phe Met Ile Gln
            645                 650                 655

Glu Glu Tyr Val Asp Gln Val Ser Gly Leu Ser Asp Lys Lys Phe Gln
        660                 665                 670

Arg Pro Asn Asp Phe Ser Pro Pro Phe Arg Phe Gly Thr Val Pro Asn
    675                 680                 685

Gly Ser Thr Glu Arg Asn Ile Arg Asn Asn Tyr Ala Glu Met His Ala
    690                 695                 700

Tyr Met Gly Lys Phe Asn Gln Arg Gly Val Asp Asp Ala Leu Leu Ser
705                 710                 715                 720

Leu Lys Thr Gly Lys Leu Asp Ala Phe Ile Tyr Asp Ala Ala Val Leu
            725                 730                 735

Asn Tyr Met Ala Gly Arg Asp Glu Gly Cys Lys Leu Val Thr Ile Gly
        740                 745                 750

Ser Gly Lys Val Phe Ala Ser Thr Gly Tyr Gly Ile Ala Ile Gln Lys
    755                 760                 765
```

```
Asp Ser Gly Trp Lys Arg Gln Val Asp Leu Ala Ile Leu Gln Leu Phe
    770                 775                 780

Gly Asp Gly Glu Met Glu Leu Glu Ala Leu Trp Leu Thr Gly Ile
785                 790                 795                 800

Cys His Asn Glu Lys Asn Glu Val Met Ser Ser Gln Leu Asp Ile Asp
                805                 810                 815

Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
                885                 890                 895

Asn Ile Leu Arg Leu Leu Arg Thr Ala Lys Asn Met Ala Asn Leu Ser
            900                 905                 910

Gly Val Asn Gly Ser Pro Gln Ser Ala Leu Asp Phe Ile Arg Arg Glu
        915                 920                 925

Ser Ser Val Tyr Asp Ile Ser Glu His Arg Arg Ser Phe Thr His Ser
    930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
                965                 970                 975

Asp Ser Asn Val Tyr Gln Asp His Tyr His His His Arg Pro His
            980                 985                 990

Ser Ile Gly Ser Thr Ser Ser Ile Asp Gly Leu Tyr Asp Cys Asp Asn
        995                 1000                1005

Pro Pro Phe Thr Thr Gln Pro Arg Ser Ile Ser Lys Lys Pro Leu Asp
    1010                1015                1020

Ile Gly Leu Pro Ser Ser Lys His Ser Gln Leu Ser Asp Leu Tyr Gly
1025                1030                1035                1040

Lys Phe Ser Phe Lys Ser Asp Arg Tyr Ser Gly His Asp Asp Leu Ile
                1045                1050                1055

Arg Ser Asp Val Ser Asp Ile Ser Thr His Thr Val Thr Tyr Gly Asn
            1060                1065                1070

Ile Glu Gly Asn Ala Ala Lys Arg Arg Lys Gln Gln Tyr Lys Asp Ser
        1075                1080                1085

Leu Lys Lys Arg Pro Ala Ser Ala Lys Ser Arg Arg Glu Phe Asp Glu
    1090                1095                1100

Ile Glu Leu Ala Tyr Arg Arg Arg Pro Arg Ser Pro Asp His Lys
1105                1110                1115                1120

Arg Tyr Phe Arg Asp Lys Glu Gly Leu Arg Asp Phe Tyr Leu Asp Gln
                1125                1130                1135

Phe Arg Thr Lys Glu Asn Ser Pro His Trp Glu His Val Asp Leu Thr
            1140                1145                1150

Asp Ile Tyr Lys Glu Arg Ser Asp Asp Phe Lys Arg Asp Ser Val Ser
        1155                1160                1165

Gly Gly Gly Pro Cys Thr Asn Arg Ser His Leu Lys His Gly Thr Gly
    1170                1175                1180
```

| | | | | | | | | | | | |
|---|---|---|---|---|---|---|---|---|---|---|---|
|Glu|Lys|His|Gly|Val|Gly|Val|Pro|Ala|Pro|Trp|Glu|Lys|Asn|
|1185| | | |1190| | | |1195| | | |1200| |

Glu Lys His Gly Val Gly Val Pro Ala Pro Trp Glu Lys Asn
1185                1190                1195                1200

Leu Thr Asn Val Asp Trp Glu Asp Arg Ser Gly Gly Asn Phe Cys Arg
            1205                1210                1215

Ser Cys Pro Ser Lys Leu His Asn Tyr Ser Ser Thr Val Ala Gly Gln
        1220                1225                1230

Asn Ser Gly Arg Gln Ala Cys Ile Arg Cys Glu Ala Cys Lys Lys Ala
        1235                1240                1245

Gly Asn Leu Tyr Asp Ile Ser Lys Asp Asn Ser Leu Gln Glu Leu Asp
    1250                1255                1260

Gln Pro Ala Ala Pro Val Ala Val Thr Ser Asn Ala Ser Ser Thr Lys
1265                1270                1275                1280

Tyr Pro Gln Ser Pro Thr Asn Ser Lys Ala Gln Lys Lys Asn Arg Asn
            1285                1290                1295

Lys Leu Arg Arg Gln His Ser Tyr Asp Thr Phe Val Asp Leu Gln Lys
        1300                1305                1310

Glu Glu Ala Ala Leu Ala Pro Arg Ser Val Ser Leu Lys Asp Lys Gly
        1315                1320                1325

Arg Phe Met Asp Gly Ser Pro Tyr Ala His Met Phe Glu Met Pro Ala
    1330                1335                1340

Gly Glu Ser Ser Phe Ala Asn Lys Ser Ser Val Pro Thr Ala Gly His
1345                1350                1355                1360

His His Asn Asn Pro Gly Ser Gly Tyr Met Leu Ser Lys Ser Leu Tyr
            1365                1370                1375

Pro Asp Arg Val Thr Gln Asn Pro Phe Ile Pro Thr Phe Gly Asp Asp
        1380                1385                1390

Gln Cys Leu Leu His Gly Ser Lys Ser Tyr Phe Phe Arg Gln Pro Thr
        1395                1400                1405

Val Ala Gly Ala Ser Lys Thr Arg Pro Asp Phe Arg Ala Leu Val Thr
    1410                1415                1420

Asn Lys Pro Val Val Ser Ala Leu His Gly Ala Val Pro Gly Arg Phe
1425                1430                1435                1440

Gln Lys Asp Ile Cys Ile Gly Asn Gln Ser Asn Pro Cys Val Pro Asn
            1445                1450                1455

Asn Lys Asn Pro Arg Ala Phe Asn Gly Ser Ser Asn Gly His Val Tyr
        1460                1465                1470

Glu Lys Leu Ser Ser Ile Glu Ser Asp Val
        1475                1480

<210> SEQ ID NO 3
<211> LENGTH: 3804
<212> TYPE: DNA
<213> ORGANISM: Rattus rattus

<400> SEQUENCE: 3
ccgacgaggg gcagtcgggt gcctctcgga gatgtttagt gcgtgaggtc tctctggcct    60
ccaagcacca tgcagaaagc catccgactg aacgatggcc acgtcgtgtc cctgggactg   120
ctggcccaga gagacggtac gcgcaaaggc tacctgagca agaggagttc ggacaaccca   180
aaatggcaaa ccaagtggtt tgcgctgctg cagaacctgc tcttctactt cgaaagtgac   240
tcgagctctc ggccctcggg gctctacctg ctggagggca gtatctgcaa acgcatgccc   300
tcccccaagc gagggaccct ctccaaggag tccgacaaac agcatcatta cttcacagtg   360
aacttctcca tgacagccca gaagtcccta gagctgagga ccgatgactc caaggactgt   420

```
gacgagtggg tggcagcgat tgctcgcgcc agctacaaga tactggccac agagcatgag    480
gcgctcatgc agaagtacct gcacctgctg caggtggtgg agacagagaa gaccgtggct    540
aagcagctgc gacagcagct cgaggatggc gaggtcgaga tcgagcgcct gaaggcagag    600
attgcaaacc tgatcaagga caatgaacgt atccagtcca accagctggt tgcccctgag    660
gatgaggaca gtgacatcaa gaaaattaag aaggtacaga gtttccttcg cggatggctg    720
tgccggcgaa agtggaagaa catcatccag gactacatcc ggtctcctca tgccgacagc    780
atgcgcaaga ggaaccaggt ggtgttcagc atgctggaag ctgaggccga gtacgtgcag    840
caactacaca tccttgtcaa caattttctg cgcccactgc gcatggccgc cagctctaag    900
aaacccccta taacacatga cgacgtcagc agtatctttc tgaacagtga gaccatcatg    960
ttcctgcacc agatcttcta ccaaggcctg aaggcccgta tcgccagctg gcccacccctg    1020 gttctggcgg acctgttcga catcctgctg ccaatgctta acatctacca ggagttcgtc    1080
cgcaaccacc agtacagtct ccagatccta gcacactgca agcaaaaccg ggactttgac    1140
aagctcctca gcagtatgga ggccaagcca gactgcgagg agcgcacact ggagaccttc    1200
ctcacctatc caatgttcca gatccccagg tacatcctga cactccatga gctgctggcc    1260
cacacacctc atgagcatgt ggagcgcaac agcctggact atgccaaatc caaactagag    1320
gagctgtcca gggtcatgca cgacgaagtc agtgagaccg agaacatccg caaaaacctg    1380
gccattgagc gtatgatcac cgagggctgt gagatcctcc ttgacaccag ccagaccttt    1440
gtgcgccaag gttccctcat ccaggtgccc atgtcagaaa agggcaagat caacaagggc    1500
cgcctggggt ctctgtccct taagaaagaa ggtgagcgcc agtgtttcct gttctccaag    1560
catctcatca tctgcaccag aggctctggt agcaaactgc acctaaccaa gaatggcgtg    1620 atttcccctca ttgactgcac tctactggat gatccagaaa acatggatga tgacggcaaa    1680
ggacaagagg tagatcacct ggactttaag atttgggtgg agccaaagga ttccccaccc    1740
ttcacagtca tcctggtggc ctcatccagg caggagaagg cggcatggac cagtgacatc    1800
atccagtgcg tggataatat ccgctgcaac gggctcatga tgaatgcctt tgaagaaaat    1860
tccaaggtca ccgtgccgca gatgatcaag tctgatgctt ccttatactg tgatgatgtt    1920
gacattcgct tcagcaaaac catgaattct tgcaaagtgc tgcagatccg ctatgccagc    1980
gtggagcgcc tgctggagcg cctgactgat cttcgcttcc tgagtattga ctttctcaac    2040
accttcctgc actccatatcg agtcttcacc gatgctgtgg tggtcctaga caagctgatc    2100
agcatctaca aaaagcccat cactgcgatt cctgccaggt cactggaact cctgttctcc    2160
agtagccaca acaccaaact tctgtacgga gatgccccca gtcgcctcg tgccagccgc    2220 aagttctcct cgccgccgcc cttggccatc ggcacttcgt ccccagtccg ccgccggaag    2280
ttgtctctca acattcccat catcacaggc ggcaaggcgc tggaactggc ttcgctcggg    2340
tgcccctccg acggctacac caacatacac tcgcccatat ctcccttcgg caaaaccacg    2400
ctggacacca gcaagctctg tgtggccagc agcttgacca gaacgccgga ggagattgat    2460
atgaccactc tagaggagtc atcaggcttc aggaagccga cctcagacat cttgaaagaa    2520
gagtctgatg atgaccagag tgatgtagac gacacagaag tgtctccacc aacaccgaaa    2580
tcattcagaa acagaatcac tcaagagttc ccactcttta actacaacag tggaatcatg    2640
atgacatgtc gcgatctgat ggacagtaac cgcagccctc tgtcagctac ctctgccttt    2700
gccatagcga ctgcaggagc caatgaaagc cccgcaaaca aggagatata tcgaaggatg    2760
tctttggcca acacagggta ttcctctgac cagagaaata tcgacaaaga gttcgtgatc    2820
```

-continued

```
cgcagagcgg ccaccaaccg tgtactgaat gtgttgcgcc actgggtcac caagcactcc    2880
caggactttg aaactgacga cctcctcaaa tacaaggtga tctgctttct ggaagaggtc    2940
atgcatgacc cagaccttct accacaagag cgaaaggcag cagccaacat catgaggact    3000
ctgacccagg aagaaataac tgaaaaccat agcatgctgg atgagctctt actaatgacg    3060
gagggtgtga agactgagcc cttcgaaaac cactcagcca tggagatagc agagcagctg    3120
accctgctgg atcaccttgt cttcaagagt attccttatg aggaattctt tggccagggc    3180
tggatgaagg cagataagaa tgaaggaca ccttacatta tgaaaaccac cagacatttc    3240
aaccatatca gtaacttgat cgcttcagaa attctccgaa acgaggaggt cagtgcaagg    3300
gcaagcacca tcgagaagtg ggtggctgtt gccgacattt gccgctgcct gcacaactac    3360
aatgctgtgc tggagatcac ttcctccatc aaccgcagcg caatcttccg actcaagaag    3420
acatggctca agtttctaa gcagacgaaa tctctgtttg acaagctcca aaagcttgtg    3480
tcatcagatg gccgatttaa gaacctcaga gaaactttgc gaaattgtga tccaccctgt    3540
gtcccttacc tggggatgta cctgaccgac ttggcattcc tcgaggaagg aacacccaat    3600
tacacagagg acggcctggt caacttctcc aagatgagga tgatctccca tattatccgc    3660
gagattcgcc agtttcagca gactactac aaaatcgagc cccagccaaa ggtaactcag    3720
tacttagtgg atgaaacctt tgtgttggac gacgaaagtc tgtatgaggc ctccctccga    3780
attgaaccaa aactccccac atga                                            3804
```

<210> SEQ ID NO 4
<211> LENGTH: 1244
<212> TYPE: PRT
<213> ORGANISM: Rattus rattus

<400> SEQUENCE: 4

```
Met Gln Lys Ala Ile Arg Leu Asn Asp Gly His Val Val Ser Leu Gly
  1               5                  10                  15

Leu Leu Ala Gln Arg Asp Gly Thr Arg Lys Gly Tyr Leu Ser Lys Arg
             20                  25                  30

Ser Ser Asp Asn Pro Lys Trp Gln Thr Lys Trp Phe Ala Leu Leu Gln
         35                  40                  45

Asn Leu Leu Phe Tyr Phe Glu Ser Asp Ser Ser Arg Pro Ser Gly
     50                  55                  60

Leu Tyr Leu Leu Glu Gly Ser Ile Cys Lys Arg Met Pro Ser Pro Lys
 65                  70                  75                  80

Arg Gly Thr Ser Ser Lys Glu Ser Asp Lys Gln His His Tyr Phe Thr
                 85                  90                  95

Val Asn Phe Ser Asn Asp Ser Gln Lys Ser Leu Glu Leu Arg Thr Asp
            100                 105                 110

Asp Ser Lys Asp Cys Asp Glu Trp Val Ala Ala Ile Ala Arg Ala Ser
        115                 120                 125

Tyr Lys Ile Leu Ala Thr Glu His Glu Ala Leu Met Gln Lys Tyr Leu
    130                 135                 140

His Leu Leu Gln Val Val Glu Thr Glu Lys Thr Val Ala Lys Gln Leu
145                 150                 155                 160

Arg Gln Gln Leu Glu Asp Gly Glu Val Glu Ile Glu Arg Leu Lys Ala
                165                 170                 175

Glu Ile Ala Asn Leu Ile Lys Asp Asn Glu Arg Ile Gln Ser Asn Gln
            180                 185                 190
```

-continued

```
Leu Val Ala Pro Glu Asp Glu Ser Asp Ile Lys Lys Ile Lys Lys
        195                 200                 205

Val Gln Ser Phe Leu Arg Gly Trp Leu Cys Arg Arg Lys Trp Lys Asn
        210                 215                 220

Ile Ile Gln Asp Tyr Ile Arg Ser Pro His Ala Asp Ser Met Arg Lys
225                 230                 235                 240

Arg Asn Gln Val Val Phe Ser Met Leu Glu Ala Glu Ala Glu Tyr Val
                245                 250                 255

Gln Gln Leu His Ile Leu Val Asn Asn Phe Leu Arg Pro Leu Arg Met
            260                 265                 270

Ala Ala Ser Ser Lys Lys Pro Ile Thr His Asp Val Ser Ser
        275                 280                 285

Ile Phe Leu Asn Ser Glu Thr Ile Met Phe Leu His Gln Ile Phe Tyr
        290                 295                 300

Gln Gly Leu Lys Ala Arg Ile Ala Ser Trp Pro Thr Leu Val Leu Ala
305                 310                 315                 320

Asp Leu Phe Asp Ile Leu Leu Pro Met Leu Asn Ile Tyr Gln Glu Phe
                325                 330                 335

Val Arg Asn His Gln Tyr Ser Leu Gln Ile Leu Ala His Cys Lys Gln
                340                 345                 350

Asn Arg Asp Phe Asp Lys Leu Leu Lys Gln Tyr Glu Ala Lys Pro Asp
            355                 360                 365

Cys Glu Glu Arg Thr Leu Glu Thr Phe Leu Thr Tyr Pro Met Phe Gln
        370                 375                 380

Ile Pro Arg Tyr Ile Leu Thr Leu His Glu Leu Leu Ala His Thr Pro
385                 390                 395                 400

His Glu His Val Glu Arg Asn Ser Leu Asp Tyr Ala Lys Ser Lys Leu
                405                 410                 415

Glu Glu Leu Ser Arg Val Met His Asp Glu Val Ser Glu Thr Glu Asn
            420                 425                 430

Ile Arg Lys Asn Leu Ala Ile Glu Arg Met Ile Thr Glu Gly Cys Glu
        435                 440                 445

Ile Leu Leu Asp Thr Ser Gln Thr Phe Val Arg Gln Gly Ser Leu Ile
        450                 455                 460

Gln Val Pro Met Ser Glu Lys Gly Lys Ile Asn Lys Gly Arg Leu Gly
465                 470                 475                 480

Ser Leu Ser Leu Lys Lys Glu Gly Glu Arg Gln Cys Phe Leu Phe Ser
                485                 490                 495

Lys His Leu Ile Ile Cys Thr Arg Gly Ser Gly Ser Lys Leu His Leu
            500                 505                 510

Thr Lys Asn Gly Val Ile Ser Leu Ile Asp Cys Thr Leu Leu Asp Asp
        515                 520                 525

Pro Glu Asn Met Asp Asp Gly Lys Gly Gln Glu Val Asp His Leu
        530                 535                 540

Asp Phe Lys Ile Trp Val Glu Pro Lys Asp Ser Pro Pro Phe Thr Val
545                 550                 555                 560

Ile Leu Val Ala Ser Ser Arg Gln Glu Lys Ala Ala Trp Thr Ser Asp
                565                 570                 575

Ile Ile Gln Cys Val Asp Asn Ile Arg Cys Asn Gly Leu Met Met Asn
            580                 585                 590

Ala Phe Glu Glu Asn Ser Lys Val Thr Val Pro Gln Met Ile Lys Ser
        595                 600                 605

Asp Ala Ser Leu Tyr Cys Asp Asp Val Asp Ile Arg Phe Ser Lys Thr
```

-continued

```
              610                 615                 620
Met Asn Ser Cys Lys Val Leu Gln Ile Arg Tyr Ala Ser Val Glu Arg
625                 630                 635                 640

Leu Leu Glu Arg Leu Thr Asp Leu Arg Phe Leu Ser Ile Asp Phe Leu
                645                 650                 655

Asn Thr Phe Leu His Ser Tyr Arg Val Phe Thr Asp Ala Val Val Val
                660                 665                 670

Leu Asp Lys Leu Ile Ser Ile Tyr Lys Lys Pro Ile Thr Ala Ile Pro
                675                 680                 685

Ala Arg Ser Leu Glu Leu Leu Phe Ser Ser His Asn Thr Lys Leu
690                 695                 700

Leu Tyr Gly Asp Ala Pro Lys Ser Pro Arg Ala Ser Arg Lys Phe Ser
705                 710                 715                 720

Ser Pro Pro Leu Ala Ile Gly Thr Ser Ser Pro Val Arg Arg Arg
                725                 730                 735

Lys Leu Ser Leu Asn Ile Pro Ile Ile Thr Gly Gly Lys Ala Leu Glu
                740                 745                 750

Leu Ala Ser Leu Gly Cys Pro Ser Asp Gly Tyr Thr Asn Ile His Ser
        755                 760                 765

Pro Ile Ser Pro Phe Gly Lys Thr Thr Leu Asp Thr Ser Lys Leu Cys
        770                 775                 780

Val Ala Ser Ser Leu Thr Arg Thr Pro Glu Glu Ile Asp Met Thr Thr
785                 790                 795                 800

Leu Glu Glu Ser Ser Gly Phe Arg Lys Pro Thr Ser Asp Ile Leu Lys
                805                 810                 815

Glu Glu Ser Asp Asp Asp Gln Ser Asp Val Asp Asp Thr Glu Val Ser
                820                 825                 830

Pro Pro Thr Pro Lys Ser Phe Arg Asn Arg Ile Thr Gln Glu Phe Pro
                835                 840                 845

Leu Phe Asn Tyr Asn Ser Gly Ile Met Met Thr Cys Arg Asp Leu Met
        850                 855                 860

Asp Ser Asn Arg Ser Pro Leu Ser Ala Thr Ser Ala Phe Ala Ile Ala
865                 870                 875                 880

Thr Ala Gly Ala Asn Glu Ser Pro Ala Asn Lys Glu Ile Tyr Arg Arg
                885                 890                 895

Met Ser Leu Ala Asn Thr Gly Tyr Ser Ser Asp Gln Arg Asn Ile Asp
                900                 905                 910

Lys Glu Phe Val Ile Arg Arg Ala Ala Thr Asn Arg Val Leu Asn Val
                915                 920                 925

Leu Arg His Trp Val Thr Lys His Ser Gln Asp Phe Glu Thr Asp Asp
930                 935                 940

Leu Leu Lys Tyr Lys Val Ile Cys Phe Leu Glu Glu Val Met His Asp
945                 950                 955                 960

Pro Asp Leu Leu Pro Gln Glu Arg Lys Ala Ala Asn Ile Met Arg
                965                 970                 975

Thr Leu Thr Gln Glu Glu Ile Thr Glu Asn His Ser Met Leu Asp Glu
                980                 985                 990

Leu Leu Leu Met Thr Glu Gly Val Lys Thr Glu Pro Phe Glu Asn His
                995                 1000                1005

Ser Ala Met Glu Ile Ala Glu Gln Leu Thr Leu Leu Asp His Leu Val
        1010                1015                1020

Phe Lys Ser Ile Pro Tyr Glu Glu Phe Phe Gly Gln Gly Trp Met Lys
1025                1030                1035                1040
```

Ala Asp Lys Asn Glu Arg Thr Pro Tyr Ile Met Lys Thr Thr Arg His
            1045                1050                1055

Phe Asn His Ile Ser Asn Leu Ile Ala Ser Glu Ile Leu Arg Asn Glu
        1060                1065                1070

Glu Val Ser Ala Arg Ala Ser Thr Ile Glu Lys Trp Val Ala Val Ala
    1075                1080                1085

Asp Ile Cys Arg Cys Leu His Asn Tyr Asn Ala Val Leu Glu Ile Thr
1090                1095                1100

Ser Ser Ile Asn Arg Ser Ala Ile Phe Arg Leu Lys Lys Thr Trp Leu
1105                1110                1115                1120

Lys Val Ser Lys Gln Thr Lys Ser Leu Phe Asp Lys Leu Gln Lys Leu
            1125                1130                1135

Val Ser Ser Asp Gly Arg Phe Lys Asn Leu Arg Glu Thr Leu Arg Asn
        1140                1145                1150

Cys Asp Pro Pro Cys Val Pro Tyr Leu Gly Met Tyr Leu Thr Asp Leu
    1155                1160                1165

Ala Phe Leu Glu Glu Gly Thr Pro Asn Tyr Thr Glu Asp Gly Leu Val
    1170                1175                1180

Asn Phe Ser Lys Met Arg Met Ile Ser His Ile Ile Arg Glu Ile Arg
1185                1190                1195                1200

Gln Phe Gln Gln Thr Thr Tyr Lys Ile Glu Pro Gln Pro Lys Val Thr
            1205                1210                1215

Gln Tyr Leu Val Asp Glu Thr Phe Val Leu Asp Asp Glu Ser Leu Tyr
        1220                1225                1230

Glu Ala Ser Leu Arg Ile Glu Pro Lys Leu Pro Thr
    1235                1240

<210> SEQ ID NO 5
<211> LENGTH: 6208
<212> TYPE: DNA
<213> ORGANISM: Homo sapiens

<400> SEQUENCE: 5

| | | |
|---|---|---|
| taaaacaaaa tttacgctaa attggatttt aaattatctt ccgttcattt atccttcgtc | 60 |
| tttcttatgt ggatatgcaa gcagaagaa gggactggac attcccaaca tgctcactcc | 120 |
| cttaatctgt ccgtctagag gtttggcttc tacaaaccaa gggagtcgac gagttgaaga | 180 |
| tgaagcccag agcggagtgc tgttctccca agttctggtt ggtgttggcc gtcctggcgg | 240 |
| tgtcaggcag cagagctcgt tctcagaaga gccccccag cattggcatt gctgtcatcc | 300 |
| tcgtgggcac ttccgacgag gtggccatca aggatgccca cgagaaagat gatttccacc | 360 |
| atctctccgt ggtaccccgg gtggaactgg tagccatgaa tgagaccgac ccaaagagca | 420 |
| tcatcacccg catctgtgat ctcatgtctg accggaagat ccaggggtg gtgtttgctg | 480 |
| atgacacaga ccaggaagcc atcgcccaga tcctcgattt catttcagca cagactctca | 540 |
| cccccatcct gggcatccac gggggctcct ctatgataat ggcagataag gatgaatcct | 600 |
| ccatgttctt ccagtttggc ccatcaattg aacagcaagc ttccgtaatg ctcaacatca | 660 |
| tggaagaata tgactggtac atcttttcta tcgtcaccac ctatttccct ggctaccagg | 720 |
| actttgtaaa caagatccgc agcaccattg agaatgctt tgtgggctgg agctagagg | 780 |
| aggtcctcct actggacatg tccctggacg atggagattc taagatccag aatcagctca | 840 |
| agaaacttca aagccccatc attcttcttt actgtaccaa ggaagaagcc acctacatct | 900 |
| ttgaagtggc caactcagta gggctgactg gctatggcta cacgtggatc gtgcccagtc | 960 |

-continued

```
tggtggcagg ggatacagac acagtgcctg cggagttccc cactgggctc atctctgtat   1020
catatgatga atgggactat ggcctccccg ccagagtgag agatggaatt gccataatca   1080
ccactgctgc ttctgacatg ctgtctgagc acagcttcat ccctgagccc aaaagcagtt   1140
gttacaacac ccacgagaag agaatctacc agtccaatat gctaaatagg tatctgatca   1200
atgtcacttt tgaggggagg aatttgtcct tcagtgaaga tggctaccag atgcacccga   1260
aactggtgat aattcttctg aacaaggaga ggaagtggga aagggtgggg aagtggaaag   1320
acaagtccct gcagatgaag tactatgtgt ggccccgaat gtgtccagag actgaagagc   1380
aggaggatga ccatctgagc attgtgaccc tggaggaggc accatttgtc attgtggaaa   1440
gtgtggaccc tctgagtgga acctgcatga ggaacacagc cccctgccaa aaacgcatag   1500
tcactgagaa taagacagac gaggagccgg gttacatcaa aaaatgctgc aagggggttct   1560
gtattgacat ccttaagaaa atttctaaat ctgtgaagtt cacctatgac ctttacctgg   1620
ttaccaatgg caagcatggg aagaaaatca atggaacctg gaatggtatg attggagagg   1680
tggtcatgaa gagggcctac atggcagtgg gctcactcac catcaatgag gaacgatcgg   1740
aggtggtcga cttctctgtg cccttcatag agacaggcat cagtgtcatg gtgtcacgca   1800
gcaatgggac tgtctcacct tctgccttct tagagccatt cagcgctgac gtatgggtga   1860
tgatgtttgt gatgctgctc atcgtctcag ccgtggctgt ctttgtcttt gagtacttca   1920
gccctgtggg ttataacagg tgcctcgctg atggcagaga gcctggtgga ccctctttca   1980
ccatcggcaa agctatttgg ttgctctggg gtctggtgtt taacaactcc gtacctgtgc   2040
agaacccaaa ggggaccacc tccaagatca tggtgtcagt gtgggccttc tttgctgtca   2100
tcttcctggc cagctacact gccaacttag ctgccttcat gatccaagag gaatatgtgg   2160
accaggtttc tggcctgagc gacaaaaagt ccagagacc taatgacttc tcacccccctt   2220
tccgcttttgg gaccgtgccc aacggcagca cagagagaaa tattcgcaat aactatgcag   2280
aaatgcatgc ctacatggga aagttcaacc agaggggtgt agatgatgca ttgctctccc   2340
tgaaaacagg gaaactggat gccttcatct atgatgcagc agtgctgaac tatatggcag   2400
gcagagatga aggctgcaag ctggtgacca ttggcagtgg gaaggtcttt gcttccactg   2460
gctatggcat tgccatccaa aaagattctg ggtggaagcg ccaggtggac cttgctatcc   2520
tgcagctctt tggagatggg gagatggaag aactggaagc tctctggctc actggcattt   2580
gtcacaatga agaatgag gtcatgagca gccagctgga cattgacaac atggcagggg   2640
tcttctacat gttgggggcg ccatggctc tcagcctcat caccttcatc tgcgaacacc   2700
ttttctattg gcagttccga cattgcttta tgggtgtctg ttctggcaag cctggcatgg   2760
tcttctccat cagcagaggt atctacagct gcatccatgg ggtggcgatc gaggagcgcc   2820
agtctgtaat gaactccccc accgcaacca tgaacaacac acactccaac atcctgcgcc   2880
tgctgcgcac ggccaagaac atggctaacc tgtctggtgt gaatggctca ccgcagagcg   2940
ccctggactt catccgacgg gagtcatccg tctatgacat ctcagagcac cgccgcagct   3000
tcacgcattc tgactgcaaa tcctacaaca acccgccctg tgaggagaac ctcttcagtg   3060
actacatcag tgaggtagag agaacgttcg ggaacctgca gctgaaggac agcaacgtgt   3120
accaagatca ctaccaccat caccaccggc ccatagtat tggcagtgcc agctccatcg   3180
atgggctcta cgactgtgac aacccaccct tcaccaccca gtccaggtcc atcagcaaga   3240
agccccctgga catcggcctc ccctcctcca agcacagcca gctcagtgac ctgtacggca   3300
```

```
aattctcctt caagagcgac cgctacagtg gccacgacga cttgatccgc tccgatgtct    3360
ctgacatctc aacccacacc gtcacctatg ggaacatcga gggcaatgcc gccaagaggc    3420
gtaagcagca atataaggac agcctgaaga agcggcctgc ctcggccaag tcccgcaggg    3480
agtttgacga gatcgagctg gcctaccgtc gccgaccgcc ccgctcccct gaccacaagc    3540
gctacttcag ggacaaggaa gggctacggg acttctacct ggaccagttc cgaacaaagg    3600
agaactcacc ccactgggag cacgtagacc tgaccgacat ctacaaggag cggagtgatg    3660
actttaagcg cgactccgtc agcggaggag ggccctgtac caacaggtcc catatcaagc    3720
acgggacggg cgacaaacac ggcgtggtca gcggggtacc tgcaccttgg gagaagaacc    3780
tgaccaacgt ggagtgggag gaccggtccg ggggcaactt ctgccgcagc tgtccctcca    3840
agctgcacaa ctactccacg acggtgacgg gtcagaactc gggcaggcag gcgtgcatcc    3900
ggtgtgaggc ttgcaagaaa gcaggcaacc tgtatgacat cagtgaggac aactccctgc    3960
aggaactgga ccagccggct gccccagtgg cggtgacgtc aaacgcctcc accactaagt    4020
accctcagag cccgactaat tccaaggccc agaagaagaa ccggaacaaa ctgcgccggc    4080
agcactccta cgacaccttc gtggacctgc agaaggaaga agccgccctg ccccgcgca    4140 gcgtaagcct gaaagacaag ggccgattca tggatgggag ccctacgcc cacatgtttg    4200 agatgtcagc tggcgagagc acctttgcca caacaagtc ctcagtgccc actgccggac    4260
atcaccacca caacaacccc ggcggcgggt acatgctcag caagtcgctc taccctgacc    4320
gggtcacgca aaaccctttc atccccactt ttggggacga ccagtgcttg ctccatggca    4380
gcaaatccta cttcttcagg cagcccacgg tggcggggc gtcgaaagcc aggccggact    4440 tccgggcccct tgtcaccaac aagccggtgg tctcggccct tcatgggcc gtgccagccc    4500 gtttccagaa ggacatctgt atagggaacc agtccaaccc ctgtgtgcct aacaacaaaa    4560
accccagggc tttcaatggc tccagcaatg ggcatgttta tgagaaactt tctagtattg    4620
agtctgatgt ctgagtgagg aacagagag gttaaggtgg gtacgggagg gtaaggctgt    4680
gggtcgcgtg atgcgcatgt cacggagggt gacggggtg aacttggttc ccatttgctc    4740 cttcttgtt ttaatttatt tatggggatc ctggagttct ggttcctact gggggcaacc    4800
ctggtgacca gcaccatctc tcctcctttt cacagttctc tccttcttcc ccccgctctc    4860
agccattcct gttcccatga gatgatgcca tgggtctcag caggggaggg tagagcggag    4920
aaaggaaggg cagcatgcgg gcttcctcct ggtgtggaag agctccttga tatcctcttt    4980
gagtgaagct gggagaacca aaaagaggct atgtgagcac aaaggtagct tttcccaaac    5040
tgatcttttc atttaggtga ggaagcaaaa gcatctatgt gagaccattt agcacactgc    5100
ttgtgaaagg aaagaggctc tggctaaatt catgctgctt agatgacatc tgtctaggaa    5160
tcatggtcca agcagaggtt gggaggccat ttgtgtttat atataagcca aaaatgctt    5220 gcttcaaccc catgagactc gatagtggtg gtgaacagaa caaaggtca ttggtggcag    5280 agtggattct tgaacaaact ggaaagtacg ttatgatagt gtcccacggt gccttgggga    5340
caagagcagg tggattgtgc gtgcatgtgt gttcatgcac acttgcaccc atgtgtagtc    5400
aggtgcctca agagaaggca accttgactc tttctattgt ttctttcaat atccccaagc    5460
agtgtgattg tttggcttat atacagacag agatggccat gtattacctg aattttggct    5520
gtgtctccct tcatccttct ggaataagga gaatgaaaat tcttgataaa gaagattctg    5580
tggtctaaac aaaaaaaggc ggtgagcaat cctgcaagag caaggtacat aaacaagtcc    5640
tcagtggttg gcaactgttt caacttgttt gaaccaagaa ccttccagga aggctaaagg    5700
```

-continued

```
gaaaccgaat tcacagcca tgattctttt gcccacactt gggacgaaaa gattctacaa    5760
agctcttttg agcatttaga ctctcgactg gccaaggttt ggggaagaac gaacggacct    5820
ttgaagaagt aaggagtcgt gtatggtagg gtaagtgaga gagggggatg tttcctatgc    5880
tttgatccct tctcacttaa cctgaagcta gacgagcagg cttcttcccc ccaaaactga    5940
ttacaactgc tacagagcag acagttaaga gaaatgagct tgacatttaa gagaaatgag    6000
ctgcactcca tgagtgcagc tctggaggta cgaaagagg ggaagagact tggaaatggg     6060
agacgggggc agagagggac cctccaccac ctctttgggc ctggctgggt gggaatgtga    6120
cttgagccca gagtgaacac tcttggtaga agcccttcta ccttcctgca acacctgttc    6180
cctctcagat tgtaccattg agccggaa                                       6208
```

<210> SEQ ID NO 6
<211> LENGTH: 1484
<212> TYPE: PRT
<213> ORGANISM: Homo sapiens

<400> SEQUENCE: 6

```
Met Lys Pro Arg Ala Glu Cys Cys Ser Pro Lys Phe Trp Leu Val Leu
  1               5                  10                  15

Ala Val Leu Ala Val Ser Gly Ser Arg Ala Arg Ser Gln Lys Ser Pro
             20                  25                  30

Pro Ser Ile Gly Ile Ala Val Ile Leu Val Gly Thr Ser Asp Glu Val
         35                  40                  45

Ala Ile Lys Asp Ala His Glu Lys Asp Asp Phe His His Leu Ser Val
     50                  55                  60

Val Pro Arg Val Glu Leu Val Ala Met Asn Glu Thr Asp Pro Lys Ser
 65                  70                  75                  80

Ile Ile Thr Arg Ile Cys Asp Leu Met Ser Asp Arg Lys Ile Gln Gly
                 85                  90                  95

Val Val Phe Ala Asp Asp Thr Asp Gln Glu Ala Ile Ala Gln Ile Leu
            100                 105                 110

Asp Phe Ile Ser Ala Gln Thr Leu Thr Pro Ile Leu Gly Ile His Gly
        115                 120                 125

Gly Ser Ser Met Ile Met Ala Asp Lys Asp Glu Ser Ser Met Phe Phe
    130                 135                 140

Gln Phe Gly Pro Ser Ile Glu Gln Gln Ala Ser Val Met Leu Asn Ile
145                 150                 155                 160

Met Glu Glu Tyr Asp Trp Tyr Ile Phe Ser Ile Val Thr Thr Tyr Phe
                165                 170                 175

Pro Gly Tyr Gln Asp Phe Val Asn Lys Ile Arg Ser Thr Ile Glu Asn
            180                 185                 190

Ser Phe Val Gly Trp Glu Leu Glu Glu Val Leu Leu Leu Asp Met Ser
        195                 200                 205

Leu Asp Asp Gly Asp Ser Lys Ile Gln Asn Gln Leu Lys Lys Leu Gln
    210                 215                 220

Ser Pro Ile Ile Leu Leu Tyr Cys Thr Lys Glu Ala Thr Tyr Ile
225                 230                 235                 240

Phe Glu Val Ala Asn Ser Val Gly Leu Thr Gly Tyr Gly Tyr Thr Trp
                245                 250                 255

Ile Val Pro Ser Leu Val Ala Gly Asp Thr Asp Thr Val Pro Ala Glu
            260                 265                 270

Phe Pro Thr Gly Leu Ile Ser Val Ser Tyr Asp Glu Trp Asp Tyr Gly
```

-continued

```
                275                 280                 285
Leu Pro Ala Arg Val Arg Asp Gly Ile Ala Ile Thr Thr Ala Ala
290                 295                 300
Ser Asp Met Leu Ser Glu His Ser Phe Ile Pro Glu Pro Lys Ser Ser
305                 310                 315                 320
Cys Tyr Asn Thr His Glu Lys Arg Ile Tyr Gln Ser Asn Met Leu Asn
                325                 330                 335
Arg Tyr Leu Ile Asn Val Thr Phe Glu Gly Arg Asn Leu Ser Phe Ser
                340                 345                 350
Glu Asp Gly Tyr Gln Met His Pro Lys Leu Val Ile Ile Leu Leu Asn
                355                 360                 365
Lys Glu Arg Lys Trp Glu Arg Val Gly Lys Trp Lys Asp Lys Ser Leu
370                 375                 380
Gln Met Lys Tyr Tyr Val Trp Pro Arg Met Cys Pro Glu Thr Glu Glu
385                 390                 395                 400
Gln Glu Asp Asp His Leu Ser Ile Val Thr Leu Glu Glu Ala Pro Phe
                405                 410                 415
Val Ile Val Glu Ser Val Asp Pro Leu Ser Gly Thr Cys Met Arg Asn
                420                 425                 430
Thr Ala Pro Cys Gln Lys Arg Ile Val Thr Glu Asn Lys Thr Asp Glu
                435                 440                 445
Glu Pro Gly Tyr Ile Lys Lys Cys Cys Lys Gly Phe Cys Ile Asp Ile
                450                 455                 460
Leu Lys Lys Ile Ser Lys Ser Val Lys Phe Thr Tyr Asp Leu Tyr Leu
465                 470                 475                 480
Val Thr Asn Gly Lys His Gly Lys Lys Ile Asn Gly Thr Trp Asn Gly
                485                 490                 495
Met Ile Gly Glu Val Val Met Lys Arg Ala Tyr Met Ala Val Gly Ser
                500                 505                 510
Leu Thr Ile Asn Glu Glu Arg Ser Glu Val Val Asp Phe Ser Val Pro
                515                 520                 525
Phe Ile Glu Thr Gly Ile Ser Val Met Val Ser Arg Ser Asn Gly Thr
530                 535                 540
Val Ser Pro Ser Ala Phe Leu Glu Pro Phe Ser Ala Asp Val Trp Val
545                 550                 555                 560
Met Met Phe Val Met Leu Leu Ile Val Ser Ala Val Ala Val Phe Val
                565                 570                 575
Phe Glu Tyr Phe Ser Pro Val Gly Tyr Asn Arg Cys Leu Ala Asp Gly
                580                 585                 590
Arg Glu Pro Gly Gly Pro Ser Phe Thr Ile Gly Lys Ala Ile Trp Leu
                595                 600                 605
Leu Trp Gly Leu Val Phe Asn Asn Ser Val Pro Val Gln Asn Pro Lys
610                 615                 620
Gly Thr Thr Ser Lys Ile Met Val Ser Val Trp Ala Phe Phe Ala Val
625                 630                 635                 640
Ile Phe Leu Ala Ser Tyr Thr Ala Asn Leu Ala Ala Phe Met Ile Gln
                645                 650                 655
Glu Glu Tyr Val Asp Gln Val Ser Gly Leu Ser Asp Lys Lys Phe Gln
                660                 665                 670
Arg Pro Asn Asp Phe Ser Pro Pro Phe Arg Phe Gly Thr Val Pro Asn
                675                 680                 685
Gly Ser Thr Glu Arg Asn Ile Arg Asn Asn Tyr Ala Glu Met His Ala
                690                 695                 700
```

```
Tyr Met Gly Lys Phe Asn Gln Arg Gly Val Asp Asp Ala Leu Leu Ser
705                 710                 715                 720
Leu Lys Thr Gly Lys Leu Asp Ala Phe Ile Tyr Asp Ala Ala Val Leu
            725                 730                 735
Asn Tyr Met Ala Gly Arg Asp Glu Gly Cys Lys Leu Val Thr Ile Gly
                740                 745                 750
Ser Gly Lys Val Phe Ala Ser Thr Gly Tyr Gly Ile Ala Ile Gln Lys
            755                 760                 765
Asp Ser Gly Trp Lys Arg Gln Val Asp Leu Ala Ile Leu Gln Leu Phe
770                 775                 780
Gly Asp Gly Glu Met Glu Glu Leu Glu Ala Leu Trp Leu Thr Gly Ile
785                 790                 795                 800
Cys His Asn Glu Lys Asn Glu Val Met Ser Ser Gln Leu Asp Ile Asp
                805                 810                 815
Asn Met Ala Gly Val Phe Tyr Met Leu Gly Ala Ala Met Ala Leu Ser
                820                 825                 830
Leu Ile Thr Phe Ile Cys Glu His Leu Phe Tyr Trp Gln Phe Arg His
            835                 840                 845
Cys Phe Met Gly Val Cys Ser Gly Lys Pro Gly Met Val Phe Ser Ile
850                 855                 860
Ser Arg Gly Ile Tyr Ser Cys Ile His Gly Val Ala Ile Glu Glu Arg
865                 870                 875                 880
Gln Ser Val Met Asn Ser Pro Thr Ala Thr Met Asn Asn Thr His Ser
                885                 890                 895
Asn Ile Leu Arg Leu Leu Arg Thr Ala Lys Asn Met Ala Asn Leu Ser
                900                 905                 910
Gly Val Asn Gly Ser Pro Gln Ser Ala Leu Asp Phe Ile Arg Arg Glu
            915                 920                 925
Ser Ser Val Tyr Asp Ile Ser Glu His Arg Arg Ser Phe Thr His Ser
            930                 935                 940
Asp Cys Lys Ser Tyr Asn Asn Pro Pro Cys Glu Glu Asn Leu Phe Ser
945                 950                 955                 960
Asp Tyr Ile Ser Glu Val Arg Thr Phe Gly Asn Leu Gln Leu Lys
                965                 970                 975
Asp Ser Asn Val Tyr Gln Asp His Tyr His His His Arg Pro His
            980                 985                 990
Ser Ile Gly Ser Ala Ser Ser Ile Asp Gly Leu Tyr Asp Cys Asp Asn
            995                 1000                1005
Pro Pro Phe Thr Thr Gln Ser Arg Ser Ile Ser Lys Lys Pro Leu Asp
    1010                1015                1020
Ile Gly Leu Pro Ser Ser Lys His Ser Gln Leu Ser Asp Leu Tyr Gly
1025                1030                1035                1040
Lys Phe Ser Phe Lys Ser Asp Arg Tyr Ser Gly His Asp Asp Leu Ile
                1045                1050                1055
Arg Ser Asp Val Ser Asp Ile Ser Thr His Thr Val Thr Tyr Gly Asn
                1060                1065                1070
Ile Glu Gly Asn Ala Ala Lys Arg Arg Lys Gln Gln Tyr Lys Asp Ser
            1075                1080                1085
Leu Lys Lys Arg Pro Ala Ser Ala Lys Ser Arg Glu Phe Asp Glu
            1090                1095                1100
Ile Glu Leu Ala Tyr Arg Arg Arg Pro Pro Arg Ser Pro Asp His Lys
1105                1110                1115                1120
```

```
Arg Tyr Phe Arg Asp Lys Glu Gly Leu Arg Asp Phe Tyr Leu Asp Gln
            1125                1130                1135

Phe Arg Thr Lys Glu Asn Ser Pro His Trp Glu His Val Asp Leu Thr
            1140                1145                1150

Asp Ile Tyr Lys Glu Arg Ser Asp Asp Phe Lys Arg Asp Ser Val Ser
            1155                1160                1165

Gly Gly Gly Pro Cys Thr Asn Arg Ser His Ile Lys His Gly Thr Gly
            1170                1175                1180

Asp Lys His Gly Val Val Ser Gly Val Pro Ala Pro Trp Glu Lys Asn
1185                1190                1195                1200

Leu Thr Asn Val Glu Trp Glu Asp Arg Ser Gly Gly Asn Phe Cys Arg
            1205                1210                1215

Ser Cys Pro Ser Lys Leu His Asn Tyr Ser Thr Thr Val Thr Gly Gln
            1220                1225                1230

Asn Ser Gly Arg Gln Ala Cys Ile Arg Cys Glu Ala Cys Lys Lys Ala
            1235                1240                1245

Gly Asn Leu Tyr Asp Ile Ser Glu Asp Asn Ser Leu Gln Glu Leu Asp
            1250                1255                1260

Gln Pro Ala Ala Pro Val Ala Val Thr Ser Asn Ala Ser Thr Thr Lys
1265                1270                1275                1280

Tyr Pro Gln Ser Pro Thr Asn Ser Lys Ala Gln Lys Lys Asn Arg Asn
            1285                1290                1295

Lys Leu Arg Arg Gln His Ser Tyr Asp Thr Phe Val Asp Leu Gln Lys
            1300                1305                1310

Glu Glu Ala Ala Leu Ala Pro Arg Ser Val Ser Leu Lys Asp Lys Gly
            1315                1320                1325

Arg Phe Met Asp Gly Ser Pro Tyr Ala His Met Phe Glu Met Ser Ala
            1330                1335                1340

Gly Glu Ser Thr Phe Ala Asn Asn Lys Ser Ser Val Pro Thr Ala Gly
1345                1350                1355                1360

His His His His Asn Asn Pro Gly Gly Gly Tyr Met Leu Ser Lys Ser
            1365                1370                1375

Leu Tyr Pro Asp Arg Val Thr Gln Asn Pro Phe Ile Pro Thr Phe Gly
            1380                1385                1390

Asp Asp Gln Cys Leu Leu His Gly Ser Lys Ser Tyr Phe Phe Arg Gln
            1395                1400                1405

Pro Thr Val Ala Gly Ala Ser Lys Ala Arg Pro Asp Phe Arg Ala Leu
            1410                1415                1420

Val Thr Asn Lys Pro Val Val Ser Ala Leu His Gly Ala Val Pro Ala
1425                1430                1435                1440

Arg Phe Gln Lys Asp Ile Cys Ile Gly Asn Gln Ser Asn Pro Cys Val
            1445                1450                1455

Pro Asn Asn Lys Asn Pro Arg Ala Phe Asn Gly Ser Ser Asn Gly His
            1460                1465                1470

Val Tyr Glu Lys Leu Ser Ser Ile Glu Ser Asp Val
            1475                1480

<210> SEQ ID NO 7
<211> LENGTH: 4022
<212> TYPE: DNA
<213> ORGANISM: Homo sapiens

<400> SEQUENCE: 7
atgcagaagg ggatccggct gaatgatggc cacgtcgcgt ccctgggact gctggcgcgc    60
```

```
aaggacggca cgcgcaaagg ctacctgagc aagcggagtt cggacaacac aaaatggcaa    120
accaagtggt tcgcgctgct gcagaacctg ctcttctact tcgagagcga ctcgagctcg    180 cggcccctcgg ggctttacct gctggagggc tgcgtctgcg accgcgcgcc ctcccccaag    240
ccggcgctgt cggccaagga gccgctggag aaacagcatt acttcacggt gaacttcagc    300
catgagaacc agaaagcctt ggagctgagg acagaggacg caaaagattg tgacgaatgg    360
gtggcagcca ttgcacatgc cagctacagg accctcgcca cagagcatga ggcattaatg    420
cagaaatacc tgcacctgct gcagatcgtg gagacagaga agaccgtggc caagcagctt    480
cggcagcaga tcgaggatgg ggagatcgag atcgagcggc tgaaggcaga gatcacatcc    540
ctgctcaagg acaatgagcg catccagtcc acccagactg tcgcccccaa cgatgaagac    600
agcgacatca agaaaattaa gaaggtgcag agcttcctgc ggggctggct gtgccggcgg    660
aagtggaaga ccatcatcca ggactacatc cggtcacccc atgctgacag catgcgcaag    720
aggaaccagg tggtgttcag catgctggag gctgaggctg agtacgtgca gcagctgcac    780
atccttgtca acaatttcct gcgcccgctg cggatggccg ccagctccaa gaagcctccc    840
atcacacacg acgacgtcag cagcatcttc ctgaacagcg aaaccatcat gttttttacat    900 cagatctttt accaaggcct gaaggcccgc atctccagct ggcccacgct ggtcctggct    960
gacctatttg acatcctgct gcccatgctc aacatctacc aagagttcgt ccgcaaccac   1020
cagtacagcc tgcagatcct ggcccactgc aagcagaacc gtgacttcga caagctgctg   1080
aagcactacg aggccaagcc tgactgcgag gagaggacgc tggagacctt cctcacctac   1140
cccatgttcc agatccccag gtacatcctg accctccatg agctcctggc ccacacgcct   1200
catgagcacg ttgagcgcaa cagcctggac tacgccaagt ccaaactgga ggagctgtcc   1260
agaataatgc acgatgaagt aagtgagacg gagaacatcc ggaaaaacct ggccatcgag   1320
cgcatgatca tcgaaggctg tgagatcctc ctggacacca gccagacctt tgtgagacaa   1380
ggttccctca ttcaggtgcc catgtctgaa aagggcaaga tcaccagggg gcgcctgggg   1440
tctctctccc taaagaaaga gggcgagcga cagtgcttcc tgttttctaa gcatctgatt   1500
atctgtacca gaggctctgg agggaagctt cacttgacca agaatggagt catatccctc   1560
attgactgca ctttattgga ggagccagaa agcacggagg aggaagccaa aggatccggc   1620
caagacatag atcacttgga ttttaaaatc ggggtggagc caaaggattc cccgcccttt   1680
acagtcatcc tagtggcctc gtccagacag gagaaggcag cgtggaccag tgacatcagc   1740
cagtgtgtgg ataacatccg atgcaatggg ctcatgatga acgcatttga agaaaattcc   1800
aaggtcactg tgccgcagat gatcaagagg accaggagg ggaccaggga agcagaaatg   1860
agcaggtccg acgcctcctt atattgtgat gatgttgaca ttcgcttcag caaaaccatg   1920
aactcctgca aagtgctgca gatccgctac gccagtgtgg agcggctgct ggagaggctg   1980
acggacctgc gcttcctgag catcgacttc ctcaacacct tcctgcactc ctaccgcgtc   2040
ttcaccaccg ccatcgtggt cctggacaag ctcattacca tctacaagaa gcctatcagt   2100
gccattcctg ccaggtggct gaggtcgctg gagctcctgt tgccagtgg ccagaacaat   2160 aagctcctgt acggtgaacc ccccaagtcc ccgcgcgcca cccgcaagtt ctcctcgccg   2220
ccacctctgt ccatcaccaa gacatcgtca ccgagccgcc ggcggaagct ctccctgaac   2280
atccccatca tcactggcgg caaggccctg gacctggccg ccctcagctg caactccaat   2340
ggctacacca gcatgtactc ggccatgtca cccttcagca aggccacgct ggacaccagc   2400
aagctctatg tgtccagcag cttcaccaac aagattccag atgagggcga tacgacccct   2460
```

-continued

```
gagaagcccg aagacccttc agcgctcagc aagcagagct cagaagtctc catgagagag    2520
gagtcagata ttgatcaaaa ccagagtgat gatggtgata ctgaaacatc accaactaaa    2580
tctccaacaa cacccaaatc agtcaaaaac aaaaattctt cagagttccc actcttttcc    2640
tataacaatg gagtcgtcat gacctcctgt cgtgaactgg acaataaccg cagtgccttg    2700
tcggccgcct ctgcctttgc catagcaacc gccggggcca acgagggcac ccaaacaag     2760
gagaagtacc ggaggatgtc cttagccagt gcagggtttc ccccagacca gaggaatgga    2820
gacaaggagt ttgtgatccg cagagcagcc accaatcgtg tcttgaacgt gctccgccac    2880
tgggtgtcca agcactctca ggactttgag accaacgatg agctcaaatg caaggtgatc    2940
ggcttcctgg aagaagtcat gcacgacccg gagctcctga cccaggagcg gaaggctgca    3000
gccaacatca tcaggactct gacccaggag acccaggtg acaaccagat cacgctggag     3060
gagatcacgc agatggctga aggcgtgaag gctgagccct ttgaaaacca ctcagccctg    3120
gagatcgcgg agcagctgac cctgctagat cacctcgtct tcaagaagat tccttatgag    3180
gagttcttcg acaaggatg gatgaaactg gaaaagaatg aaaggacccc ttatatcatg     3240
aaaaccacta agcacttcaa tgacatcagt aacttgattg cttcagaaat catccgcaat    3300
gaggacatca acgccagggt gagcgccatc gagaagtggg tggccgtagc tgacatatgc    3360
cgctgcctcc acaactacaa tgccgtactg gagatcacct cgtccatgaa ccgcagtgca    3420
atcttccggc tcaaaaagac gtggctcaaa gtctctaagc agactaaagc tttgattgat    3480
aagctccaaa agcttgtgtc atctgagggc agatttaaga atctcagaga agctctgaaa    3540
aattgtgacc caccctgtgt cccttacctg gggatgtacc tcaccgacct ggccttcatc    3600
gaggagggga cgcccaatta cacggaagac ggcctggtca acttctccaa gatgaggatg    3660
atatcccata ttatccgaga gattcgccag tttcaacaaa ctgcctacaa aatagagcac    3720
caagcaaagg taacgcaata tttactggac caatcttttg taatggatga agaaagcctc    3780
tacgagtctt ctctccgaat agaaccaaaa ctcccccacct gaagctgagc ccagcccaga    3840
cccagctgct cccggggaca tgtgctagat gatactgtac atattcgttt ggtttcactg    3900
gatttttcttc ttcagtatgt gcttctccaa gaatacaaat cgtccttgtt cttagattcc    3960
tgtagaaccg gaatatgaat ttctgcaccg tttcagactt cgcccaccca tccctcccct    4020
cg                                                                   4022
```

<210> SEQ ID NO 8
<211> LENGTH: 1273
<212> TYPE: PRT
<213> ORGANISM: Homo sapiens

<400> SEQUENCE: 8

```
Met Gln Lys Gly Ile Arg Leu Asn Asp Gly His Val Ala Ser Leu Gly
  1               5                  10                  15

Leu Leu Ala Arg Lys Asp Gly Thr Arg Lys Gly Tyr Leu Ser Lys Arg
             20                  25                  30

Ser Ser Asp Asn Thr Lys Trp Gln Thr Lys Trp Phe Ala Leu Leu Gln
         35                  40                  45

Asn Leu Leu Phe Tyr Phe Glu Ser Asp Ser Ser Arg Pro Ser Gly
     50                  55                  60

Leu Tyr Leu Leu Glu Gly Cys Val Cys Asp Arg Ala Pro Ser Pro Lys
 65                  70                  75                  80

Pro Ala Leu Ser Ala Lys Glu Pro Leu Glu Lys Gln His Tyr Phe Thr
```

-continued

```
                85                  90                  95
Val Asn Phe Ser His Glu Asn Gln Lys Ala Leu Glu Leu Arg Thr Glu
            100                 105                 110
Asp Ala Lys Asp Cys Asp Glu Trp Val Ala Ala Ile Ala His Ala Ser
            115                 120                 125
Tyr Arg Thr Leu Ala Thr Glu His Glu Ala Leu Met Gln Lys Tyr Leu
            130                 135                 140
His Leu Leu Gln Ile Val Glu Thr Glu Lys Thr Val Ala Lys Gln Leu
145                 150                 155                 160
Arg Gln Gln Ile Glu Asp Gly Glu Ile Glu Ile Glu Arg Leu Lys Ala
                165                 170                 175
Glu Ile Thr Ser Leu Leu Lys Asp Asn Glu Arg Ile Gln Ser Thr Gln
            180                 185                 190
Thr Val Ala Pro Asn Asp Glu Asp Ser Asp Ile Lys Lys Ile Lys Lys
            195                 200                 205
Val Gln Ser Phe Leu Arg Gly Trp Leu Cys Arg Arg Lys Trp Lys Thr
            210                 215                 220
Ile Ile Gln Asp Tyr Ile Arg Ser Pro His Ala Asp Ser Met Arg Lys
225                 230                 235                 240
Arg Asn Gln Val Val Phe Ser Met Leu Glu Ala Glu Ala Glu Tyr Val
                245                 250                 255
Gln Gln Leu His Ile Leu Val Asn Asn Phe Leu Arg Pro Leu Arg Met
            260                 265                 270
Ala Ala Ser Ser Lys Lys Pro Pro Ile Thr His Asp Asp Val Ser Ser
            275                 280                 285
Ile Phe Leu Asn Ser Glu Thr Ile Met Phe Leu His Gln Ile Phe Tyr
            290                 295                 300
Gln Gly Leu Lys Ala Arg Ile Ser Ser Trp Pro Thr Leu Val Leu Ala
305                 310                 315                 320
Asp Leu Phe Asp Ile Leu Leu Pro Met Leu Asn Ile Tyr Gln Glu Phe
                325                 330                 335
Val Arg Asn His Gln Tyr Ser Leu Gln Ile Leu Ala His Cys Lys Gln
            340                 345                 350
Asn Arg Asp Phe Asp Lys Leu Leu Lys His Tyr Glu Ala Lys Pro Asp
            355                 360                 365
Cys Glu Glu Arg Thr Leu Glu Thr Phe Leu Thr Tyr Pro Met Phe Gln
            370                 375                 380
Ile Pro Arg Tyr Ile Leu Thr Leu His Glu Leu Leu Ala His Thr Pro
385                 390                 395                 400
His Glu His Val Glu Arg Asn Ser Leu Asp Tyr Ala Lys Ser Lys Leu
                405                 410                 415
Glu Glu Leu Ser Arg Ile Met His Asp Glu Val Ser Glu Thr Glu Asn
            420                 425                 430
Ile Arg Lys Asn Leu Ala Ile Glu Arg Met Ile Ile Glu Gly Cys Glu
            435                 440                 445
Ile Leu Leu Asp Thr Ser Gln Thr Phe Val Arg Gln Gly Ser Leu Ile
            450                 455                 460
Gln Val Pro Met Ser Glu Lys Gly Lys Ile Thr Arg Gly Arg Leu Gly
465                 470                 475                 480
Ser Leu Ser Leu Lys Lys Glu Gly Glu Arg Gln Cys Phe Leu Phe Ser
                485                 490                 495
Lys His Leu Ile Ile Cys Thr Arg Gly Ser Gly Gly Lys Leu His Leu
            500                 505                 510
```

```
Thr Lys Asn Gly Val Ile Ser Leu Ile Asp Cys Thr Leu Leu Glu Glu
            515                 520                 525

Pro Glu Ser Thr Glu Glu Ala Lys Gly Ser Gly Gln Asp Ile Asp
    530                 535                 540

His Leu Asp Phe Lys Ile Gly Val Glu Pro Lys Asp Ser Pro Pro Phe
545                 550                 555                 560

Thr Val Ile Leu Val Ala Ser Ser Arg Gln Glu Lys Ala Ala Trp Thr
                565                 570                 575

Ser Asp Ile Ser Gln Cys Val Asp Asn Ile Arg Cys Asn Gly Leu Met
            580                 585                 590

Met Asn Ala Phe Glu Glu Asn Ser Lys Val Thr Val Pro Gln Met Ile
        595                 600                 605

Lys Arg Thr Arg Glu Gly Thr Arg Glu Ala Glu Met Ser Arg Ser Asp
    610                 615                 620

Ala Ser Leu Tyr Cys Asp Asp Val Asp Ile Arg Phe Ser Lys Thr Met
625                 630                 635                 640

Asn Ser Cys Lys Val Leu Gln Ile Arg Tyr Ala Ser Val Glu Arg Leu
                645                 650                 655

Leu Glu Arg Leu Thr Asp Leu Arg Phe Leu Ser Ile Asp Phe Leu Asn
            660                 665                 670

Thr Phe Leu His Ser Tyr Arg Val Phe Thr Thr Ala Ile Val Val Leu
        675                 680                 685

Asp Lys Leu Ile Thr Ile Tyr Lys Lys Pro Ile Ser Ala Ile Pro Ala
    690                 695                 700

Arg Trp Leu Arg Ser Leu Glu Leu Leu Phe Ala Ser Gly Gln Asn Asn
705                 710                 715                 720

Lys Leu Leu Tyr Gly Glu Pro Lys Ser Pro Arg Ala Thr Arg Lys
                725                 730                 735

Phe Ser Ser Pro Pro Pro Leu Ser Ile Thr Lys Thr Ser Ser Pro Ser
            740                 745                 750

Arg Arg Arg Lys Leu Ser Leu Asn Ile Pro Ile Ile Thr Gly Gly Lys
        755                 760                 765

Ala Leu Asp Leu Ala Ala Leu Ser Cys Asn Ser Asn Gly Tyr Thr Ser
    770                 775                 780

Met Tyr Ser Ala Met Ser Pro Phe Ser Lys Ala Thr Leu Asp Thr Ser
785                 790                 795                 800

Lys Leu Tyr Val Ser Ser Ser Phe Thr Asn Lys Ile Pro Asp Glu Gly
                805                 810                 815

Asp Thr Thr Pro Glu Lys Pro Glu Asp Pro Ser Ala Leu Ser Lys Gln
            820                 825                 830

Ser Ser Glu Val Ser Met Arg Glu Glu Ser Asp Ile Asp Gln Asn Gln
        835                 840                 845

Ser Asp Asp Gly Asp Thr Glu Thr Ser Pro Thr Lys Ser Pro Thr Thr
    850                 855                 860

Pro Lys Ser Val Lys Asn Lys Asn Ser Ser Glu Phe Pro Leu Phe Ser
865                 870                 875                 880

Tyr Asn Asn Gly Val Val Met Thr Ser Cys Arg Glu Leu Asp Asn Asn
                885                 890                 895

Arg Ser Ala Leu Ser Ala Ser Ala Phe Ala Ile Ala Thr Ala Gly
            900                 905                 910

Ala Asn Glu Gly Thr Pro Asn Lys Glu Lys Tyr Arg Arg Met Ser Leu
        915                 920                 925
```

-continued

```
Ala Ser Ala Gly Phe Pro Pro Asp Gln Arg Asn Gly Asp Lys Glu Phe
    930                 935                 940

Val Ile Arg Arg Ala Ala Thr Asn Arg Val Leu Asn Val Leu Arg His
945                 950                 955                 960

Trp Val Ser Lys His Ser Gln Asp Phe Glu Thr Asn Asp Glu Leu Lys
                965                 970                 975

Cys Lys Val Ile Gly Phe Leu Glu Val Met His Asp Pro Glu Leu
            980                 985                 990

Leu Thr Gln Glu Arg Lys Ala Ala Ala Asn Ile Ile Arg Thr Leu Thr
            995                1000                1005

Gln Glu Asp Pro Gly Asp Asn Gln Ile Thr Leu Glu Glu Ile Thr Gln
   1010                1015                1020

Met Ala Glu Gly Val Lys Ala Glu Pro Phe Glu Asn His Ser Ala Leu
1025                1030                1035                1040

Glu Ile Ala Glu Gln Leu Thr Leu Leu Asp His Leu Val Phe Lys Lys
                1045                1050                1055

Ile Pro Tyr Glu Glu Phe Phe Gly Gln Gly Trp Met Lys Leu Glu Lys
            1060                1065                1070

Asn Glu Arg Thr Pro Tyr Ile Met Lys Thr Thr Lys His Phe Asn Asp
            1075                1080                1085

Ile Ser Asn Leu Ile Ala Ser Glu Ile Ile Arg Asn Glu Asp Ile Asn
        1090                1095                1100

Ala Arg Val Ser Ala Ile Glu Lys Trp Val Ala Val Ala Asp Ile Cys
1105                1110                1115                1120

Arg Cys Leu His Asn Tyr Asn Ala Val Leu Glu Ile Thr Ser Ser Met
                1125                1130                1135

Asn Arg Ser Ala Ile Phe Arg Leu Lys Lys Thr Trp Leu Lys Val Ser
            1140                1145                1150

Lys Gln Thr Lys Ala Leu Ile Asp Lys Leu Gln Lys Leu Val Ser Ser
            1155                1160                1165

Glu Gly Arg Phe Lys Asn Leu Arg Glu Ala Leu Lys Asn Cys Asp Pro
        1170                1175                1180

Pro Cys Val Pro Tyr Leu Gly Met Tyr Leu Thr Asp Leu Ala Phe Ile
1185                1190                1195                1200

Glu Glu Gly Thr Pro Asn Tyr Thr Glu Asp Gly Leu Val Asn Phe Ser
                1205                1210                1215

Lys Met Arg Met Ile Ser His Ile Ile Arg Glu Ile Arg Gln Phe Gln
            1220                1225                1230

Gln Thr Ala Tyr Lys Ile Glu His Gln Ala Lys Val Thr Gln Tyr Leu
            1235                1240                1245

Leu Asp Gln Ser Phe Val Met Asp Glu Glu Ser Leu Tyr Glu Ser Ser
        1250                1255                1260

Leu Arg Ile Glu Pro Lys Leu Pro Thr
1265                1270
```